(12) United States Patent
Alsina-Fernandez et al.

(10) Patent No.: US 10,894,817 B2
(45) Date of Patent: Jan. 19, 2021

(54) FATTY ACID MODIFIED UROCORTIN-2 ANALOGS FOR THE TREATMENT OF DIABETES AND CHRONIC KIDNEY DISEASE

(71) Applicant: Eli Lilly and Company, Indianapolis, IN (US)

(72) Inventors: Jorge Alsina-Fernandez, Indianapolis, IN (US); Lili Guo, Carmel, IN (US); John Lee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 232 days.

(21) Appl. No.: 15/648,542

(22) Filed: Jul. 13, 2017

(65) Prior Publication Data

US 2018/0016318 A1   Jan. 18, 2018

Related U.S. Application Data

(60) Provisional application No. 62/491,385, filed on Apr. 28, 2017, provisional application No. 62/431,682, filed on Dec. 8, 2016, provisional application No. 62/362,711, filed on Jul. 15, 2016.

(51) Int. Cl.
| | | |
|---|---|---|
| C07K 14/575 | (2006.01) | |
| A61K 38/00 | (2006.01) | |
| A61K 9/00 | (2006.01) | |
| C07K 14/47 | (2006.01) | |
| A61K 38/22 | (2006.01) | |

(52) U.S. Cl.
CPC ...... C07K 14/57509 (2013.01); A61K 9/0019 (2013.01); C07K 14/575 (2013.01); A61K 38/00 (2013.01); A61K 38/2228 (2013.01); C07K 14/4705 (2013.01)

(58) Field of Classification Search
CPC .............................................. C07K 14/57509
See application file for complete search history.

(56) References Cited

U.S. PATENT DOCUMENTS

| | | | |
|---|---|---|---|
| 9,572,866 B2 | 2/2017 | Vale, Jr. et al. | |
| 2002/0082409 A1 | 6/2002 | Hsu et al. | |
| 2003/0036507 A1 | 2/2003 | Vale, Jr. et al. | |
| 2004/0034882 A1 | 2/2004 | Vale, Jr. et al. | |
| 2007/0042954 A1 | 2/2007 | Chen et al. | |
| 2008/0161235 A1 | 7/2008 | Chen et al. | |
| 2012/0238509 A1 | 9/2012 | Vale, Jr. et al. | |
| 2013/0109621 A1 | 5/2013 | Huising et al. | |
| 2016/0166651 A1 | 6/2016 | Hammond et al. | |

FOREIGN PATENT DOCUMENTS

| | | | |
|---|---|---|---|
| CA | 2987489 A1 * | 6/2016 | |
| WO | 9534651 | 12/1995 | |
| WO | 9700063 | 1/1997 | |
| WO | 0212307 A1 | 2/2002 | |
| WO | 03062268 A2 | 7/2003 | |
| WO | 03062269 A2 | 7/2003 | |
| WO | WO-03062268 A2 * | 7/2003 | ....... C07K 14/57509 |
| WO | 2004047866 A2 | 6/2004 | |
| WO | 2005103690 A2 | 1/2005 | |
| WO | 2006031322 A2 | 3/2006 | |
| WO | 2007090087 A2 | 8/2007 | |
| WO | 2008047241 A2 | 4/2008 | |
| WO | 2008157302 A2 | 12/2008 | |
| WO | 2010053990 A2 | 5/2010 | |
| WO | 2011025905 A1 | 5/2011 | |
| WO | 2011057027 A2 | 8/2011 | |
| WO | 2011092293 A2 | 8/2011 | |
| WO | 2011095450 A1 | 8/2011 | |

(Continued)

OTHER PUBLICATIONS

UKPDS (Intensive blood-glucose control with sulphonylureas or insulin compared with conventional treatment and risk of complications in patients with type 2 diabetes (UKPDS 33), Lancet 1998; 352: 837-53) (Year: 1998).*

Pechmann (Interplay between Chaperones and Protein Disorder Promotes the Evolution of Protein Networks. PLoS Comput Biol 2014, 10(6): e1003674) (Year: 2014).*

Varlund (N-terminal modifications of cellular proteins: The enzymes involved, their substrate specificities and biological effects, Proteomics 2015, 15, 2385-2401) (Year: 2015).*

Betts (Amino Acid Properties and Consequences of Substitutions in Bioinformatics for Geneticists. 2003 John Wiley & Sons, Ltd., ISBNs: 0-470-84393-4) (Year: 2003).*

(Continued)

*Primary Examiner* — Sergio Coffa
(74) *Attorney, Agent, or Firm* — Brian C Cholewa

(57) ABSTRACT

The present invention provides a compound or a pharmaceutically acceptable salt of the Formula:

$$X_1IVX_2SLDVPIGLLQILX_3EQEKQEKEKQQAK*TNAX_4ILAQV-NH_2$$

wherein the $X_1$ denotes that the I residue is modified by either acetylation or methylation at the N-terminus; wherein $X_2$ is L or T; wherein $X_3$ is L or I; wherein $X_4$ is Q or E; and wherein a modified K residue ("K*") at position 29 is modified through conjugation to the epsilon-amino group of the K-side chain with a group of the formula —$X_5$—$X_6$, wherein $X_5$ is selected from the group consisting of one to four amino acids; one to four ([2-(2-Amino-ethoxy)-ethoxy]-acetyl) moieties; and combinations of one to four amino acids and one to four ([2-(2-Amino-ethoxy)-ethoxy]-acetyl) moieties; and $X_6$ is a $C_{14}$-$C_{24}$ fatty acid. In some embodiments, the group of the formula —$X_5$—$X_6$ is ([2-(2-Amino-ethoxy)-ethoxy]-acetyl)$_2$-(γE)$_2$-CO—(CH$_2$)$_x$—CO$_2$H where x is 16 or 18.

24 Claims, No Drawings

Specification includes a Sequence Listing.

(56) References Cited

FOREIGN PATENT DOCUMENTS

WO    WO-2017220706 A1 *  12/2017  .........  A61K 38/1825

OTHER PUBLICATIONS

Jamieson (Urocortin 3 transgenic mice exhibit a metabolically favourable phenotype resisting obesity and hyperglycaemia on a high-fat diet, Diabetologia 2011, 54:2392-2403) (Year: 2011).*

Li (Excitatory responses of cardiovascular activities to urocortin3 administration into the PVN of the rat, Autonomic Neuroscience: Basic and Clinical 2010, 154:108-111) (Year: 2010).*

Isfort et al.; "Modifications of the human urocortin 2 peptide that improve pharmacological properties" Peptides 27 (2006); 1806-1813.

Fekete and Zorrilla; "Physiology, pharmacology, and therapeutic relevance of urocortins in mammals: Ancient CRF paralogs" Frontiers in Neuroendocrinology 28 (2007); 1-27.

Mackay et al.; "Effects of a selective agonist and antagonist of CRF2 receptors on cardiovascular function in the rat" European Journal of Pharmacology 469 (2003); 111-115.

Roberts et al,; "Chemistry for peptide and protein PEGylation" Advanced Drug Delivery Reviews 54 (2002); 459-476.

Veronese; "Peptide and protein PEGylation: a review of problems and solutions" Biomaterials 22 (2001 ); 405-417.

Hafer-Macko et al.; "Skeletal muscle changes after hemiparetic stroke and potential beneficial effects of exercise intervention strategies" Journal of Rehabilitation Research & Development 45 (2) (2008); 261-272.

Berge et al.; "Pharmaceutical Salts" Journal of Pharmaceutical Sciences 66 (1) (1977) 1-19.

Surwit et al.; "Diet-Induced Type II Diabetes in C57BL/6J Mice" Diabetes 37 (1988); 1163-1167.

Kleft et al.; "Rapid on-line determination of cholesterol distribution among plasma lipoproteins after high-performance gel filtration chromatography" Journal of Lipid Research 32 (1991); 859-866.

Coleman; "Obese and Diabetes: Two Mutant Genes Causing Diabetes—Obesity Syndromes in Mice" Diabetologia 14 (1978): 141-148.

Krawiec et al.; "Hindlimb casting decreases muscle mass in part by proteasome-dependent proteolysis but independent of protein synthesis" Am J Physiol Endocrinol Metab 289 (2005): E969-E980.

Hakim et al.; "Evaluation of Muscle Function of the Extensor Digitorum Longus Muscle Ex vivo and Tibialis Anterior Muscle In situ in Mice" Journal of Visualized Experiments (2013).

Ninichuk et al.; "Tubular Atrophy, Interstitial Fibrosis, and Inflammation in Type 2 Diabetic db/db Mice. An Accelerated Model of Advanced Diabetic Nephropathy" European Journal of Medical Research 12 (2007); 351-355.

Ma and Fogo; "Model of robust induction of glomerulosclerosis in mice: Importance of genetic background" Kidney International 64 (2003): 350-355.

Kishimoto et al.; "Deletion of Crhr2 reveals an anxiolytic role for corticotropin-releasing hormone receptor-2" Nature Genetics 24 (2000); 415-419.

Dimosthenis Giamouridis, et al.; "Urocortin-3 Gene Transfer Increases Function of the Failing Heart in Mice", *the FASEB Journal*, (Apr. 2017); vol. 31 No. 1, Supplement 687.13.

Gao, et al.; One-time injection of AAV8 encoding urocortin 2 provides long-term resolution of insulin resistance, JCI Insight; (Sep. 22, 2016).

Chen, et al; "Urocortin 2 modulates glucose utilitzation and insulin sensitivity in skeletal muscle", *PNAS*, (Oct. 31, 2006); vol. 103, No. 44, 16580-16585.

PCT/US2017/041922 Written Opinion dated Sep. 25, 2017.

* cited by examiner

FATTY ACID MODIFIED UROCORTIN-2 ANALOGS FOR THE TREATMENT OF DIABETES AND CHRONIC KIDNEY DISEASE

The present invention relates to novel urocortin-2 compounds, pharmaceutical compositions comprising the compounds, methods of using the compounds to treat disorders associated with corticotropin releasing hormone receptor-2, and intermediates and processes useful in the synthesis of the compounds.

Urocortin-2 (UCN2) is a thirty-eight amino acid endogenous peptide (SEQ ID NO: 15). It is one of three known endogenous urocortins (UCN1 and UCN3) found in mammals and is part of the corticotropin-releasing hormone (CRH; also referred to as corticotropin releasing factor) family. The CRH family exhibits many physiological functions. UCN peptides are short acting. They act through CRH receptors (CRHR) known as CRHR1 and/or CRHR2. Specifically, UCN2 selectively activates CRHR2 including known isoforms CRHR2-alpha (α) -beta (β)) and -gamma (γ). UCN2 also has been associated with a reduction in blood pressure. *European Journal of Pharmacology* 469: 111-115 (2003).

Type II diabetes (T2D) is the most common form of diabetes accounting for approximately 90% of all diabetes. Over 300 million people worldwide are diagnosed with T2D. It is characterized by high blood glucose levels caused by insulin-resistance. The current standard of care for T2D includes diet and exercise as underlying adjunctive therapy along with available oral and injectable glucose lowering drugs. Nonetheless, patients with T2D still remain inadequately controlled. An alternative treatment for T2D is needed.

Chronic kidney disease (CKD) is characterized by the progressive loss of kidney function. Individuals who have CKD over time experience an increase in albuminuria, proteinuria, serum creatinine, and renal histopathological lesions. It eventually develops into end stage renal disease (ESRD) for many patients requiring either dialysis or kidney transplant. CKD may be caused by several underlying conditions including diabetes and hypertension known as diabetic nephropathy and hypertensive nephropathy, respectively. Diabetic nephropathy prevalence accounts for approximately 50% of kidney failures in the U.S. Hypertensive nephropathy prevalence accounts for nearly 25% of kidney failures in the U.S. The current standard of care for kidney diseases includes angiotensin converting enzyme (ACE) inhibitors and angiotensin II receptor blockers (ARBs). There remains a need for an alternative treatment for CKD.

Chen et al. (*Proceedings of the National Academy of Sciences* (PNAS), Oct. 31, 2006, vol. 103, NO:44, pp. 16580-16585) is an article entitled "Urocortin 2 modulates glucose utilization and insulin sensitivity in skeletal muscle." Further, in *Peptides* 27: 1806-1813 (2006), the authors disclose CRHR2 agonists including UCN2 analogs for the treatment of CRHR2 modulated disorders such as muscular atrophy. However, there is still a further need for novel therapeutic human UCN2 analogs that are agonists of CRHR2.

The present invention provides novel compounds that are CRHR2 agonists. The present invention also provides novel therapeutic CRHR2 agonists in the form of human UCN2 analogs which may be suitable for once weekly administration or other types of administration such as bi-monthly or monthly. The present invention also provides a novel compound that is a CRHR2 agonist for use in therapy, and in particular for use to treat T2D or CKD, or combinations thereof.

Accordingly, the present invention provides compounds which are urocortin molecules that have the amino acid sequence of Formula III:

wherein
$X_1$ denotes that the I residue is unmodified or is modified at the N-terminus by either acetylation or methylation,
$X_2$ is L or T,
$X_3$ is L or I,
$X_4$ is Q, R, or E,
$X_7$ is T or E,
$X_8$ is Q, H or R (SEQ ID NO:67), and
Formula III further comprises a modified K residue ("K*") substituted at position 10 or at any one position between position 14 and position 30 inclusive,
K* is modified by having the epsilon amino group of the K-side chain bound to a group of the formula —$X_5$—$X_6$, wherein $X_5$ is selected from the group consisting of between one to four amino acid residues, between one to four ([2-(2-Amino-ethoxy)-ethoxy]-acetyl moieties, and combinations of one to four amino acid residues and one to four ([2-(2-Amino-ethoxy)-ethoxy]-acetyl moieties, and $X_6$ is a $C_{14}$-$C_{24}$ fatty acid.

The present invention provides pharmaceutical compositions comprising a compound of Formula III with the modified K residue, or a pharmaceutically acceptable salt thereof (for example, trifluoroacetate salts, acetate salts, or hydrochloride salts). In some embodiments, the terminal amino acid is amidated as a C-terminal primary amide. In further embodiments, the pharmaceutical composition may include more pharmaceutically acceptable carriers, diluents, and excipients.

As noted above, the synthetic molecules of Formula III are constructed such that the modified K residue is substituted at position 10 or at any one position between position 14 and position 30 inclusive. For example, if the modified K residue is substituted at position 10, then the G residue that normally occupies position 10 is replaced with the modified K residue, such that these synthetic molecules would have the following formula:

X₁IVX₂SLDVPIK*LLQILX₃EQEKQEKEKQQATX₇NAX₄I-LAX₈V-NH₂ wherein K* is the modified K residue and $X_1$, $X_2$, $X_3$, $X_4$, $X_7$ and $X_8$ have the values and features described herein.

If the modified K residue is substituted at position 14, then the I residue that normally occupies position 14 is replaced with the modified K residue, such that these synthetic molecules would have the following formula:

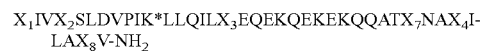

wherein K* is the modified K residue and $X_1$, $X_2$, $X_3$, $X_4$, $X_7$ and $X_8$ have the values and features described herein.

If the modified K residue is substituted at position 15, then the L residue that normally occupies position 15 is replaced with the modified K residue, such that these synthetic molecules would have the following formula:

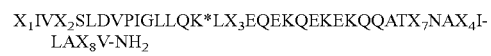

wherein K* is the modified K residue and $X_1$, $X_2$, $X_3$, $X_4$, $X_7$ and $X_8$ have the values and features described herein.

If the modified K residue is substituted at position 16, then the $X_3$ residue that normally occupies position 16 is replaced with the modified K residue, such that these synthetic molecules would have the following formula:

$$X_1IVX_2SLDVPIGLLQILK^*EQEKQEKEKQQATX_7NAX_4ILAX_8V\text{-}NH_2$$

wherein K* is the modified K residue and $X_1$, $X_2$, $X_4$, $X_7$ and $X_8$ have the values and features described herein.

If the modified K residue is substituted at position 17, then the E residue that normally occupies position 17 is replaced with the modified K residue, such that these synthetic molecules would have the following formula:

$$X_1IVX_2SLDVPIGLLQILX_3K^*QEKQEKEKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 18, then the Q residue that normally occupies position 18 is replaced with the modified K residue, such that these synthetic molecules would have the following formula:

$$X_1IVX_2SLDVPIGLLQILX_3EK^*EKQEKEKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 19, then the E residue that normally occupies position 19 is replaced with the modified K residue, such that these synthetic molecules would have the following formula:

$$X_1IVX_2SLDVPIGLLQILX_3EQK^*KQEKEKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 20, then the K residue that normally occupies position 20 is replaced with the modified K residue, such that these synthetic molecules would have the following formula:

$$X_1IVX_2SLDVPIGLLQILX_3EQEK^*QEKEKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 21, then the Q residue that normally occupies position 21 is replaced with the modified K residue, such that these synthetic molecules would have the following formula:

$$X_1IVX_2SLDVPIGLLQILX_3EQEKK^*EKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 22, then the E residue that normally occupies position 22 is replaced with the modified K residue, such that these synthetic molecules would have the following formula:

$$X_1IVX_2SLDVPIGLLQILX_3EQEKQK^*KEKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 23, then the K residue that normally occupies position 23 is replaced with the modified K residue, such that these synthetic molecules would have the following formula:

$$X_1IVX_2SLDVPIGLLQILX_3EQEKQEK^*EKQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 24, then the E residue that normally occupies position 24 is replaced with the modified K residue, such that these synthetic molecules would have the following formula:

$$X_1IVX_2SLDVPIGLLQILX_3EQEKQEKK^*KQQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 25, then the K residue that normally occupies position 25 is replaced with the modified K residue, such that these synthetic molecules would have the following formula:

$$X_1IVX_2SLDVPIGLLQILX_3EQEKQEKEK^*QQATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 26, then the Q residue that normally occupies position 26 is replaced with the modified K residue, such that these synthetic molecules would have the following formula:

$$X_1IVX_2SLDVPIGLLQILX_3EQEKQEKEKK^*QATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 27, then the Q residue that normally occupies position 27 is replaced with the modified K residue, such that these synthetic molecules would have the following formula:

$$X_1IVX_2SLDVPIGLLQILX_3EQEKQEKEKQK^*ATX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 28, then the A residue that normally occupies position 28 is replaced with the modified K residue, such that these synthetic molecules would have the following formula:

$$X_1IVX_2SLDVPIGLLQILX_3EQEKQEKEKQQK^*TX_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 29, then the T residue that normally occupies position 29 is replaced with the modified K residue, such that these synthetic molecules would have the following formula:

$$X_1IVX_2SLDVPIGLLQILX_3EQEKQEKEKQQAK^*X_7NAX_4ILAX_8V\text{-}NH_2$$

wherein K* is the modified K residue and $X_1$, $X_2$, $X_3$, $X_4$, $X_7$ and $X_8$ have the values and features described herein.

If the modified K residue is substituted at position 30, then the $X_7$ residue that normally occupies position 30 is replaced with the modified K residue, such that these synthetic molecules would have the following formula:

$$X_1IVX_2SLDVPIGLLQILX_3EQEKQEKEKQQATK^*NAX_4ILAX_8V\text{-}NH_2$$

wherein K* is the modified K residue and $X_1$, $X_2$, $X_3$, $X_4$, and $X_8$ have the values and features described herein.

As noted above, the $X_8$ of Formula III may be Q, H, or R. However, in some of the presently preferred embodiments, the $X_8$ group will be either an H or Q. Further preferred embodiments may have the $X_2$ and/or the $X_3$ of Formula III be an L residue. In yet additional preferred embodiments, the $X_4$ of Formula III may be a Q residue and/or the $X_7$ of Formula III is an T residue.

In other presently preferred embodiments, the $X_5$ of Formula III may comprise between 0-2 ([2-(2-Amino-ethoxy)-ethoxy]-acetyl moieties and, more preferably, 1 or 2 amino acid residues. In other presently preferred embodiments, the $X_5$ of Formula III may comprise two amino acid residues and two ([2-(2-Amino-ethoxy)-ethoxy]-acetyl moieties, wherein the two amino acid residues are either E or γE residues. In some embodiments, $X_5$ comprises only amino acid residues such that there are no ([2-(2-Amino-ethoxy)-ethoxy]-acetyl moieties. In yet additional presently preferred embodiments, the $X_1$ of Formula III will have the I residue at position 1 modified (at the N-terminus) by either acetylation or methylation.

As noted above, the amino acid sequence of Formula III is modified such that a modified K residue is substituted at position 10 or at any one position between position 14 and position 30 inclusive within the sequence. Some of the most preferred embodiments of Formula III have the modified K residue ("K*") substituted into position 29 and have $X_8$ be Q and $X_7$ be T. These molecules, which are subset of Formula III, are represented below as Formula I:

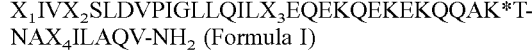

(As with the embodiments of Formula III, the embodiments of Formula I are designed such that $X_2$ can be L or T, and $X_3$ can be L or I, $X_4$ can be Q, R, or E (and more preferably Q or E), and $X_1$ can mean that the I residue at position 1 is, at its N-terminus, unmodified or is modified by either acetylation or methylation.) In some of the preferred embodiments of Formula I, the $X_1$ will have the I residue at position 1 modified at the N-terminus by either acetylation or methylation. In the embodiments of Formula I, the modified K residue at position 29 is modified with a fatty acid side chain that is conjugated to the epsilon-amino group of the K side chain, wherein the fatty acid side chain has a formula: ([2-(2-Amino-ethoxy)-ethoxy]-acetyl)$_2$-(γE)$_2$-CO—(CH$_2$)$_x$—CO$_2$H where x is 16 or 18. (Stated differently, in some of the presently preferred embodiments of Formula I, the $X_5$ and $X_6$ groups of Formula III have the following formula: ([2-(2-Amino-ethoxy)-ethoxy]-acetyl)$_2$-(γE)$_2$-CO—(CH$_2$)$_x$—CO$_2$H where x is 16 or 18) (SEQ ID NO:8). Of course, as noted above, the compound and molecules of Formula I may be made into pharmaceutically acceptable salts thereof.

The present invention also provides a pharmaceutical composition comprising a compound of Formula I, or a pharmaceutically acceptable salt thereof (for example, trifluoroacetate salts, acetate salts, or hydrochloride salts). In some embodiments, the terminal amino acid is amidated as a C-terminal primary amide. In further embodiments, the pharmaceutical composition may include more pharmaceutically acceptable carriers, diluents, and excipients.

In one embodiment, the compound or pharmaceutically acceptable salt of Formula I is designed such that $X_1$ has the N-terminus of the I residue modified by acetylation; $X_2$ is L; $X_3$ is L; $X_4$ is Q; the K* at position 29 is chemically modified through conjugation to the epsilon-amino group of the K-side chain with ([2-(2-Amino-ethoxy)-ethoxy]-acetyl)$_2$-(γE)$_2$-CO—(CH$_2$)$_{16}$—CO$_2$H; and the C-terminal amino acid is amidated as a C-terminal primary amide (SEQ ID NO:1).

In another embodiment, the compound or pharmaceutically acceptable salt of Formula I is designed such that $X_1$ has the N-terminus of the I residue modified by acetylation; $X_2$ is L; $X_3$ is L; $X_4$ is Q; the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO:2).

In another embodiment, the compound or pharmaceutically acceptable salt of Formula I is designed such that $X_1$ has the N-terminus of the I residue modified by methylation; $X_2$ is L; $X_3$ is L; $X_4$ is Q; the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{16}$—CO$_2$H; and the C-terminal amino acid is amidated as a C-terminal primary amide (SEQ ID NO:3).

In another embodiment, the compound or pharmaceutically acceptable salt of Formula I is designed such that $X_1$ has the N-terminus of the I residue modified by methylation; $X_2$ is L; $X_3$ is L; $X_4$ is Q; the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO:4).

In another embodiment, the compound or pharmaceutically acceptable salt of Formula I is designed such that $X_1$ has the N-terminus of the I residue modified by methylation; $X_2$ is T; $X_3$ is L; $X_4$ is E; the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO:5).

In another embodiment, the compound or pharmaceutically acceptable salt of Formula I is designed such that $X_1$ has the N-terminus of the I residue modified by methylation; $X_2$ is L; $X_3$ is L; $X_4$ is E; the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO:6).

In another embodiment, the compound or pharmaceutically acceptable salt of Formula I is designed such that $X_1$ has the N-terminus of the I residue modified by methylation; $X_2$ is T; $X_3$ is I; $X_4$ is E; the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO:7).

Further preferred embodiments of the present invention (which likewise fall within the scope of Formula III) may be designed in which the modified K residue ("K*") is substituted at position 29 and $X_5$ is Q, $X_7$ is T. Such preferred molecules and compounds (which are subset of Formula III) can be represented as Formula II:

 (Formula II)

(As with the embodiments of Formula III, the embodiments of Formula II are designed such that $X_2$ can be L or T, and $X_3$ can be L or I, $X_4$ can be Q, R, or E, and $X_1$ can mean that the I residue at position 1 is, at its N-terminus, unmodified or is modified by either acetylation or methylation.) However, further preferred embodiments of Formula II may be designed in which the $X_1$ is restricted such that the I residue (at position 1) is modified by either acetylation or methylation at the N-terminus and $X_4$ is restricted to being either Q or E.

In the embodiments of Formula II, the modified K residue ("K*") at position 29 is modified through conjugation to the epsilon-amino group of the K-side chain with a group of the formula —$X_5$—$X_6$, wherein
$X_5$ is selected from the group consisting of:
one to four amino acids;
one to four ([2-(2-Amino-ethoxy)-ethoxy]-acetyl) moieties; and
combinations of one to four amino acids and one to four ([2-(2-Amino-ethoxy)-ethoxy]-acetyl) moieties;
$X_6$ is a $C_{14}$-$C_{24}$ fatty acid (SEQ ID NO:16), or a pharmaceutically acceptable salt thereof.

In the embodiments of Formula 1 described herein, the modified K residue used in Formula I has the epsilon-amino group of the K side chain conjugated to the following group: ([2-(2-Amino-ethoxy)-ethoxy]-acetyl)$_2$-(γE)$_2$-CO—(CH$_2$)$_x$—CO$_2$H where x is 16 or 18. (Stated differently, in some of the presently preferred embodiments of Formula I, the $X_5$ and $X_6$ groups of Formula III have the following formula: ([2-(2-Amino-ethoxy)-ethoxy]-acetyl)$_2$-(γE)$_2$-CO—(CH$_2$)$_x$—CO$_2$H where x is 16 or 18).

Yet, as noted above, the compounds of Formula II and Formula III may use different groups for $X_5$ and $X_6$. For example, in some embodiments of Formula II and Formula III, $X_5$ may be one or four E or γE amino acid residues. Further embodiments Formula II and Formula III may have $X_5$ be two to four E or γE. Still further preferred embodiments Formula II and Formula III are constructed in which $X_5$ comprises two γE amino acids. In some embodiments of Formula II and Formula III, the $X_5$ group may comprise only amino acid residues; however, in other embodiments, the $X_5$ group may comprise one to four amino acid residues (such as, for example E or γE amino acids) used in combination with one to four ([2-(2-Amino-ethoxy)-ethoxy]-acetyl) moieties. Specifically, in other embodiments, $X_5$ constitutes combinations of one to four E or γE amino acids and one to four ([2-(2-Amino-ethoxy)-ethoxy]-acetyl) moieties. Additional embodiments are designed in which $X_5$ is combinations of two to four γE amino acids and one to four ([2-(2-Amino-ethoxy)-ethoxy]-acetyl) moieties (such as, for example two of the ([2-(2-Amino-ethoxy)-ethoxy]-acetyl) moieties). Other embodiments have $X_5$ be combinations of two γE amino acids and two ([2-(2-Amino-ethoxy)-ethoxy]-acetyl) moieties.

In one preferred embodiment of Formulas III and III, the group of the formula —$X_5$—$X_6$ is ([2-(2-Amino-ethoxy)-ethoxy]-acetyl)$_2$-(γE)$_2$-CO—(CH$_2$)$_x$—CO$_2$H, where x is 16 or 18. In other embodiments of Formulas III and III, the $X_5$ group may comprise at least one ([2-(2-Amino-ethoxy)-ethoxy]-acetyl moiety, with or without any amino acid residues. Further preferred embodiments of Formulas III and III are constructed in which the $X_5$ group comprises one or two ([2-(2-Amino-ethoxy)-ethoxy]-acetyl) moieties. In some embodiments the $X_6$ group is a straight chain fatty acid side chain of the formula CO—(CH$_2$)$_x$—CO$_2$H, wherein x is 16, 18, or 20. Most preferable embodiments have x being either 16 or 18.

As noted above, the compounds (or pharmaceutically acceptable salts thereof) of Formulas II and III have an $X_6$ group that is a $C_{14}$ to $C_{24}$ fatty acid. This $C_{14}$-$C_{24}$ fatty acid may be a saturated monoacid or a saturated diacid. Preferably, the fatty acid is a saturated monoacid or saturated diacid selected from the group consisting of myristic acid (tetradecanoic acid)($C_{14}$ monoacid), tetradecanedioic acid ($C_{14}$ diacid), palmitic acid (hexadecanoic acid)($C_{16}$ monoacid), hexadecanedioic acid ($C_{16}$ diacid), margaric acid (heptadecanoic acid)($C_{17}$ monoacid), heptadecanedioic acid ($C_{17}$ diacid), stearic acid (octadecanoic acid)($C_{18}$ monoacid), octadecanedioic acid ($C_{18}$ diacid), nonadecylic acid (nonadecanoic acid)($C_{19}$ monoacid), nonadecanedioic acid ($C_{19}$ diacid), arachadic acid (eicosanoic acid) ($C_{20}$ monoacid), eicosanedioic acid ($C_{20}$ diacid), heneicosylic acid (heneicosanoic acid) ($C_{21}$ monoacid), heneicosanedioic acid ($C_{21}$ diacid), behenic acid (docosanoic acid) ($C_{22}$ monoacid), docosanedioic acid ($C_{22}$ diacid), lignoceric acid (tetracosanoic acid)($C_{24}$ monoacid) and tetracosanedioic acid ($C_{24}$ diacid). The most preferable acids are the following: myristic acid, tetradecanedioic acid, palmitic acid, hexadecanedioic acid, stearic acid, octadecanedioic acid, nonadecanedioic acid, arachadic acid, eicosanedioic acid or docosanedioic acid.

The present invention of Formula I or Formula II or Formula III provides a pharmaceutical composition comprising a compound of Formula I or Formula II or Formula III, or a pharmaceutically acceptable salt thereof (for example, trifluoroacetate salts, acetate salts, or hydrochloride salts among others). In other embodiments, any salt or free base suitable for human use may be made using the compounds of Formula I or Formula II or Formula III. In some preferred embodiments, a peptide acetate salt of the compounds of Formula I or Formula II or Formula III is used. In some embodiments, the C-terminal amino acid is amidated as a C-terminal primary amide. In further embodiments, the pharmaceutical composition may include more pharmaceutically acceptable carriers, diluents, and excipients.

The present invention provides a pharmaceutical composition comprising a compound of Formula I or Formula II or Formula III, or a pharmaceutically acceptable salt thereof, and one or more pharmaceutically acceptable carriers, diluents, or excipients. The present invention also provides a pharmaceutical composition comprising a compound of Formula I or Formula II or Formula III, or a pharmaceutically acceptable salt thereof, in combination with an additional active ingredient.

The present invention provides a method for treatment of type II diabetes in a patient comprising administering to a patient in need of such treatment an effective amount of a compound of Formula I or Formula II or Formula III, or a pharmaceutically acceptable salt thereof. The present invention also provides a method for treatment of type II diabetes in a patient comprising administering to a patient in need of such treatment an effective amount of a compound of Formula I or Formula II or Formula III, or a pharmaceutically acceptable salt thereof, wherein the administration is subcutaneous. The present invention also provides a method of treatment of type II diabetes in a patient comprising administering to a patient in need of such treatment an effective amount of a compound of Formula I or Formula II or Formula III, or a pharmaceutically acceptable salt thereof, and simultaneously or sequentially an effective amount of one or more other active ingredients. In one embodiment, the other active ingredient is a currently available oral glucose lowering drug selected from a class of drugs that is considered prior to administration the standard of care as determined by industry guidelines such as the American Diabetes Association. Examples of current standard of care include metformin, thiazolidinediones (TZDs), sulfonylureas (SUs), dipeptidyl peptidase4 (DPP-IV) inhibitors, and sodium glucose co-transporters (SGLTs). In a further embodiment of the present invention, a method of treatment of type II diabetes in a patient as defined above is combined with diet and exercise.

Furthermore, the present invention provides a method for treatment of chronic kidney disease in a patient comprising administering to a patient in need of such treatment an effective amount of a compound of Formula I or Formula II or Formula III, or a pharmaceutically acceptable salt thereof. The present invention also provides a method for treatment of chronic kidney disease in a patient comprising administering to a patient in need of such treatment an effective amount of a compound of Formula I or Formula II or Formula III, or a pharmaceutically acceptable salt thereof, wherein the chronic kidney disease is caused by diabetic nephropathy. The present invention also provides a method for treatment of chronic kidney disease in a patient comprising administering to a patient in need of such treatment an effective amount of a compound of Formula I or Formula II or Formula III, or a pharmaceutically acceptable salt thereof, wherein the chronic kidney disease is caused by hypertensive nephropathy. The present invention also provides a method for treatment of chronic kidney disease in a patient comprising administering to a patient in need of such treatment an effective amount of a compound of Formula I or Formula II or Formula III, or a pharmaceutically acceptable salt thereof, wherein the administration is subcutaneous. The present invention also provides a method of treatment of chronic kidney disease in a patient comprising administering to a patient in need of such treatment an effective amount of a compound of Formula I, or a pharmaceutically acceptable salt thereof, and simultaneously or sequentially an effective amount of one or more other active ingredients. In one embodiment, the other active ingredient is selected from currently available oral ACE inhibitors or ARBs that are considered prior to administration the standard of care as determined by industry guidelines. Examples of current standard of care are ACEs inhibitors lisinopril and captopril and ARBs losartan and irbesartan.

Moreover, the present invention provides a compound of Formula I or Formula II or Formula III, or a pharmaceutically acceptable salt thereof, for use in therapy. The present invention also provides a compound of Formula I or Formula II or Formula III, or a pharmaceutically acceptable salt thereof, for use in the treatment of type II diabetes. Furthermore, the present invention provides of Formula I or Formula II or Formula III, or a pharmaceutically acceptable salt thereof, for use in the treatment of chronic kidney disease. The present invention provides a compound of Formula I or Formula II or Formula III, or a pharmaceutically acceptable salt thereof, for use in the treatment of chronic kidney disease caused by diabetic nephropathy or hypertensive nephropathy. The present invention provides the use of a compound of Formula I or Formula II or Formula III, or a pharmaceutically acceptable salt thereof, for the manufacture of a medicament for the treatment of type II diabetes and/or chronic kidney disease.

The present invention also encompasses novel intermediates and processes for the synthesis of the compounds of Formula I or Formula II or Formula III.

The compounds of Formula I or Formula II or Formula III or a pharmaceutically salt thereof are particularly useful in the treatment methods of the invention.

The peptide chain of the compounds of the present invention can be synthesized using standard manual or automated solid-phase synthesis procedures. Automated peptide synthesizers are commercially available from, for example, Applied Biosystems (Foster City, Calif.) and Protein Technologies Inc. (Tucson, Ariz.). Reagents for solid-phase synthesis are readily available from commercial sources. Solid-phase synthesizers can be used according to the manufacturer's instructions for blocking interfering groups, protecting amino acids during reaction, coupling, deprotecting, and capping of unreacted amino acids.

Typically, an N-α-carbamoyl protected amino acid and the N-terminal amino acid on the growing peptide chain attached to a resin are coupled at room temperature in an inert solvent such as dimethylformamide, N-methylpyrrolidone or methylene chloride in the presence of coupling agents such as diisopropyl-carbodiimide and 1-hydroxybenzotriazole. The Nα-carbamoyl protecting group is removed from the resulting peptide resin using a reagent such as trifluoroacetic acid (TFA) or piperidine, and the coupling reaction is repeated with the next desired Nα-protected amino acid to be added to the peptide chain. Suitable amine protecting groups are well known in the art and are described, for example, in Green and Wuts, "Protecting Groups in Organic Synthesis," John Wiley and Sons, 1991. The most commonly used examples include tBoc and fluorenylmethoxycarbonyl (Fmoc). After completion of synthesis, peptides are cleaved from the solid-phase support with simultaneous side-chain deprotection using standard treatment methods under acidic conditions.

The skilled artisan will appreciate that the peptide chain of the compounds of the invention are synthesized with a C-terminal carboxamide. For the synthesis of C-terminal amide peptides, resins incorporating Rink amide MBHA or Rink amide AM linkers are typically used with Fmoc synthesis, while MBHA resin is generally used with tBoc synthesis.

Crude peptides typically are purified using RP-HPLC on C8 or C18 columns using water-acetonitrile gradients in 0.05 to 0.1% TFA. Purity can be verified by analytical RP-HPLC. Identity of peptides can be verified by mass spectrometry. Peptides can be solubilized in aqueous buffers over a wide pH range.

As used herein, the term "AUC" means area under the curve.

As used herein, the term "average molecular weight" indicates the average of the molecular weight of the different oligomer size components with a very narrow distribution and is determined by mass spectrometry techniques.

As used herein, the term "EC50" refers to the concentration of compound that results in 50% activation of the assay endpoint, e.g., cAMP.

As used herein, the term "ED50" refers to the concentration of compound that results in a 50% response in the in vivo assay endpoint, e.g., plasma or blood glucose.

As used herein, the term "effective amount" refers to the amount or dose of compound of the invention, or a pharmaceutically acceptable salt thereof which, upon single or multiple dose administration to the patient, provides the desired effect in the patient under diagnosis or treatment for a daily administration. An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, the term "patient" refers to a mammal, such as a mouse, guinea pig, rat, dog, cat, or human. It is understood that the preferred patient is a human.

As used herein, the term "treating" or "to treat" includes prohibiting, restraining, slowing, stopping, or reversing the progression or severity of an existing symptom or disorder.

When used herein, the term "in combination with" means administration of the synthetic molecule of the present invention either simultaneously, sequentially or in a single combined formulation with the one or more additional therapeutic agents.

Certain abbreviations are defined as follows: "ACR" refers to urine albumin/urine creatinine ratio; "amu" refers to atomic mass unit; "Boc" refers to tert-butoxycarbonyl; "cAMP" refers to cyclic adenosine monophosphate; "DMSO" refers to dimethyl sulfoxide; "EIA/RIA" refers to enzyme immunoassay/radioimmunoassay; "hr" refers to hour; "HTRF" refers to homogenous time-resolved fluorescent; "i.v." refers to intravenous; "kDa" refers to kilodaltons; "LC-MS" refers to liquid chromatography-mass spectrometry; "MS" refers to mass spectrometry; "OtBu" refers to O-tert-butyl; "Pbf" refers to $N^G$-2,2,4,6,7-pentamethyldihydrobenzofuran-5-sulfonyl; "RP-HPLC" refers to reversed-phase high performance liquid chromatography; "s.c." refers to subcutaneous; "SEM" refers to standard error of the mean; "TFA" refers to trifluoroacetic acid; and "Trt" refers to Trityl. Standard one-letter codes are used to represent the amino acid in the compounds of Formula I. All amino acids used in the Formula I are L-amino acids. Standard three-letter codes may also be used to represent amino acids.

The compounds of the present invention utilize a $C_{14}$-$C_{24}$ fatty acid chemically conjugated to the epsilon-amino group of a lysine side-chain either by a direct bond or by a linker. The term "$C_{14}$-$C_{24}$ fatty acid" as used herein means a carboxylic acid with between 14 and 24 carbon atoms. The $C_{14}$-$C_{24}$ fatty acid suitable for use herein can be a saturated monoacid or a saturated diacid. By "saturated" is meant that the fatty acid contains no carbon-carbon double or triple bonds.

Examples of specific saturated $C_{14}$-$C_{24}$ fatty acids that are suitable for the compounds and uses thereof disclosed herein include, but are not limited to, myristic acid (tetradecanoic acid)($C_{14}$ monoacid), tetradecanedioic acid ($C_{14}$ diacid), palmitic acid (hexadecanoic acid) ($C_{16}$ monoacid), hexadecanedioic acid ($C_{16}$ diacid), margaric acid (heptadecanoic acid)($C_{17}$ monoacid), heptadecanedioic acid ($C_{17}$ diacid), stearic acid (octadecanoic acid)($C_{18}$ monoacid), octadecanedioic acid ($C_{18}$ diacid), nonadecylic acid (nonadecanoic acid)($C_{19}$ monoacid), nonadecanedioic acid ($C_{19}$ diacid), arachadic acid (eicosanoic acid)($C_{20}$ monoacid), eicosanedioic acid ($C_{20}$ diacid), heneicosylic acid (heneicosanoic acid)($C_{21}$ monoacid), heneicosanedioic acid ($C_{21}$ diacid), behenic acid (docosanoic acid)($C_{22}$ monoacid), docosanedioic acid ($C_{22}$ diacid), lignoceric acid (tetracosanoic acid) ($C_{24}$ monoacid), tetracosanedioic acid ($C_{24}$ diacid), including branched and substituted derivatives thereof.

In preferred aspects of the compounds of the present invention, the $C_{14}$-$C_{24}$ fatty acid is selected from the group consisting of a saturated $C_{14}$ monoacid, a saturated $C_{14}$ diacid, a saturated $C_{16}$ monoacid, a saturated $C_{16}$ diacid, a saturated $C_{18}$ monoacid, a saturated $C_{18}$ diacid, a saturated $C_{19}$ diacid, a saturated $C_{20}$ monoacid, a saturated $C_{20}$ diacid, a saturated $C_{22}$ diacid, and branched and substituted derivatives thereof. In more preferred aspects of the compounds of the present invention, the $C_{14}$-$C_{24}$ fatty acid is selected from the group consisting of myristic acid, tetradecanedioic acid, palmitic acid, hexadecanedioic acid, stearic acid, octadecanedioic acid, nonadecanedioic acid, arachadic acid, eicosanedioic acid and docosanedioic acid. Preferably, the $C_{14}$-$C_{24}$ fatty acid is octadecanedioic acid or eicosanedioic acid.

The length and composition of the fatty acid impacts the half-life of the compound, the potency of the compound in in vivo animal models and also impacts the solubility and stability of the compound. Conjugation of the peptide defined herein to a $C_{14}$-$C_{24}$ saturated fatty monoacid or diacid results in compounds that exhibit desirable half-life, desirable potency in in vivo animal models and also possess desired solubility and stability characteristics.

The compounds of the invention are preferably formulated as pharmaceutical compositions administered by parenteral routes (e.g., subcutaneous, intravenous, intraperitoneal, intramuscular, or transdermal). Such pharmaceutical compositions and processes for preparing same are well known in the art. (See, e.g., Remington: The Science and Practice of Pharmacy, L. V. Allen, Editor, $22^{nd}$ Edition, Pharmaceutical Press, 2012). The preferred route of administration is subcutaneous.

The compounds of the present invention may react with any of a number of inorganic and organic acids to form pharmaceutically acceptable acid addition salts. Pharmaceutically acceptable salts and common methodology for preparing them are well known in the art. See, e.g., P. Stahl, et al. Handbook of Pharmaceutical Salts: Properties, Selection and Use, 2nd Revised Edition (Wiley-VCH, 2011); S. M. Berge, et al., "Pharmaceutical Salts," Journal of Pharmaceutical Sciences, Vol. 66, NO: 1, January 1977. Preferred pharmaceutically acceptable salt of the present invention are trifluoroacetate salts, acetate salts and hydrochloride salts among others.

The compounds of the present invention may be administered by a physician or self-administered using an injection. It is understood the gauge size and amount of injection volume is determined by the skilled practitioner. In one embodiment, the amount of injection volume is ≤2 ml, preferably ≤1 ml. Also a further embodiment is the use of a needle gauge ≥27, preferably ≥29.

The compounds of Formula I or Formula II or Formula III are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The present invention also encompasses novel intermediates and processes useful for the synthesis of compounds of Formula I or Formula II or Formula III, or a pharmaceutically acceptable salt thereof. The intermediates and compounds of the present invention may be prepared by a variety of procedures known in the art including via both chemical synthesis and recombinant technology. In particular, the process using chemical synthesis is illustrated in the Preparation(s) and Example(s) below. The specific synthetic steps for each of the routes described may be combined in different ways to prepare compounds of Formula I, or salts thereof. The reagents and starting materials are readily available to one of ordinary skill in the art. It is understood that these Preparation(s) and Example(s) are not intended to be limiting to the scope of the invention in any way.

EXAMPLE 1

wherein the $X_1$ at position 1 is I that is modified, at the N terminus, by acetylation; $X_2$ is L; $X_3$ is L; $X_4$ is Q; and the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{16}$—CO$_2$H; and the C-terminal amino acid is amidated as a C-terminal primary amide (SEQ ID NO: 1). The structure of this sequence is shown below.

Pd(PPh$_3$)$_4$ in the presence of PhSiH$_3$ as a scavenger. Additional coupling/deprotection cycles using a Fmoc/t-Bu strategy to extend the K at position 29 side-chain involved Fmoc-NH-PEG$_2$-CH$_2$COOH (ChemPep Catalog #280102), Fmoc-Glu(OH)-OtBu (ChemPep Catalog #100703) and HOOC—(CH$_2$)$_{16}$—COOtBu. In all couplings, 3 equivalents of the building block are used with PyBOP (3 equiv) and DIEA (6 equiv) in DMF for 4 h at 25° C.

Concomitant cleavage from the resin and side chain protecting group removal are carried out in a solution containing trifluoroacetic acid (TFA):triisopropylsilane:1,2-ethanedithiol:methanol:thioanisole 80:5:5:5:5 (v/v) for 2 h at 25° C. followed by precipitation with cold ether. Crude

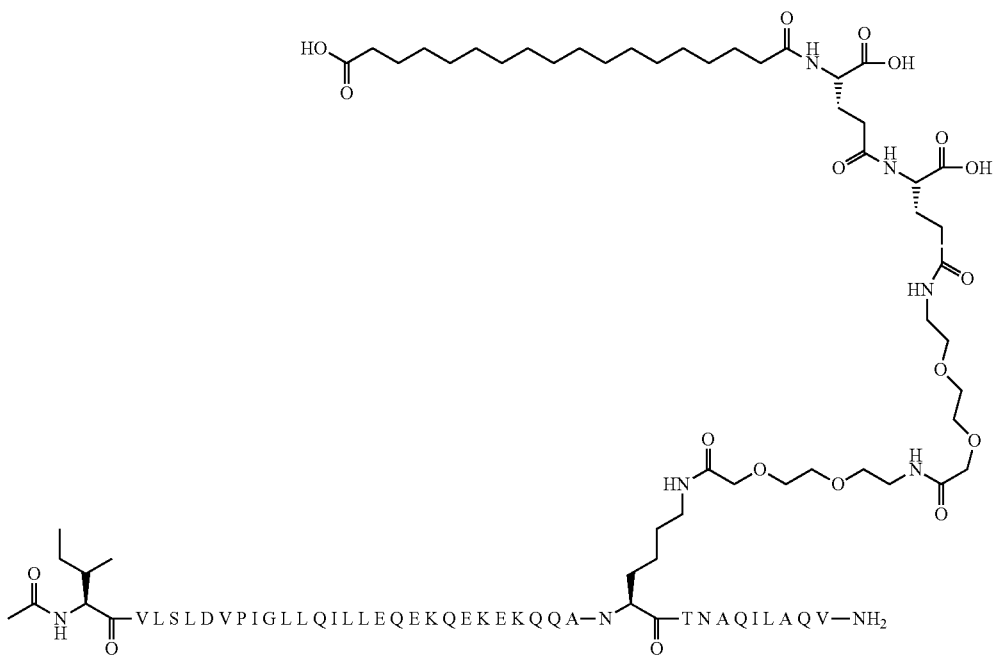

The structure of this sequence contains the standard single letter amino acid code with exception of residues I at position 1, and K at position 29 where the structures of these amino acid residues have been expanded.

The peptide according to SEQ ID NO: 1 of the present invention is generated by solid-phase peptide synthesis using a Fmoc/t-Bu strategy carried out on a Symphony automated peptide synthesizer (PTI Protein Technologies Inc.) starting from RAPP AM-Rink Amide resin (H40023 Polystyrene AM RAM, Rapp polymere GmbH) and with couplings using 6 equivalents of amino acid activated with diisopropylcarbodiimide (DIC) and Oxyma pure (1:1:1 molar ratio) in dimethylformamide (DMF) for 3 h at 25° C.

Extended coupling for Thr30 (10 h) is necessary to improve the quality of the crude peptide. A Fmoc-Lys (Alloc)-OH building block is used for K at position 29 coupling (orthogonal protecting group) to allow for site specific attachment of the fatty acid moiety later on in the synthetic process. The N-terminal residue (I at position 1) is acetylated using 10 equivalents of acetic acid with diisopropylcarbodiimide (DIC) and Oxyma pure (1:1:1 molar ratio) in dimethylformamide (DMF) for 1 h at 25° C.

After finishing the elongation of the peptide-resin described above, the Alloc protecting group present in the K at position 29 is removed using catalytic amounts of peptide is purified to >99% purity (15-20% purified yield) by reversed-phase HPLC chromatography with water/acetonitrile (containing 0.1% v/v TFA) gradient on a Phenyl hexyl column (phenomenex, 5 micron, 100 A), where suitable fractions are pooled and lyophilized.

In a synthesis performed essentially as described above, the purity of Example 1 was examined by analytical reversed-phase HPLC, and identity was confirmed using LC/MS (observed: M+3H$^+$/3=1718.8; Calculated M+3H$^+$/3=1720.0; observed: M+4H$^+$/4=1289.2; Calculated M+4H$^+$/4=1290.3; observed: M+5H$^+$/5=1031.5; Calculated M+5H$^+$/5=1032.4).

EXAMPLE 2

wherein the $X_1$ is I in which the N terminus is modified via acetylation; $X_2$ is L; $X_3$ is L; $X_4$ is Q; and the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO: 2). The structure of this sequence is shown below.

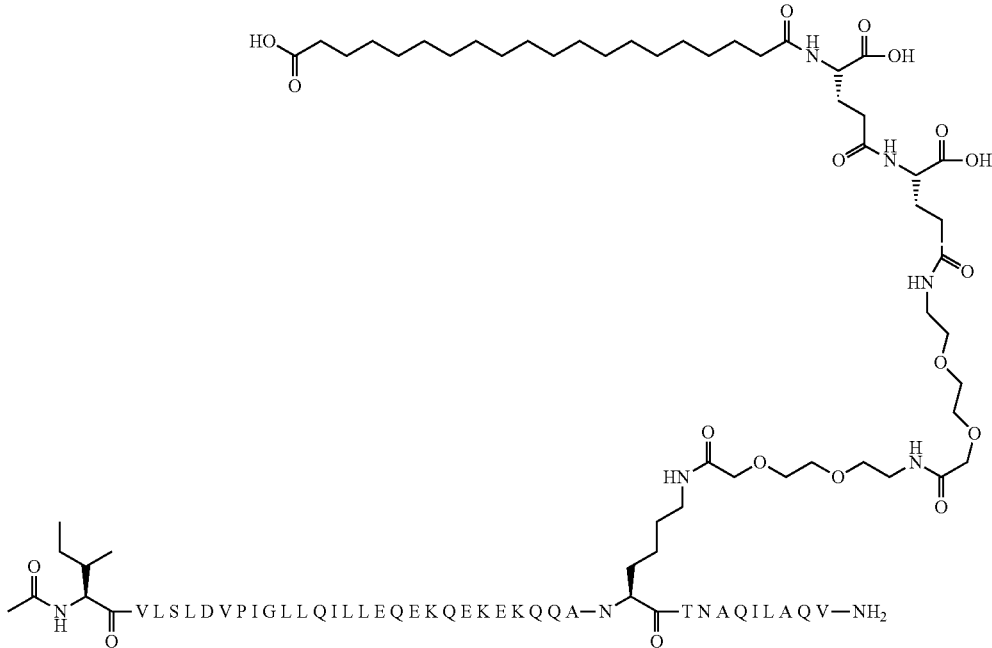

The structure of this sequence contains the standard single letter amino acid code with exception of residues I at position 1 and K at position 29 where the structures of these amino acid residues have been expanded.

The peptide according to SEQ ID NO: 2 of the present invention is synthesized similarly as described above in Example 1. HOOC—(CH$_2$)$_{18}$—COOtBu is incorporated using 3 equivalents of the building block with PyBOP (3 equiv) and DIEA (6 equiv) in DMF for 4 h at 25° C.

In a synthesis performed essentially as described above, the purity of Example 2 was examined by analytical reversed-phase HPLC, and identity was confirmed using LC/MS (observed: M+3H$^+$/3=1728.2; Calculated M+3H$^+$/3=1729.4; observed: M+4H$^+$/4=1296.3; Calculated M+4H$^+$/4=1297.3; observed: M+5H$^+$/5=1037.4; Calculated M+5H$^+$/5=1038.0).

EXAMPLE 3

X$_1$IVX$_2$SLDVPIGLLQILX$_3$EQEKQEKEKQQAK*TNAX$_4$ILAQV-NH2 wherein the X$_1$ is I in which the N terminus is modified via methylation; X$_2$ is L; X$_3$ is L; X$_4$ is Q; and the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{16}$—CO$_2$H; and the C-terminal amino acid is amidated as a C-terminal primary amide (SEQ ID NO: 3). The structure of this sequence is shown below.

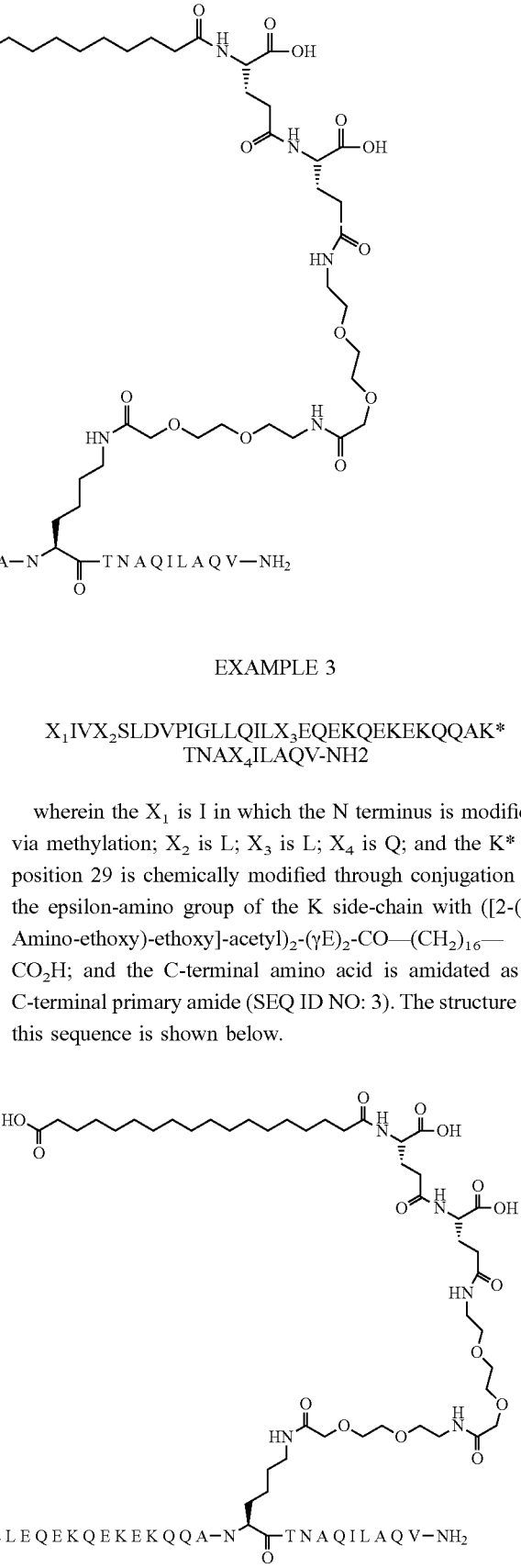

The structure of this sequence contains the standard single letter amino acid code with exception of residues N-methyl isoleucine at position 1 and K at position 29, where the structures of these amino acid residues have been expanded.

The compound according to SEQ ID NO: 3 of the present invention is synthesized similarly as described above for Example 1. The N-terminal residue (N-methyl isoleucine at position 1) is incorporated as Boc-NMeIle-OH using 6 equivalents of the building block with PyBOP (6 equiv) and DIEA (12 equiv) in DMF-DCM (1:1, v/v) for 15 h at 25° C.

In a synthesis performed essentially as described above, the purity of Example 3 was examined by analytical reversed-phase HPLC, and identity was confirmed using LC/MS (observed: $M+3H^+/3=1709.6$; Calculated $M+3H^+/3=1710.7$; observed: $M+4H^+/4=1282.2$; Calculated $M+4H^+/4=1283.3$; observed: $M+5H^+/5=1025.8$; Calculated $M+5H^+/5=1026.8$).

EXAMPLE 4

wherein $X_1$ is I in which the N terminus is modified via methylation; $X_2$ is L; $X_3$ is L; $X_4$ is Q; and the K* at position 29 is chemically modified through conjugation to the epsilon-amino group of the K side-chain with ([2-(2-Amino-ethoxy)-ethoxy]-acetyl)$_2$-($\gamma$E)$_2$-CO—(CH$_2$)$_{18}$—CO$_2$H; and the C-terminal amino acid is amidated as a C-terminal primary amide (SEQ ID NO: 4). The structure of this sequence is shown below.

The structure of this sequence contains the standard single letter amino acid code with exception of residues N-methyl Isoleucine at position 1 and K at position 29, where the structures of these amino acid residues have been expanded.

The compound according to SEQ ID NO: 4 of the present invention is synthesized similarly as described above for Example 1. The N-terminal residue (N-methyl Isoleucine at position 1) is incorporated as Boc-NMeIle-OH using 6 equivalents of the building block with PyBOP (6 equiv) and DIEA (12 equiv) in DMF-DCM (1:1, v/v) for 15 h at 25° C. HOOC—(CH$_2$)$_{18}$—COOtBu is incorporated using 3 equivalents of the building block with PyBOP (3 equiv) and DIEA (6 equiv) in DMF for 4 h at 25° C.

In a synthesis performed essentially as described above, the purity of Example 4 was examined by analytical reversed-phase HPLC, and identity was confirmed using LC/MS (observed: $M+3H^+/3=1719.4$; Calculated $M+3H^+/3=1720.1$; observed: $M+4H^+/4=1289.8$; Calculated $M+4H^+/4=1290.3$; observed: $M+5H^+/5=1031.8$; Calculated $M+5H^+/5=1032.4$).

EXAMPLE 5

wherein $X_1$ is I in which the N terminus is modified via methylation; $X_2$ is T; $X_3$ is L; $X_4$ is E; and the K* at position 29 is chemically modified through conjugation to the epsilon-amino group of the K side-chain with ([2-(2-Amino-ethoxy)-ethoxy]-acetyl)$_2$-($\gamma$E)$_2$-CO—(CH$_2$)$_{18}$—CO$_2$H; and the C-terminal amino acid is amidated as a C-terminal primary amide (SEQ ID NO: 5). The structure of this sequence is shown below.

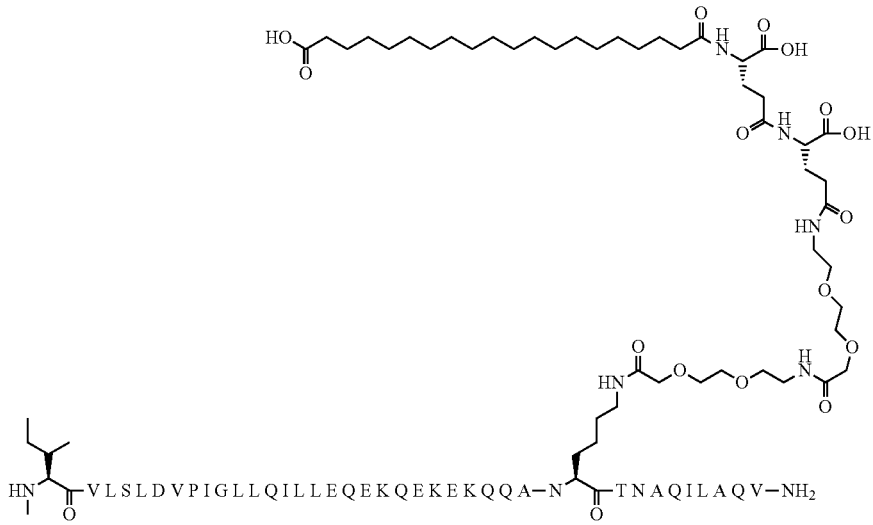

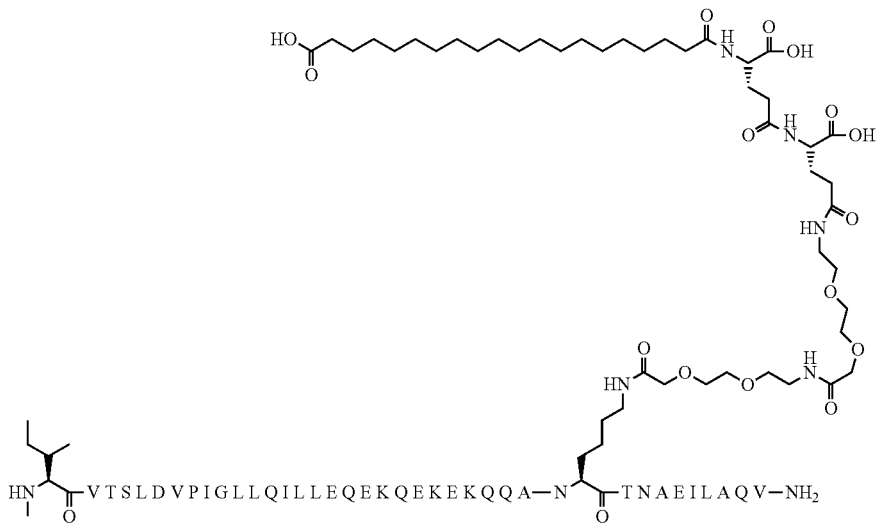

The structure of this sequence contains the standard single letter amino acid code with exception of residues N-methyl Isoleucine at position 1, and K at position 29 where the structures of these amino acid residues have been expanded.

The compound according to SEQ ID NO: 5 of the present invention is synthesized similarly as described above for Example 4.

In a synthesis performed essentially as described above, the purity of Example 5 was examined by analytical reversed-phase HPLC, and identity was confirmed using LC/MS (observed: $M+3H^+/3=1715.7$; Calculated $M+3H^+/3=1716.4$; observed: $M+4H^+/4=1287.0$; Calculated $M+4H^+/4=1287.5$; observed: $M+5H^+/5=1029.7$; Calculated $M+5H^+/5=1030.2$).

EXAMPLE 6

wherein $X_1$ is I in which the N terminus is modified via methylation; $X_2$ is L; $X_3$ is L; $X_4$ is E; and the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO: 6). The structure of this sequence is shown below.

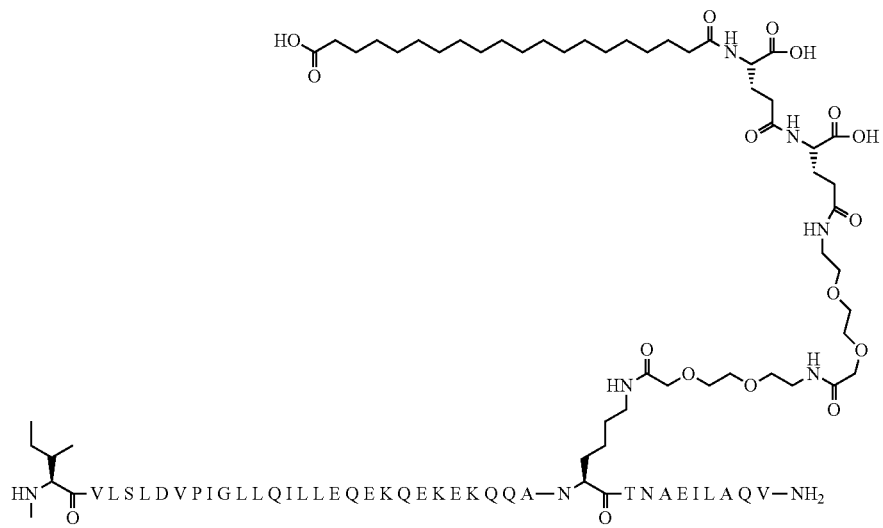

The structure of this sequence 6 contains the standard single letter amino acid code with exception of residues N-Methyl Isoleucine at position 1 and K at position 29 where the structures of these amino acid residues have been expanded.

The compound according to SEQ ID NO: 6 of the present invention is synthesized similarly as described above for Example 4.

In a synthesis performed essentially as described above, the purity of Example 6 was examined by analytical reversed-phase HPLC, and identity was confirmed using LC/MS (observed: M+3H$^+$/3=1719.7; Calculated M+3H$^+$/3=1720.4; observed: M+4H$^+$/4=1289.8; Calculated M+4H$^+$/4=1290.5; observed: M+5H$^+$/5=1032.2; Calculated M+5H$^+$/5=1032.6).

EXAMPLE 7

X$_1$IVX$_2$SLDVPIGLLQILX$_3$EQEKQEKEKQQAK*TNAX$_4$ILAQV-NH2 wherein X$_1$ is I in which the N terminus is modified via methylation; X$_2$ is T; X$_3$ is I; X$_4$ is E; and the K* at position 29 is chemically modified through conjugation to the epsilon-amino group of the K side-chain with ([2-(2-Amino-ethoxy)-ethoxy]-acetyl)$_2$-(γE)$_2$-CO—(CH$_2$)$_{18}$—CO$_2$H; and the C-terminal amino acid is amidated as a C-terminal primary amide (SEQ ID NO: 7). The structure of this sequence is shown below.

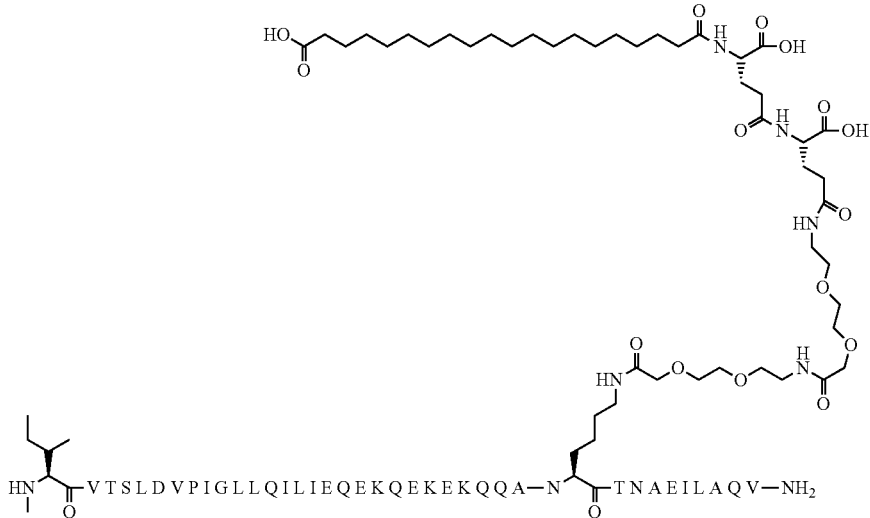

The structure of this sequence contains the standard single letter amino acid code with exception of residues N-methyl Isoleucine at position 1 and K at position 29, where the structures of these amino acid residues have been expanded.

The compound according to SEQ ID NO: 7 of the present invention is synthesized similarly as described above for Example 4.

In a synthesis performed essentially as described above, the purity of Example 7 was examined by analytical reversed-phase HPLC, and identity was confirmed using LC/MS (observed: M+3H$^+$/3=1715.6; Calculated M+3H$^+$/3=1716.4; observed: M+4H$^+$/4=1286.8; Calculated M+4H$^+$/4=1287.5; observed: M+5H$^+$/5=1029.8; Calculated M+5H$^+$/5=1030.2).

EXAMPLE 8

The following compounds of the present invention are synthesized similarly as described above for Example 4. The structures shown below contains the standard single letter amino acid code with exception of residues N-methylated I at position 1 and K at position 29 where the structures of these amino acid residues have been expanded.

X$_1$IVLSLDVPIGLLQILLEQEKQEKEKQQAK*TNAQILAQV-NH2 wherein X$_1$ has the N-terminus of the I residue modified by methylation;
wherein the K* at position 29 has been chemically modified with the following fatty acid side chain:
-γE-([2-(2-Amino-ethoxy)-ethoxy]-acetyl)$_2$-(γE)$_2$-CO—(CH$_2$)$_{18}$—COOH; and the C-terminal amino acid is amidated as a C-terminal primary amide (SEQ ID NO:9).

X$_1$IVLSLDVPIGLLQILLEQEKQEKEKQQAK*TNAQILAQV-NH2
wherein X$_1$ has the N-terminus of the I residue modified by methylation;
wherein the K* at position 29 has been chemically modified with the following fatty acid side chain:
-γE-([2-(2-Amino-ethoxy)-ethoxy]-acetyl)$_2$-(γE)$_2$-CO—(CH$_2$)$_{16}$—COOH;
and the C-terminal amino acid is amidated as a C-terminal primary amide (SEQ ID NO:10).

X$_1$IVLSLDVPIGLLQILLEQEKQEKEKQQAK*TNAQILAQV-NH2
wherein X$_1$ has the N-terminus of the I residue modified by methylation;
wherein the K* at position 29 has been chemically modified with the following fatty acid side chain:
-γE-γE-γE-γE-CO—(CH$_2$)$_{18}$—COOH;
and the C-terminal amino acid is amidated as a C-terminal primary amide (SEQ ID NO:11).

X$_1$IVLSLDVPIGLLQILLEQEKQEKEKQQAK*TNAQILAQV-NH2
wherein X$_1$ has the N-terminus of the I residue modified by methylation;
wherein the K* at position 29 has been chemically modified with the following fatty acid side chain:

-γE-γE-([2-(2-Amino-ethoxy)-ethoxy]-acetyl)-γE-γE-
CO—(CH$_2$)$_{18}$—COOH;
and the C-terminal amino acid is amidated as a C-terminal
primary amide (SEQ ID NO:12).

X$_1$IVLSLDVPIGLLQILLEQEKQEKEKQQAK*TNAQILAQV-NH2
wherein X$_1$ has the N-terminus of the I residue modified by methylation;
wherein the K* at position 29 has been chemically modified with the following fatty acid side chain:
-γE-γE-([2-(2-Amino-ethoxy)-ethoxy]-acetyl)$_2$-γE-γE-
CO—(CH$_2$)$_{18}$—COOH;
and the C-terminal amino acid is amidated as a C-terminal
primary amide (SEQ ID NO:13).

X$_1$IVLSLDVPIGLLQILLEQEKQEKEKQQAK*TNAQILAQV-NH2
wherein X$_1$ has the N-terminus of the I residue modified by methylation;
wherein the K* at position 29 has been chemically modified with the following fatty acid side chain:
-γE-([2-(2-Amino-ethoxy)-ethoxy]-acetyl)-γE-γE-
CO—(CH$_2$)$_{18}$—COOH;
and the C-terminal amino acid is amidated as a C-terminal
primary amide (SEQ ID NO:14).

EXAMPLE 9

The following compounds of the present invention are synthesized similarly as described above for Example 4. The structures shown below contains the standard single letter amino acid codes. All of the following compounds or synthetic molecules fall within the scope of Formula III. The purity of these compounds was tested by analytical reversed-phase HPLC, and identity was confirmed using LC/MS, in the manner outlined herein.

IVLSLDVPIGLLQK*LLEQEKQEKEKQQATTN-ARILARV-NH2
wherein the K* at position 14 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:21).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 14).

IVLSLDVPIGLLQIK*LEQEKQEKEKQQATTN-ARILARV-NH2
wherein the K* at position 15 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:22).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 15).

IVLSLDVPIGLLQILLK*QEKQEKEKQQATTNARILARV-NH2
wherein the K* at position 17 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:23).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 17).

IVLSLDVPIGLLQILLEQK*KQEKEKQQATTNA-RILARV-NH2
wherein the K* at position 19 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:24).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 19).

IVLSLDVPIGLLQILLEQEK*QEKEKQQATTNARILARV-NH2
wherein the K* at position 20 has been chemically such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:25).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 20).

IVLSLDVPIGLLQILLEQEKK*EKQQAT-TNARILARV-NH2
wherein the K* at position 21 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:26).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 21).

IVLSLDVPIGLLQILLEQEKQK*KEKQQATTNA-RILARV-NH2
wherein the K* at position 22 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:27).
This sequence falls within the scope of Formula III (in that, in this particular embodiment, X$_1$ is an unmodified I residue, X$_2$ is L, X$_3$ is L, X$_4$ is R, X$_7$ is T, X$_8$ is R, X$_5$ is one γE residue and X$_6$ is a C$_{16}$ mono fatty acid and the K* residue has replaced the original amino acid at position 22).

IVLSLDVPIGLLQILLEQEKQEK*EKQQATTNAR-ILARV-NH2
wherein the K* at position 23 has been chemically modified such that the epsilon-amino group of the K-side chain is bonded with a -γE-CO—(CH$_2$)$_{14}$—CH$_3$ group;
and the C-terminal amino acid is amidated as a C-terminal primary amide (SEQ ID NO:28).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 23).
IVLSLDVPIGLLQILLEQEKQEKK*KQQATTNARIL-ARV-NH2
 wherein the K* at position 24 has been chemically modified such that the epsilon-amino group of the K-side chain is bonded with a -γE-CO—$(CH_2)_{14}$—$CH_3$ group;
 and the C-terminal amino acid is amidated as a C-terminal primary amide (SEQ ID NO:29).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 24).
IVLSLDVPIGLLQILLEQEKQEKEK*QQATTNARIL-ARV-NH2
 wherein the K* at position 25 has been chemically modified such that the epsilon-amino group of the K-side chain is bonded with a -γE-CO—$(CH_2)_{14}$—$CH_3$ group;
 and the C-terminal amino acid is amidated as a C-terminal primary amide (SEQ ID NO:30).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 25).
IVLSLDVPIGLLQILLEQEKQEKEK*QQATTNARIL-ARV-NH2
 wherein the K* at position 25 has been chemically modified such that the epsilon-amino group of the K-side chain is bonded with a -γE-γE-CO—$(CH_2)_{14}$—$CH_3$ group;
 and the C-terminal amino acid is amidated as a C-terminal primary amide (SEQ ID NO:31).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is two γE residues and $X_6$ is a $C_{16}$ mono fatty acid and the K* residue has replaced the original amino acid at position 25).
IVLSLDVPIGLLQILLEQEKQEKEK*QQATTNARIL-ARV-NH2
 wherein the K* at position 25 has been chemically modified such that the epsilon-amino group of the K-side chain is bonded with a -([2-(2-Amino-ethoxy)-ethoxy]-acetyl)-γE-CO—$(CH_2)_{14}$—$CH_3$ group;
 and the C-terminal amino acid is amidated as a C-terminal primary amide (SEQ ID NO:32).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is a combination of one γE residue and one ([2-(2-Amino-ethoxy)-ethoxy]-acetyl) group and $X_6$ is a $C_{16}$ mono fatty acid and the K* residue has replaced the original amino acid at position 25).
IVLSLDVPIGLLQILLEQEKQEKEKK*QATTNAR-ILARV-NH2
 wherein the K* at position 26 has been chemically modified such that the epsilon-amino group of the K-side chain is bonded with a -γE-CO—$(CH_2)_{14}$—$CH_3$ group;
 and the C-terminal amino acid is amidated as a C-terminal primary amide (SEQ ID NO:33).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 26).
IVLSLDVPIGLLQILLEQEKQEKEKK*QATTNARIL-ARV-NH2
 wherein the K* at position 26 has been chemically modified such that the epsilon-amino group of the K-side chain is bonded with a -γE-γE-CO—$(CH_2)_{14}$—$CH_3$ group;
 and the C-terminal amino acid is amidated as a C-terminal primary amide (SEQ ID NO:34).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is two γE residues and $X_6$ is a $C_{16}$ mono fatty acid and the K* residue has replaced the original amino acid at position 26).
IVLSLDVPIGLLQILLEQEKQEKEKQK*ATTNAR-ILARV-NH2
 wherein the K* at position 27 has been chemically modified such that the epsilon-amino group of the K-side chain is bonded with a -γE-CO—$(CH_2)_{14}$—$CH_3$ group;
 and the C-terminal amino acid is amidated as a C-terminal primary amide (SEQ ID NO:35).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 27).
IVLSLDVPIGLLQILLEQEKQEKEKQQK*TTNAR-ILARV-NH2
 wherein the K* at position 28 has been chemically modified such that the epsilon-amino group of the K-side chain is bonded with a -γE-CO—$(CH_2)_{14}$—$CH_3$ group;
 and the C-terminal amino acid is amidated as a C-terminal primary amide (SEQ ID NO:36).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 28).
IVLSLDVPIGLLQILLEQEKQEKEKQQAK*TNA-RILARV-NH2
 wherein the K* at position 29 has been chemically modified such that the epsilon-amino group of the K-side chain is bonded with a -γE-CO—$(CH_2)_{14}$—$CH_3$ group;
 and the C-terminal amino acid is amidated as a C-terminal primary amide (SEQ ID NO:37).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is one γE residue and $X_6$ is a $C_{16}$ mono fatty acid and the K* residue has replaced the original amino acid at position 29).
 IVLSLDVPIGLLQILLEQEKQEKEKQQAK*TNARILARV-NH2
 wherein the K* at position 29 has been chemically modified such that the epsilon-amino group of the K-side chain is bonded with a -γE-γE-CO—$(CH_2)_{14}$—$CH_3$ group;
 and the C-terminal amino acid is amidated as a C-terminal primary amide (SEQ ID NO:38).

This sequence falls within the scope of Formula III (in that, in this particular embodiment, $X_1$ is an unmodified I residue, $X_2$ is L, $X_3$ is L, $X_4$ is R, $X_7$ is T, $X_8$ is R, $X_5$ is two γE residues and $X_6$ is a $C_{16}$ mono fatty acid and the K* residue has replaced the original amino acid at position 29).

IVLSLDVPIGLLQILLEQEKQEKEKQQATK*NARILARV-NH2
  wherein the K* at position 30 has been chemically modified such that the epsilon-amino group of the K-side chain is bonded with a -γE-CO—$(CH_2)_{14}$—$CH_3$ group;
  and the C-terminal amino acid is amidated as a C-terminal primary amide (SEQ ID NO:39).

This sequence falls within the scope of Formula III (in that, in this particular embodiment, $X_1$ is an unmodified I residue, $X_2$ is L, $X_3$ is L, $X_4$ is R, $X_8$ is R, $X_5$ is one γE residue and $X_6$ is a $C_{16}$ mono fatty acid and the K* residue has replaced the original amino acid (e.g., $X_7$) at position 30).

IVLSLDVPIGLLQK*LLEQEKQEKEKQQATTNA-QILAHV-NH2
  wherein the K* at position 14 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:40).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 14).

IVLSLDVPIGLLQIK*LEQEKQEKEKQQATTNAQI-LAHV-NH2
  wherein the K* at position 15 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:41).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 15).

IVLSLDVPIGLLQILK*EQEKQEKEKQQATTNAQ-ILAHV-NH2
  wherein the K* at position 16 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:42).

This sequence falls within the scope of Formula III (in that, in this particular embodiment, $X_1$ is an unmodified I residue, $X_2$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid (e.g., $X_3$) at position 16).

IVLSLDVPIGLLQILLK*QEKQEKEKQQATTNAQ-ILAHV-NH2
  wherein the K* at position 17 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:43).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 17).

IVLSLDVPIGLLQILLEK*EKQEKEKQQATTNAQI-LAHV-NH2
  wherein the K* at position 18 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:44).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 18).

IVLSLDVPIGLLQILLEQEKK*EKEKQQATTNAQI-LAHV-NH2
  wherein the K* at position 21 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:45).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 21).

IVLSLDVPIGLLQILLEQEKQEKEK*QQATTNAQ-ILAHV-NH2
  wherein the K* at position 25 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:46).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 25).

IVLSLDVPIGLLQILLEQEKQEKEKK*QATTNA-QILAHV-NH2
  wherein the K* at position 26 has been chemically modified such that the epsilon-amino group of the K-side chain is bonded with a ([2-(2-Amino-ethoxy)-ethoxy]-acetyl)$_2$-γE-γE-CO—$(CH_2)_{16}$—COOH group;
  and the C-terminal amino acid is amidated as a C-terminal primary amide (SEQ ID NO:47).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 26).

IVLSLDVPIGLLQILLEQEKQEKEKQQAK*TNAQI-LAHV-NH2 wherein the K* at position 29 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:48).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is H, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 29).

IVLSLDVPIK*LLQILLEQEKQEKEKQQATTNAQIL-AQV-Amide wherein the K* at position 10 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:49).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 10).

IVLSLDVPIGLLQILLK*QEKQEKEKQQATTNAQ-ILAQV-NH2 wherein the K* at position 17 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:50).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 17).

IVLSLDVPIGLLQILLEQEKQEKEKK*QATTN-AQILAQV-NH2 wherein the K* at position 26 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:51).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 26).

IVLSLDVPIGLLQILLEQEKQEKEKQQAK*TNAQILAQV-NH2 wherein the K* at position 29 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:52).

This sequence falls within the scope of Formula III (in that, in this particular embodiment, $X_1$ is an unmodified I residue, $X_2$ is L, $X_3$ is L, $X_4$ is Q, $X_7$ is T, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 29).

IVLSLDVPIGLLQILLK*QEKQEKEKQQATENAQI-LAQV-NH2 wherein the K* at position 17 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:53).

This sequence falls within the scope of Formula III (in that, in this particular embodiment, $X_1$ is an unmodified I residue, $X_2$ is L, $X_3$ is L, $X_4$ is Q, $X_7$ is E, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 17).

IVLSLDVPIGLLQILLEQEKQEKEKK*QATENAQI-LAQV-NH2 wherein the K* at position 26 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:54).

This sequence falls within the scope of Formula III (in that, in this particular embodiment, $X_1$ is an unmodified I residue, $X_2$ is L, $X_3$ is L, $X_4$ is Q, $X_7$ is E, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 26).

IVLSLDVPIGLLQILLEQEKQEKEKQQAK*EN-AQILAQV-NH2 wherein the K* at position 29 has been chemically modified such that the epsilon-amino group of the K-side chain is bonded with a ([2-(2-Amino-ethoxy)-ethoxy]-acetyl)$_2$-γE-γE-CO—(CH$_2$)$_{16}$—COOH group;

and the C-terminal amino acid is amidated as a C-terminal primary amide (SEQ ID NO:55).

This sequence falls within the scope of Formula III (in that, in this particular embodiment, $X_1$ is an unmodified I residue, $X_2$ is L, $X_3$ is L, $X_4$ is Q, $X_7$ is E, $X_8$ is Q, $X_5$ is a combination of two ([2-(2-Amino-ethoxy)-ethoxy]-acetyl) groups and two γE residues and $X_6$ is a $C_{18}$ diacid fatty acid and the K* residue has replaced the original amino acid at position 29).

IVLSLDVPIGLLQILLEQEKQEKEKQQAK*ENAQ-ILAQV-NH2 wherein the K* at position 29 has been chemically modified such that the epsilon-amino group of the K-side chain is bonded with a ([2-(2-Amino-ethoxy)-ethoxy]-acetyl)$_2$-γE-CO—(CH$_2$)$_{16}$—COOH group;

and the C-terminal amino acid is amidated as a C-terminal primary amide (SEQ ID NO:56).

This sequence falls within the scope of Formula III (in that, in this particular embodiment, X$_1$ is an unmodified I residue, X$_2$ is L, X$_3$ is L, X$_4$ is Q, X$_7$ is E, X$_8$ is Q, X$_5$ is a combination of two ([2-(2-Amino-ethoxy)-ethoxy]-acetyl) groups and a single γE residue and X$_6$ is a C$_{18}$ diacid fatty acid and the K* residue has replaced the original amino acid at position 29).

X$_1$IVLSLDVPIGLLQILLEQEKQEKEKQQAK*EN-AEILAQV-NH2 wherein X$_1$ has the N-terminus of the I residue modified by methylation;

wherein the K* at position 29 has been chemically modified such that the epsilon-amino group of the K-side chain is bonded with a ([2-(2-Amino-ethoxy)-ethoxy]-acetyl)-γE-γE-CO—(CH$_2$)$_{18}$—COOH group;

and the C-terminal amino acid is amidated as a C-terminal primary amide (SEQ ID NO:57).

This sequence falls within the scope of Formula III (in that, in this particular embodiment, X$_1$ represents that the I residue has been methylated at the N-terminus, X$_2$ is L, X$_3$ is L, X$_4$ is E, X$_7$ is E, X$_8$ is Q, X$_5$ is a combination of a single ([2-(2-Amino-ethoxy)-ethoxy]-acetyl) group and two γE residues and X$_6$ is a C$_{20}$ diacid fatty acid and the K* residue has replaced the original amino acid at position 29).

X$_1$IVLSLDVPIGLLQILLEQEKQEKEKQQAK*EN-AEILAQV-NH2 wherein X$_1$ has the N-terminus of the I residue modified by methylation;

wherein the K* at position 29 has been chemically modified such that the epsilon-amino group of the K-side chain is bonded with a γE-γE-CO—(CH$_2$)$_{18}$—COOH group;

and the C-terminal amino acid is amidated as a C-terminal primary amide (SEQ ID NO:58).

This sequence falls within the scope of Formula III (in that, in this particular embodiment, X$_1$ represents that the I residue has been methylated at the N-terminus, X$_2$ is L, X$_3$ is L, X$_4$ is E, X$_7$ is E, X$_8$ is Q, X$_5$ is two γE residues and X$_6$ is a C$_{20}$ diacid fatty acid and the K* residue has replaced the original amino acid at position 29).

X$_1$IVLSLDVPIGLLQILLEQEKQEKEKQQAK*ENA-EILAQV-NH2 wherein X$_1$ has the N-terminus of the I residue modified by methylation;

wherein the K* at position 29 has been chemically modified such that the epsilon-amino group of the K-side chain is bonded with a γE-([2-(2-Amino-ethoxy)-ethoxy]-acetyl)-γE-γE-CO—(CH$_2$)$_{18}$—COOH group;

and the C-terminal amino acid is amidated as a C-terminal primary amide (SEQ ID NO:59).

This sequence falls within the scope of Formula III (in that, in this particular embodiment, X$_1$ represents that the I residue has been methylated at the N-terminus, X$_2$ is L, X$_3$ is L, X$_4$ is E, X$_7$ is E, X$_8$ is Q, X$_5$ is a combination of a γE residue, a ([2-(2-Amino-ethoxy)-ethoxy]-acetyl) group and then two more γE residues and X$_6$ is a C$_{20}$ diacid fatty acid and the K* residue has replaced the original amino acid at position 29).

X$_1$IVLSLDVPIGLLQILLEQEKQEKEKQQAK*TNAQILAQV-NH2 wherein X$_1$ has the N-terminus of the I residue modified by methylation;

wherein the K* at position 29 has been chemically modified such that the epsilon-amino group of the K-side chain is bonded with a γE-([2-(2-Amino-ethoxy)-ethoxy]-acetyl)$_2$-γE-γE-CO—(CH$_2$)$_{18}$—COOH group;

and the C-terminal amino acid is amidated as a C-terminal primary amide (SEQ ID NO:60).

This sequence falls within the scope of Formula III (in that, in this particular embodiment, X$_1$ represents that the I residue has been methylated at the N-terminus, X$_2$ is L, X$_3$ is L, X$_4$ is Q, X$_7$ is T, X$_8$ is Q, X$_5$ is a combination of a γE residue, two ([2-(2-Amino-ethoxy)-ethoxy]-acetyl) groups and then two more γE residues and X$_6$ is a C$_{20}$ diacid fatty acid and the K* residue has replaced the original amino acid at position 29).

X$_1$IVLSLDVPIGLLQILLEQEKQEKEKQQAK*TNAQILAQV-NH2 wherein X$_1$ has the N-terminus of the I residue modified by methylation;

wherein the K* at position 29 has been chemically modified such that the epsilon-amino group of the K-side chain is bonded with a γE-([2-(2-Amino-ethoxy)-ethoxy]-acetyl)-γE-γE-CO—(CH$_2$)$_{18}$—COOH group;

and the C-terminal amino acid is amidated as a C-terminal primary amide (SEQ ID NO:61).

This sequence falls within the scope of Formula III (in that, in this particular embodiment, X$_1$ represents that the I residue has been methylated at the N-terminus, X$_2$ is L, X$_3$ is L, X$_4$ is Q, X$_7$ is T, X$_8$ is Q, X$_5$ is a combination of a γE residue, a ([2-(2-Amino-ethoxy)-ethoxy]-acetyl) group and then two more γE residues and X$_6$ is a C$_{20}$ diacid fatty acid and the K* residue has replaced the original amino acid at position 29).

X$_1$IVLSLDVPIGLLQILLEQEKQEKEKQQAK*TNAQILAQV-NH2 wherein X$_1$ has the N-terminus of the I residue modified by methylation;

wherein the K* at position 29 has been chemically modified such that the epsilon-amino group of the K-side chain is bonded with a γE-γE-([2-(2-Amino-ethoxy)-ethoxy]-acetyl)$_2$-γE-γE-CO—(CH$_2$)$_{18}$—COOH group;

and the C-terminal amino acid is amidated as a C-terminal primary amide (SEQ ID NO:62).

This sequence falls within the scope of Formula III (in that, in this particular embodiment, X$_1$ represents that the I residue has been methylated at the N-terminus, X$_2$ is L, X$_3$ is L, X$_4$ is Q, X$_7$ is T, X$_8$ is Q, X$_5$ is a combination of two γE residues, two ([2-(2-Amino-ethoxy)-ethoxy]-acetyl) groups and then two more γE residues and X$_6$ is a C$_{20}$ diacid fatty acid and the K* residue has replaced the original amino acid at position 29).

X$_1$IVLSLDVPIGLLQILLEQEKQEKEKQQAK*TNAQILAQV-NH2 wherein X$_1$ has the N-terminus of the I residue modified by methylation;

wherein the K* at position 29 has been chemically modified such that the epsilon-amino group of the K-side chain is bonded with a γE-γE-([2-(2-Amino-ethoxy)-ethoxy]-acetyl)-γE-γE-CO—(CH$_2$)$_{18}$—COOH group;

and the C-terminal amino acid is amidated as a C-terminal primary amide (SEQ ID NO:63).

This sequence falls within the scope of Formula III (in that, in this particular embodiment, X$_1$ represents that the I residue has been methylated at the N-terminus, X$_2$ is L, X$_3$ is L, X₄ is Q, X₇ is T, X₈ is Q, X₅ is a combination of two γE residues, a single ([2-(2-Amino-ethoxy)-ethoxy]-acetyl) group and then two more γE residues and X₆ is a $C_{20}$ diacid fatty acid and the K* residue has replaced the original amino acid at position 29).

X₁IVLSLDVPIGLLQILLEQEKQEKEKQQAK*TNAQILAQV-NH2
- wherein X₁ has the N-terminus of the I residue modified by methylation;
- wherein the K* at position 29 has been chemically modified such that the epsilon-amino group of the K-side chain is bonded with a γE-γE-γE-γE-CO—(CH₂)₁₈—COOH group;
- and the C-terminal amino acid is amidated as a C-terminal primary amide (SEQ ID NO:64).

This sequence falls within the scope of Formula III (in that, in this particular embodiment, X₁ represents that the I residue has been methylated at the N-terminus, X₂ is L, X₃ is L, X₄ is Q, X₇ is T, X₈ is Q, X₅ is a combination of four γE residues and X₆ is a $C_{20}$ diacid fatty acid and the K* residue has replaced the original amino acid at position 29).

X₁IVTSLDVPIGLLQILLEQEKQEKEKQQAK*TNAEILAQV-NH2
- wherein X₁ has the N-terminus of the I residue modified by methylation;
- wherein the K* at position 29 has been chemically modified such that the epsilon-amino group of the K-side chain is bonded with a γE-([2-(2-Amino-ethoxy)-ethoxy]-acetyl)₂-γE-γE-CO—(CH₂)₁₈—COOH group;
- and the C-terminal amino acid is amidated as a C-terminal primary amide (SEQ ID NO:66).

This sequence falls within the scope of Formula III (in that, in this particular embodiment, X₁ represents that the I residue has been methylated at the N-terminus, X₂ is T, X₃ is L, X₄ is E, X₇ is T, X₈ is Q, X₅ is a combination of a γE residue, two ([2-(2-Amino-ethoxy)-ethoxy]-acetyl) groups and then two more γE residues and X₆ is a $C_{20}$ diacid fatty acid and the K* residue has replaced the original amino acid at position 29).

It should be noted that, in addition to the methods of preparing the compounds described above, a convergent synthesis may also be used. For example, in this convergent synthesis, an acylated lysine sidechain is constructed and/or obtained. This acylated lysine side chain fragment may have the acid fragments protected orthogonally as t-butyl esters or other protecting groups commonly known in peptide synthesis. It is believed that such a method of synthesis may produce the acylated sidechain in high purity, ≥98% which may reduce the downstream chromatography requirements, potentially leading to improved purity and increased process efficiency. For example, in an all linear build, the acylated lysine component (i.e. the fatty acid side chain having the amino-ethoxy moieties, etc.) is typically installed at the end of the synthesis, and this can create high levels of process impurities such as, but not limited to impurities have greater or fewer numbers of amino-ethoxy moieties which can be problematic to remove. Using the convergent (outlined herein) strategy may de-risk an all linear synthetic build strategy, wherein a single mistake can result in a total loss. In addition, using a convergent synthesis approach may improve supply chain flexibility with comparable resourcing requirements to a standard all linear build. Additionally a convergent synthesis strategy may also be a means of lowering COPS (cost of product sold) and further improving robustness. Another benefit may be that the N-terminus N-methyl isoleucine residue is frequently a difficult coupling for a large peptide. Incorporation of N-methyl isoleucine onto a smaller fragment may be potentially a good means of de-risking this coupling issue.

Using the compound of Example 4 as an example, the acylated lysine side chain is close to the C-terminus, a strategic retrosynthetic break for a convergent synthesis process may be between the alanine (A) at position 28 and the lysine (K) at position 29. Thus, this "fragment" will include the lysine at position 29 (and its accompanying side chain) along with the final 9 residues (leading up to the C-terminus). In some embodiments, this "fragment" may be the primary parent fragment produced on Rink Amide or Sieber Amide resin. Another retrosynthetic disconnection may be between the Glycine (G) at position 10 and the Leucine (L) at position 11. Making a fragment of these sequences may ensure that such a sequence has no (or a lower) propensity for racemization. The third fragment of 18 amino acids (e.g., from the residue at position 11 to the Alanine at position 28 could also be produced. This 18 residue fragment, along with the initial 10 amino acid fragment (e.g., the N-terminus to the G at position 10) could both be produced, for example, by a 2-CTC resin. The 2-CTC resin may often be preferred for synthesis of most fragments as the resin can be orthogonally cleaved while leaving peptide protecting groups in tact.

Thus, in summary, the following synthesis method for the compound of Example 4 is provided below:
1) Construct the fatty acid side chain that is connected to a Lysine (e.g., the K that will ultimately be K at position 29);
2) Construct a 10 amino acid fragment starting with the Lysine with the fatty acid side chain (e.g., the K that will ultimately be K at position 29) and add the other amino acids to ending in the C-terminus after the final V residue;
3) Construct the 18 amino acid residue fragment, starting with the L at position 11 and ending with the A at position 28;
4) Construct the 10 amino acid fragment starting with the modified I at position 1 and ending with the G at position 10;
5) The 18 residue fragment of step 3 could be coupled to the 10 reside fragment of step 4, and then this 28 construct could be coupled to the fragment of step 2 (having the side chain); alternatively the 18 residue fragment of step 3 could be coupled to the added to 10 amino acid fragment of step 2, and then this residue construct could be coupled to the fragment of step 4.

Again, one of the benefits of using this "fragment" based construction technique is that each fragment could be produced sequentially or simultaneously. Further, the smaller fragments of the peptides may be easier to purify and sometimes can be isolated in crystalline form which imparts high purity. Likewise, if an error is made in one of the fragment, only that fragment has to be discarded and re-created (rather than having to re-create the entire compound). Other strategic fragment breaks are possible to further improve purity and efficiency such as but not limited to fragment condensation to produce the 18 amino acid residue.

In some embodiments, lyophilization may be incorporated as the strategy as a means of potentially de-risking potential physical property issues of the compound. Specifically, the compound may be constructed by in which it is purified via chromatography. Once purified, the solution may be concentrated and then isolated as a solid (e.g., dry powder) via lyophilization. In alternate embodiments, a solid may be obtained and isolated using a precipitation/filtration/drying/humidification procedure.

Lyophilization is the most commonly practiced (≥80%) industrial means for production of solid peptide drug products for storage or reconstitution. In some embodiments, the primary drawback to precipitation is the extensive material and design space development necessary to assure a robust process. Precipitated compounds may also contain high density particles which tend to agglomerate and frequently these precipitated products may slowly dissolve with standard dissolution assays and/or drug product formulations. On the other hand, high surface area product produced by lyophilization may assure maximized dissolution rates in dissolution assays and/or drug product formulations. However, precipitation products may also be used, as this method tends to be less expensive for high volume products.

In other embodiment, the present invention is also directed to a compound comprising the following amino acid sequence:

wherein $X_1$ denotes that the I residue is modified by either acetylation or methylation at the N-terminus;
wherein $X_2$ is L or T;
wherein $X_3$ is L or I;
wherein $X_4$ is Q or E (SEQ ID NO:18).

This sequence has use as an intermediate. Specifically, this sequence may be used as an intermediate to construct the compounds described herein. In this particular method, synthesis on this intermediate would begin on a solid phase (in the manner outlined above) starting from the V at position 38 and finishing at the I (with either the acyl or N-methyl group at the N-terminus). Once this sequence is constructed, the K at position 29 would be deprotected such that the orthogonal protecting group is removed. Then, the particular group of the formula —$X_5$—$X_6$ could then be added to the epsilon-amino group of the K-side chain at position 29. Any of the particular side chains for the group of the formula —$X_5$—$X_6$ outlined herein may be used. Such addition of the group of the formula —$X_5$—$X_6$ may be added while the peptide is still attached to the solid phase. After adding the group of the formula —$X_5$—$X_6$, the peptide may be released from the resin and purified.

Assays

Provided below are the conditions and data for some of the above-recited Examples in several assays: in vitro function and selectivity, pharmacokinetics, type II diabetes, muscle atrophy, chronic kidney disease (diabetic nephropathy, hypertensive nephropathy), and blood pressure.

In Vitro Function and Selectivity

CRHR agonistic activity is measured in a cell-based cAMP assay. Serial dilutions of the test peptides are made in assay buffer containing Hank's Balanced Salt Solution (HBSS, without phenol red) supplemented with 20 mM HEPES and 0.05% lactalbumin enzymatic hydrolysate (LAH) ("assay buffer"). The highest concentration that is used starts from 1 µM in the human CRHR2b, whereas 100 µM starting concentration is used in the human CRHR1 assay. A one to three dilution of the test peptides is used in both assays.

Receptor over-expressing Chinese Hamster Ovary (CHO) cell line is used for the human CRHR2b assay. CHO cells are grown in DMEM supplemented with 10% fetal bovine serum at 37° C. under suspension conditions and transiently transfected with cDNA constructs of human CRHR2b (Genbank accession number: AF011406.1). Forty-eight hours after the transfection, the cells are centrifuged to remove the culture media and resuspended in fetal bovine serum containing 5% DMSO. They are cryofrozen and stored in vials in liquid nitrogen (20×106 cells/ml/vial). On the day of the assay, cells are thawed and resuspended in cold 30 ml culture media supplemented with 20 mM HEPES. The cells are then centrifuged to remove the media and washed once with HBSS supplemented with 20 mM HEPES. Finally, following the last centrifugation, the cells are resuspended in assay buffer. Thirty-thousand cells are used in the human CRHR2b assay for each treatment.

The human Retinoblastoma cell line Y79 (ATCC #HTB-18), which expresses endogenous human CRHR1, is used in the human CRHR1 assay. The cells are grown in RPMI 1640 (Hyclone, #SH30255) containing 20% fetal bovine serum and 10 mM HEPES, in suspension culture. Cells are centrifuged to remove the culture media and washed once in HBSS supplemented with 20 mM HEPES. The cells are resuspended in the assay buffer and 20,000 cells are used per treatment in the human CRHR1 assay.

The cells are dispensed into Costar 96-well black polystyrene half area EIA/RIA plates (Corning Incorporated, Corning, N.Y.) followed by the addition of the diluted peptides, each at a volume of 20 µL. The agonist induced cAMP levels are detected using a HTRF cAMP Dynamic 2 kit (CisBio, Bedford, Mass.). After incubation at 37° C. for 30 min, the assay is stopped by cell lysis via the addition of 20 µL of d2-labeled cAMP and followed by 20 µL of cryptate-labeled anti-cAMP antibody, as described by the manufacturer. Cellular cAMP (as a result of agonist stimulation) competes with the d2-labeled cAMP for binding to the antibody. HTRF detection is performed on an Envision plate reader (Perkin Elmer Life and Analytical Sciences, Waltham, Mass.) by measuring ratiometric emission at 620 and 665 nm after excitation at 320 nm.

The data are converted to picomoles of cAMP using a standard curve obtained from the same assay performed with varying concentrations of unlabeled cAMP. Percent of the maximum activation of the cells is calculated using converted picomole cAMP data by comparing to the amount of cAMP produced by 1 µM human UCN2 for the human CRHR2b or 1 µM human UCN1 for the human CRHR1 assay. The data are analyzed using a Curve Fitting Tool to calculate ED50. Numeric values shown below in Table 1 represent the mean of multiple runs (number of runs shown in parentheses) following the mean value±SEM.

TABLE 1

In vitro activity for hCRHR2b and hCRHR1.

| Example | hCRHR2b Average EC50 (nM) | hCRHR1 Average EC50 (nM) |
| --- | --- | --- |
| hUCN1 | 0.81 ± 0.96 (n = 14) | 7.30 ± 3.65 (n = 23) |
| hUCN2 | 0.19 ± 0.12 (n = 32) | >100000 (n = 6) |
| Example 1 | 2.44 ± 1.36 (n = 3) | ~10000 (n = 5) |
| Example 2 | 1.20 ± 0.52 (n = 4) | >10000 (n = 4) |
| Example 3 | 2.00 ± 1.11 (n = 5) | >100000 (n = 4) |
| Example 4 | 1.85 ± 0.51 (n = 8) | >100000 (n = 4) |
| Example 5 | 1.01 ± 0.23 (n = 8) | 33891 ± 16067 (n = 4) |
| Example 6 | 2.50 ± 1.06 (n = 8) | >100000 (n = 4) |
| Example 7 | 0.94 ± 0.05 (n = 4) | ~100000 (n = 4) |

These data demonstrate that the compounds of Examples 1 to 7 have CRHR2 agonist activity in a cAMP assay. These data further demonstrate that the compounds of Examples 1 to 7 are selective for CRHR2, over CRHR1.

Pharmacokinetics

Plasma concentrations of compounds were determined by LC/MS methods. Each method measured the intact compound; peptide plus linked time extension. For each assay, the compound and an analog, used as an internal standard (IS), were extracted from 100% mouse, rat or monkey plasma (25 µl) using acetonitrile. Two distinct layers were formed upon centrifugation with the compound and the IS located in the supernatant layer. An aliquot of the supernatant (80 µl) was transferred to a Thermo Protein Precipitation Plate with water (150 µl) and formic acid (25 µl) followed by mixing. A final 31% acetonitrile in 10% formic acid sample (10 µl) was loaded onto a Supelco Analytical Discovery BIO Wide Pore C5-3 column (5 cm×1 mm, 3 µm). The column effluent was directed into a Thermo Q-Exactive mass spectrometer for detection and quantitation.

Male Cynomolgus monkeys were administered a single subcutaneous dose or intravenous dose (96.4 nmol/kg) of a compound described herein in 20 mM Tris-HCl Buffer (pH 7) at a volume of 1 mL/kg. Blood was collected from each animal at 2, 6, 24, 48, 72, 96, 168, 240, 336, 408, and 504 hours postdose for pharmacokinetic characterization.

Male Cynomolgus monkeys were also administered a single subcutaneous dose (50 nmol/kg) of a compound described herein in 20 mM Tris-HCl Buffer (pH 8) at a volume of 0.26 mL/kg. Blood was collected from each animal at 3, 6, 12, 24, 48, 72, 96, 120, 168, 192, 240, 336, 408, and 504 hours postdose for pharmacokinetic characterization.

Male Sprague Dawley rats were administered a single subcutaneous dose (50 or 150 nmol/kg) of a compound described herein in 20 mM Tris-HCl Tris Buffer (pH 8) at a volume of 0.26 or 0.77 mL/kg. Blood was collected from each animal at 6, 12, 24, 48, 72, 96, 120, 144, 168, 192, 240, 288, and 336 hours postdose for pharmacokinetic characterization.

Male CD-1 mice were administered a single subcutaneous dose (350, 386 or 388 nmol/kg) of a compound described herein in 20 mM Tris-HCl Tris Buffer (pH 7 or 8) at a volume of 0.05 or 0.06 mL/animal. Blood was collected at 6, 12, 24, 48, 72, 96, 120 and 168 hours postdose for pharmacokinetic characterization (101).

TABLE 2

Individual and Mean Pharmacokinetic Parameters Following a Single 50 or 96.4 nmol/kg Subcutaneous Dose to Male Cynomolgus Monkeys

| Compound (Dose) | | $T_{1/2}$ (hr) | Tmax (hr) | Cmax (nmole/L) | $AUC_{0\text{-}inf}$ (hr*nmole/L) | CL/F (mL/hr/kg) |
|---|---|---|---|---|---|---|
| Example 2 | | 97 | 24 | 1238 | 237954 | 0.41 |
| (96.4 | | 84 | 48 | 1699 | 245711 | 0.39 |
| nmol/kg) | Mean | 91 | 36 | 1469 | 241833 | 0.40 |
| Example 3 | | 101 | 48 | 441 | 69880 | 0.72 |
| (50 | | 70 | 24 | 432 | 58414 | 0.86 |
| nmol/kg) | Mean | 85 | 36 | 437 | 64147 | 0.79 |

TABLE 2-continued

Individual and Mean Pharmacokinetic Parameters Following a Single 50 or 96.4 nmol/kg Subcutaneous Dose to Male Cynomolgus Monkeys

| Compound (Dose) | | $T_{1/2}$ (hr) | Tmax (hr) | Cmax (nmole/L) | $AUC_{0\text{-}inf}$ (hr*nmole/L) | CL/F (mL/hr/kg) |
|---|---|---|---|---|---|---|
| Example 4 | | 79 | 48 | 333 | 51829 | 0.97 |
| (50 | | 106 | 24 | 291 | 46654 | 1.07 |
| nmol/kg) | Mean | 93 | 36 | 312 | 49241 | 1.02 |

Abbreviations for this table:

$AUC_{0\text{-}inf}$ = area under the curve from time 0 hours to infinity,

CL/F = clearance/bioavailability,

Tmax = time to maximal concentration,

Cmax = maximum observed plasma concentration,

T1/2 = half-life.

TABLE 3

Individual and Mean Pharmacokinetic Parameters Following a Single 96.4 nmol/kg Intravenous Dose to Male Cynomolgus Monkeys

| Compound (Dose) | | $T_{1/2}$ (hr) | $C_0$ (nmole/L) | $AUC_{0\text{-}inf}$ (hr*nmole/L) | CL (mL/hr/kg) |
|---|---|---|---|---|---|
| Example 2 | | 124 | 3267 | | 0.28 |
| (96.4 | | 98 | 3059 | | 0.36 |
| nmol/kg) | Mean | 111 | 3163 | 305766 | 0.32 |

Abbreviations for this table:

$AUC_{0\text{-}inf}$ = area under the curve from time 0 hours to infinity,

CL = clearance, $C_0$ = Estimated plasma concentration at time zero, $T_{1/2}$ = half-life.

TABLE 4

Individual and Mean Pharmacokinetic Parameters Following a Single 50 or 150 nmol/kg Subcutaneous Dose to Male Sprague Dawley Rats

| Compound (Dose) | | $T_{1/2}$ (hr) | Tmax (hr) | Cmax (nmole/L) | $AUC_{0\text{-}inf}$ (hr*nmole/L) | CL/F (mL/hr/kg) |
|---|---|---|---|---|---|---|
| Example 2 | | 37 | 24 | | | 4.1 |
| (150 | | 32 | 24 | | | 4.9 |
| nmol/kg) | | 34 | 24 | | | 5.0 |
| | Mean | 34 | 24 | 429 | 32268 | 4.7 |
| | SD | 3 | 0 | 53 | 3532 | 0.5 |
| Example 3 | | 16 | 12 | 188 | | 6.2 |
| (50 nmol/kg) | | 14 | 24 | 160 | | 7.5 |
| | | 17 | 24 | 141 | | 7.3 |
| | Mean | 16 | 20 | 163 | 7175 | 7.0 |
| | SD | 1 | 7 | 24 | 784 | 1.0 |
| Example 3 | | 16 | 24 | 531 | | 6.0 |
| (150 | | 16 | 24 | 496 | | 6.2 |
| nmol/kg) | | 16 | 24 | 470 | | 6.4 |
| | Mean | 16 | 24 | 499 | 24363 | 6.0 |
| | SD | 0 | 0 | 31 | 801 | 0.0 |
| Example 4 | | 19 | 24 | 126 | | 6.4 |
| (50 nmol/kg) | | 21 | 24 | 150 | | 6.6 |
| | | 20 | 24 | 127 | | 7.0 |
| | Mean | 20 | 24 | 134 | 7513 | 7.0 |
| | SD | 1 | 0 | 14 | 326 | 0.0 |

TABLE 4-continued

Individual and Mean Pharmacokinetic Parameters Following a Single 50 or 150 nmol/kg Subcutaneous Dose to Male Sprague Dawley Rats

| Compound (Dose) | | $T_{1/2}$ (hr) | Tmax (hr) | Cmax (nmole/L) | $AUC_{0-inf}$ (hr*nmole/L) | CL/F (mL/hr/kg) |
|---|---|---|---|---|---|---|
| Example 4 (150 nmol/kg) | | 21 | 24 | 356 | | 6.8 |
| | | 20 | 24 | 527 | | 5.3 |
| | | 21 | 24 | 482 | | 6.0 |
| | Mean | 21 | 24 | 455 | 25057 | 6.0 |
| | SD | 0 | 0 | 89 | 3136 | 1.0 |

Abbreviations for this table:
$AUC_{0-inf}$ = area under the curve from time 0 hours to infinity,
CL/F = clearance/bioavailability,
Tmax = time to maximum concentration,
Cmax = maximum observed plasma concentration,
T1/2 = half-life.

TABLE 5

Mean Pharmacokinetic Parameters Following a Single Subcutaneous Dose to Male CD-1 Mice

| Compound (Dose) | Study | $T_{1/2}$ (hr) | Tmax (hr) | Cmax (nmole/L) | $AUC_{0-inf}$ (hr*nmole/L) | CL/F (mL/hr/kg) |
|---|---|---|---|---|---|---|
| Example 1 (388 nmol/kg) | 8296049 | 16 | 12 | 1149 | 32209 | 12.1 |
| Example 2 (386 nmol/kg) | 8296049 | 20 | 12 | 1152 | 46488 | 8.3 |
| Example 3 (350 nmol/kg) | 8323964 | 14 | 12 | 1338 | 35527 | 9.9 |
| Example 4 (350 nmol/kg) | 8315101 | 18 | 24 | 1164 | 51552 | 6.8 |

Abbreviations for this table:
$AUC_{0-inf}$ = area under the curve from time 0 hours to infinity,
CL/F = clearance/bioavailability,
Tmax = time to maximal concentration,
Cmax = maximum observed concentration,
T1/2 = half-life.

These data demonstrate that the above compounds have a pharmacokinetic profile suitable for once weekly administration or other types of administration such as bi-monthly or monthly.

Type II Diabetes

In Vivo Diet Induced Obesity (DIO) Model—Chronic Dose Administration

The DIO model represents a pre-diabetic state that is sensitive to insulin. These animals, although not diabetic, display insulin resistance, dyslipidemia, and hepatic steatosis, all characteristics of metabolic syndrome, after being placed on a high fat (60% Kcal from fat) diet for 12 weeks (Surwit R S et al., Diet-induced type II diabetes in C57BL/6J mice. *Diabetes* 37(9): 1163-7 (1988)). The purpose of this study is to assess the effects of the molecules of Examples 4, 5, 6, and 7 on fasting glucose, fasting insulin, weight loss, and body composition.

Male C57BL6 mice 22 weeks old (on high fat diet since 6 weeks of age, Jackson Laboratories 3800050; Bar Harbor, Me.) are housed 1 per cage and maintained on D12492 chow (60% lard high fat diet: Research diets New Brunswick N.J.) for 2 weeks in the vivarium and on a normal light cycle prior to experiment start. Animals are randomized by body weight to treatment groups using block randomization. On day 1 of experiment animals and food are weighed and recorded. Animals are separated in to two equal groups and started on separate days (data combined) to simplify the logistics of the study. Animals are given a single subcutaneous injection (s.c.) of the indicated treatment in 20 mM citrate pH 7 on days 1 (start), 4, 7, 10, and 13 of experiment at a volume of 10 ml/kg. Vehicle control animals are injected with a similar volume of this solution. The solutions are kept in sterile capped vials stored at 4° C. for the duration of the study. Each treatment arm has an n of 5 mice per group.

From study day 1 to study day 15 the animals and their food are weighed daily prior to dose administration. These data are used to calculate body weight gain and food consumption. The animals or the wire rack containing the food are placed in a weigh pan and the balance is allowed to stabilize. The weight is recorded.

On Study Day 15, the animals are fasted overnight (approximately 16-18 hours) by placing them in a clean cage with a clean wire rack without food but allowed access to water, and on day 16 are subjected to a intraperitoneal glucose tolerance test (ipGTT). This is performed as follows; the tail of the animal is resected and baseline blood and serum samples (Time 0) are collected and the animals are injected intraperitoneally (ip) with a bolus of 2 g/kg glucose in sterile saline at a volume of 5 ml/kg. Thereafter, blood glucose and serum samples for insulin are collected at 20, 60, and 120 minutes after injection. Blood glucose is measured using an Accu-Chek Aviva glucose meter (Roche; Indianapolis, Ind.). The serum samples are centrifuged in a micro hematocrit centrifuge at 9000 relative centrifugal force (rcf) for 5 minutes. The serum is collected and analyzed for insulin using a Rat/Mouse Insulin Kit (Mesoscale Discovery). Statistical significance (*=p>0.05 vs. 0 dose; one way ANOVA Dunnett's post hoc) is calculated using GraphPad Prizm software (La Jolla, Ca). Glucose and insulin AUC are calculated using GraphPad Prism software (GraphPad Software Inc., La Jolla, Calif.). The area is computed between 0 and the curve, starting from the first X value in the data set and ending at the largest X value (from 0, Trapezoid rule).

On study day 1 and study day 15 (prior to fasting for the IPGTT measurement), body composition is analyzed using Quantitative Nuclear Magnetic Resonance EchoMRI analyzer (EMR-166-s, EchoMRI; Houston Tex.). After calibrating the analyzer with a known amount of canola oil, the animals are placed in the analyzer which measures fat and non-fat (lean) mass in grams. Change in mass is calculated by subtraction of the day 15 value from the day 1 value.

Tables 6, 7, 8 and 9 below show data corresponding to each of the above measurements. The data are represented as the arithmetic mean with SEM.

The data in Tables 6 to 9 demonstrate that subcutaneous administration of Examples 4-7 once every three days for 15 consecutive days results in the following significant differences: (1) decreases in: total body weight and improved body composition (represented as a decrease in fat mass with no significant change in lean mass) when compared to the Vehicle DIO mice. Further, Examples 4-7 when injected every third day s.c. for 15 consecutive days showed the following significant differences: (1) reduction of fasting serum glucose and serum insulin and (2) improvements in: glucose tolerance (represented by the reductions in glucose and insulin AUC during IPGTT). When an $ED_{50}$ for fasting serum insulin lowering is calculated, Example 4, 5, and 6 produced $ED_{50}$'s of 6.47, 6.23 and 16.97 nmol/kg, respectively.

TABLE 6

In vivo chronic dose administration in male DIO mice.
Example 4

| Dose | 0 nmol/kg (n = 5) | 2.4 nmol/kg (n = 5) | 7.2 nmol/kg (n = 5) | 24 nmol/kg (n = 5) | 72 nmol/kg (n = 5) | 144 nmol/kg (n = 5) | ED50 (nmol/kg) |
|---|---|---|---|---|---|---|---|
| Body weight change (% change ± SEM) | 3.7 ± 0.66 | 2.3 ± 1.6 | −0.52 ± 1.2 | −4.1 ± 1.6* | −15 ± 1.2* | −15 ± 0.98* | 29.03 |
| Fasting blood glucose(mg/dL ± SEM) | 119 ± 5.6 | 93 ± 6.4* | 80 ± 3.8* | 86 ± 4.6* | 80 ± 3.8* | 78 ± 3.2* | Ambiguous |
| Fasting serum insulin (ng/mL ± SEM) | 1.4 ± 0.24 | 1.3 ± 0.08 | 0.56 ± 0.21 | 0.52 ± 0.14 | 0.25 ± 0.15* | 0.6 ± 0.4 | 4.30 |
| Blood glucose AUC during ipGTT (mg/dL × min$^{-1}$) | 46831 ± 2531 | 32016 ± 3812* | 31918 ± 2396* | 31649 ± 2174* | 29750 ± 3055* | 27984 ± 1481* | Ambiguous |
| Serum insulin AUC during ipGTT (ng/mL × min$^{-1}$) | 285 ± 39 | 313 ± 22 | 218 ± 42 | 205 ± 31 | 132 ± 14* | 118 ± 7.4* | 21.13 |
| Fat mass change (g ± SEM) | 1.3 ± 0.22 | 0 ± 0.7 | −1 ± 0.45 | −2.7 ± 0.63* | −7.8 ± 0.56* | −7.1 ± 0.54* | 27.19 |
| Lean mass change (g ± SEM) | 0.3 ± 0.32 | 1.2 ± 0.21 | 0.52 ± 0.16 | 0.84 ± 0.33 | 0.14 ± 0.19 | 0.02 ± 0.36 | Ambiguous |

*represents significance (p < 0.05) compared to Vehicle DIO and is calculated by One-Way ANOVA with a Dunnett's Comparison using GraphPad Prizm software (La Jolla, Ca)

TABLE 7

In vivo chronic dose administrationin male DIO mice.
Example 5

| Dose | 0 nmol/kg (n = 5) | 2.4 nmol/kg (n = 5) | 7.2 nmol/kg (n = 5) | 24 nmol/kg (n = 5) | 72 nmol/kg (n = 5) | 144 nmol/kg (n = 5) | ED50 (nmol/kg) |
|---|---|---|---|---|---|---|---|
| Body weight change (% change ± SEM) | 3.7 ± 0.66 | 0.88 ± 2.4 | −2.1 ± 0.62 | −11 ± 1.4* | −13 ± 1.7* | −13 ± 1.5* | 10.22 |
| Fasting blood glucose(mg/dL ± SEM) | 119 ± 5.6 | 86 ± 3.5* | 83 ± 2.5* | 80 ± 3.9* | 80 ± 3.5* | 77 ± 3.7* | Ambiguous |
| Fasting serum insulin (ng/mL ± SEM) | 1.4 ± 0.24 | 1.1 ± 0.2 | 0.65 ± 0.1* | 0.52 ± 0.21* | 0.25 ± 0.09* | 0.41 ± 0.12* | 6.23 |
| Blood glucose AUC during ipGTT (mg/dL × min$^{-1}$) | 46831 ± 2531 | 34313 ± 1608* | 30089 ± 2822* | 32291 ± 2283* | 32768 ± 4860* | 26859 ± 1697* | Ambiguous |
| Serum insulin AUC during ipGTT (ng/mL × min$^{-1}$) | 285 ± 39 | 240 ± 26 | 167 ± 24 | 108 ± 21 | 163 ± 26* | 285 ± 39 | 9.70 |
| Fat mass change (g ± SEM) | 1.3 ± 0.22 | −0.78 ± 0.87 | −2.6 ± 0.33* | −5.8 ± 0.48* | −6.6 ± 0.74* | −6.1 ± 0.89* | 6.60 |
| Lean mass change (g ± SEM) | 0.3 ± 0.32 | 1.3 ± 0.42 | 1.3 ± 0.48 | −0.04 ± 0.29 | 0.16 ± 0.17 | 0.49 ± 1.1 | Ambiguous |

*represents significance (p < 0.05) compared to Vehicle DIO and is calculated by One-Way ANOVA with a Dunnett's Comparison using GraphPad Prizm software (La Jolla, Ca)

TABLE 8

In vivo chronic dose administration in male DIO mice.
Example 6

| Dose | 0 nmol/kg (n = 5) | 2.4 nmol/kg (n = 5) | 7.2 nmol/kg (n = 5) | 24 nmol/kg (n = 5) | 72 nmol/kg (n = 5) | 144 nmol/kg (n = 5) | ED50 (nmol/kg) |
|---|---|---|---|---|---|---|---|
| Body weight change (% change ± SEM) | 5.3 ± 1.1 | 2.3 ± 1.4 | 1 ± 1.9 | −3.5 ± 0.77* | −9.9 ± 2.3* | −16 ± 0.88* | 33.56# |
| Fasting blood glucose(mg/dL ± SEM) | 127 ± 4.5 | 99 ± 3.1* | 91 ± 4.3* | 95 ± 2.9* | 86 ± 4.2* | 86 ± 4.5* | Not converged |
| Fasting serum insulin (ng/mL ± SEM) | 1.4 ± 0.29 | 1.1 ± 0.22 | 1.1 ± 0.34 | 0.6 ± 0.14 | 0.53 ± 0.21 | 0.34 ± 0.16 | 16.97 |
| Blood glucose AUC during ipGTT (mg/dL × min$^{-1}$) | 42526 ± 2213 | 32775 ± 2674 | 24439 ± 2165* | 29473 ± 3180* | 29719 ± 3115* | 24650 ± 1532* | Ambiguous |
| Serum insulin AUC during ipGTT (ng/mL × min$^{-1}$) | 315 ± 39 | 306 ± 44 | 230 ± 28 | 173 ± 22* | 115 ± 11* | 89 ± 17* | 15.49 |

TABLE 8-continued

In vivo chronic dose administration in male DIO mice.
Example 6

| Dose | 0 nmol/kg (n = 5) | 2.4 nmol/kg (n = 5) | 7.2 nmol/kg (n = 5) | 24 nmol/kg (n = 5) | 72 nmol/kg (n = 5) | 144 nmol/kg (n = 5) | ED50 (nmol/kg) |
|---|---|---|---|---|---|---|---|
| Fat mass change (g ± SEM) | 1.8 ± 0.43 | 0.34 ± 0.48 | −0.79 ± 0.4.9 | −2.8 ± 0.62* | −5.6 ± 0.96* | −8 ± 0.43* | 22.33 |
| Lean mass change (g ± SEM) | 0.16 ± 0.2 | 0.75 ± 0.25 | 1.1 ± 0.49 | 0.87 ± 0.16 | 0.91 ± 0.17 | 0.53 ± 0.24 | Ambiguous |

*represents significance (p < 0.05) compared to Vehicle DIO and is calculated by One-Way ANOVA with a Dunnett's Comparison using GraphPad Prizm software (La Jolla, Ca).
bottom of curve fixed to highest dose.

TABLE 9

In vivo chronic dose administration in male DIO mice.

Example 7

| Dose | 0 nmol/kg (n = 5) | 24 nmol/kg (n = 5) |
|---|---|---|
| Body weight change (% change ± SEM) | 3.8 ± 0.41 | −11 ± 1.6* |
| Blood glucose AUC during ipGTT (mg/dL × min$^{-1}$) | 46453 ± 883 | 26495 ± 1399* |
| Serum insulin AUC during ipGTT (ng/mL × min$^{-1}$) | 423 ± 67 | 144 ± 17* |
| Fasting blood glucose (mg/dL ± SEM) | 142 ± 6.8 | 87 ± 3.5* |
| Fasting serum insulin (ng/mL ± SEM) | 2.3 ± 0.29 | 0.26 ± 0.14* |

*represents significance (p < 0.05) compared to Vehicle DIO and is calculated by One-Way ANOVA with a Dunnett's Comparison using GraphPad Prizm software (La Jolla, Ca)

C57BL6 mice 22 weeks old (on high fat diet since 6 weeks of age, Jackson Laboratories 380050; Bar Harbor, Me.) are housed and treated as described above. Animals are randomized by body weight to treatment groups using block randomization. On day 1 of experiment animals and food are weighed and recorded. Animals are separated into three equal groups and started on separate days (data combined) to simplify the logistics of the study. Animals are given a single s.c. injection of the indicated treatment in 20 mM citrate pH 7 on days 1 (start), 4, 7, 10, and 13 of experiment at a volume of 10 ml/kg. Vehicle control animals are injected with a similar volume of this solution. The solutions are kept in sterile capped vials stored at 4° C. for the duration of the study.

On the 14$^{th}$ day of study (the morning of the in vivo glucose uptake experiment), DIO mice are placed in clean cages and food is removed for 4 hours. Animals are then anesthetized with 2% isoflurane, and 10 μCi of [$^3$H]-2-deoxyglucose together with the indicated insulin dose or saline (together in 100 ul of sterile saline) is injected retro-orbitally with a 0.3 ml syringe. The tip of the tail is resected and at 2, 5, 10, 15, 20 and 30 minutes after isotope injection, a drop of blood is taken for measurement of blood glucose in triplicate via Accu-Chek Aviva glucose meter (Roche; Indianapolis, Ind.). These values represent Cp. At the same time points indicated above, an additional 10 μl of blood is taken and placed into a Heparin tube, mixed, and placed on ice. Five 5 μl of the heparinized blood is then transferred to a clean microcentrifuge tube, and 125 μl of 1 M Ba(OH)$_2$ and 125 μl of 1 M ZnSO$_4$ are added sequentially. The tube is then mixed and placed on ice. The tubes are centrifuged at 8000 rcf for 5 minutes. Two hundred al of the supernatant is combined with 5 ml of scintillation fluid and counted in order to determine plasma disintegrations per minute (DPM). These values represent C*p.

After the final blood sample is collected at 30 minutes, the animals are then euthanized by cervical dislocation and tissues samples (red quadriceps (RQ), white quadriceps (WQ), soleus, extensor digitorum longus (EDL)) are removed and frozen between clamps cooled in liquid nitrogen. Tissues are stored at −80° C. until processed. Tissues are then processed for counting by placing 50-100 mg of dry tissue weight in a 2 ml Lysing Matrix D tube kept on dry ice. One 1 ml of 0.5% Perchloric acid is added to the tube and the tissue is homogenized on setting 6.0 for 30 seconds using Fastprep-24 (MP Bio, Santa Ana, Calif.). The sample is neutralized by the addition of 20 μl of 5N KOH mixed and centrifuged at 2000 rcf for 15 minutes at 4° C. Three hundred μl of the neutralized supernatant is placed into two separate clean 1.5 ml microcentrifuge tubes. Three hundred μl of distilled water is added to the first tube, while 150 μl of Barium Hydroxide (Ba(OH)$_2$ and 150 μl of Zinc Sulfate (ZnSO$_4$) are sequentially added to the second tube. The samples are then mixed and incubated for 1 hour on ice. Both sets of tubes are then centrifuged at 3000 rcf for 15 minutes at 4° C. Two hundred ul from each tube is added to a 7 ml scintillation vial and 5 ml of scintillation fluid (Scinti-Safe) is then added. The vials are then counted for DPM in a Beckman Scintillation counter (Beckman-Coulter, Brea Calif.). The difference in the DPM between these samples represents C*m.

Uptake of 2-deoxyglucose by the respective tissues is calculated by the following formula:

$$Rg = (C*m)/\int Cp*/Cpdt$$

Rg=glucose metabolic rate (μmol/100 g/min)

C*m=accumulated 2DG6P (dpm/100 g wet weight) at t=30 min

C*p=plasma 2DG activity (dpm/ml)

Cp is plasma glucose (mM)

Tables 10 and 11 below show the data corresponding to each of the above measurements. The data are represented as the arithmetic mean with SEM.

The data in Table 10 demonstrate that subcutaneous administration once every three days of Example 7 for 14 consecutive days results in a significant increase in muscle glucose uptake when stimulated by a submaximal insulin concentration (0.5 U/kg) in RQ, WQ and EDL, while uptake in the soleus muscle is not altered when compared to the corresponding value for the Vehicle DIO mice. In addition, the data in Table 11 indicate that the combined weights of both EDL muscles are significantly increased by subcutaneous administration once every three days of Example 7 for 14 consecutive days.

TABLE 10

In vivo muscle glucose uptake in male DIO mice treated with the molecule of Example 7.
Tissue 2-Deoxyglucose Uptake mol/100 g/min

| Group | Tissue | Saline | N | 0.5 U/kg | N | 5 U/kg | N |
|---|---|---|---|---|---|---|---|
| Vehicle | RQ | 3.02 ± 0.22 | 6 | 6.378 ± 0.7 | 5 | 12.38 ± 2.04 | 6 |
| Example 7 | RQ | 4.97 ± 0.74 | 4 | 13.33 ± 1.36* | 12 | 16.65 ± 1.27 | 6 |
| Vehicle | WQ | 2.53 ± 0.24 | 6 | 5.66 ± 0.74 | 6 | 8.93 ± 0.79 | 6 |
| Example 7 | WQ | 5.33 ± 1.06 | 4 | 8.20 ± 0.96* | 12 | 10.85 ± 0.33 | 6 |
| Vehicle | EDL | 2.88 ± 0.21 | 6 | 8.93 ± 1.23 | 6 | 12.98 ± 1.12 | 6 |
| Example 7 | EDL | 9.05 ± 1.6* | 4 | 14.59 ± 1.09* | 12 | 15.44 ± 1.62 | 5 |
| Vehicle | Soleus | 2.27 ± 0.63 | 6 | 5.97 ± 1.05 | 6 | 13.13 ± 1.66 | 5 |
| Example 7 | Soleus | 2.51 ± 0.32 | 6 | 7.22 ± 1.40 | 12 | 16.51 ± 1.78 | 6 |

*represents significance (p < 0.05) compared to Vehicle DIO and is calculated by Two-Way ANOVA with a Dunnett's Comparison using JMP Software (V 5.0; SAS Institute, Cary, NC).

TABLE 11

Combined EDL and Soleus muscle weights from in vivo muscle glucose uptake experiment in male DIO mice treated with the molecule of Example 7.

| | Tissue | Weight (mg) | N |
|---|---|---|---|
| Vehicle | Soleus | 20.88 ± 0.87 | 17 |
| Example 7 | Soleus | 22.42 ± 0.50 | 18 |
| Vehicle | EDL | 24.42 ± 1.06 | 18 |
| Example 7 | EDL | 27.18 ± 0.89* | 18 |

*represents significance (p < 0.05) compared to Vehicle DIO and is calculated by One-Way ANOVA with a Dunnett's Comparison using GraphPad Prizm software (La Jolla, Ca).

In Vivo Leptin Receptor Deficient (C57Bl/6db−/db−) Mice—Chronic Dose Administration In vivo pharmacology studies investigating diabetes efficacy parameters are performed for the molecules of Examples 1, 2, 3, and 4, in the db/db mouse, a commonly used preclinical model of T2D. This mouse strain has a genetic mutation in the leptin receptor resulting in a lack of leptin signaling, an important adipokine for maintenance of food intake (Coleman DL. Obese and diabetes: two mutant genes causing diabetes-obesity syndromes in mice. *Diabetologia;* 14(3):141-8, (1978)). These mice become obese around 3 to 4 weeks on a normal rodent chow diet. They demonstrate elevations in plasma insulin and blood glucose, and display lowering of blood glucose in response to a number of insulin sensitizing agents. Therefore, the purpose of this study is to assess the ability to improve insulin sensitivity and subsequently lower plasma glucose.

Male db/db (BKS.Cg-+ Lepr$^{db}$/+Lepr$^{db}$/OaHlisd) (Harlan Indianapolis) mice 5-6 weeks old are housed 3-4 per cage and maintained on water bottles and 5008 chow (LabDiet; St Louis) for 2 weeks in the vivarium and on a normal light cycle prior to experiment start. Assessment of body weight, food consumption and other serum parameters are determined as explained above in the in vivo DIO Model—chronic dose administration, with the exception of food consumption which is averaged over each cage of animals (3-4 animals per cage; 2 cages per treatment). Percent body weight change is the percent change at end of study from the day 1 body weight.

On study day 1 mice are lightly restrained and the tail is resected using a clean scalpel. One drop of blood is placed on a glucose test strip and analyzed using an accuCheck blood glucose meter (Roche, Indianapolis). The animals are then randomized based on blood glucose into treatment groups by block randomization. Animals are given a single subcutaneous injection of the indicated treatment (4 day studies) or dosed once every three days of experiment (starting on day 1; 14 and 16 day studies) at a volume of 10 ml/kg in either 20 mM Tris HCl pH 8 or 20 mM citrate pH7. Vehicle control animals are injected with a similar volume of this solution. The solutions are kept in sterile capped vials stored at 4° C. for the duration of the study. Each day of the study (16 day) or each dosing day (14 day study) just prior to dosing animals are bled for determination of blood glucose as described below. Animals are sacrificed by $CO_2$ asphyxiation after glucose measurement on either day 4, 14 or 16 (based on study length).

Glucose AUC (from 0, Trapazoid rule) and statistical significance (*=p>0.05 vs. 0 dose: one way ANOVA Dunnett's post hoc) are calculated using GraphPad Prizm software (La Jolla, Ca).

Tables 12, 13, and 14 below show data corresponding to each of the above measurements. The data are represented as the arithmetic mean with SEM.

The data in Table 12 demonstrate that Examples 1-3 significantly lower blood glucose AUC measured over 4 days following a single injection. The data in Table 12 and 13 demonstrate that Examples 1-3 induced a significant decrease in body weight after being administered by s.c. administration for 4 (one injection) or 13 (injected on days 1, 4, 7, 10 and 13 of study days). Table 14 below demonstrates that Example 4 significantly reduces both body weight and glucose AUC (dosed on day 1, 4, 7, 10, and 13 of study) in a 16 day study in db/db mice. The significant glucose and body weight lowering effects of Example 4 produced a calculated $ED_{50}$ of 13.04 nmol/kg and 30.16 nmol/kg respectively.

TABLE 12

In vivo chronic dose administration in male db/db mice.

| | 4 day, 1 injection ||||||
|---|---|---|---|---|---|---|
| | Example 1 || Example 2 || Example 3 ||
| Dose | 0 mg/kg (n = 7) | 0.6 mg/kg (n = 7) | 0 mg/kg (n = 6) | 0.6 mg/kg (n = 6) | 0 mg/kg (n = 6) | 0.6 mg/kg (n = 6) |
| Body weight change (% change ± SEM) | 0.7 ± 1.2 | −5 ± 0.22* | 4.5 ± 0.42 | −1.9 ± 0.31* | 0.23 ± 0.44 | −4.7 ± 0.59* |
| Blood glucose AUC (mg/dL × day$^{-1}$ ± SEM) | 1331 ± 44 | 910 ± 41* | 1235 ± 59 | 760 ± 24 | 1185 ± 120 | 866 ± 48* |

*represents significance (p < 0.05) compared to Vehicle and is calculated by One-Way ANOVA with a Dunnett's post hoc using GraphPad Prism Software (GraphPad Software, Inc., La Jolla, CA).

TABLE 13

In vivo chronic dose administration in male db/db mice.

| | 14 day, 5 injections | | | | | |
|---|---|---|---|---|---|---|
| | Example 1 | | | Example 2 | | |
| Dose | 0 mg/kg (n = 5) | 0.3 mg/kg (n = 5) | 0.6 mg/kg (n = 5) | 0 mg/kg (n = 5) | 0.3 mg/kg (n = 5) | 0.6 mg/kg (n = 5) |
| Body weight change (% change ± SEM) | 14 ± 1.1 | 11 ± 1.2 | 2.7 ± 2.2* | 14 ± 1.1 | 6.8 ± 1.3* | 9.7 ± 1 |
| Blood glucose AUC (mg/dL × day$^{-1}$ ± SEM) | 5413 ± 386 | 4705 ± 147 | 4409 ± 321 | 5413 ± 386 | 4762 ± 174 | 4385 ± 144 |

*represents significance ($p < 0.05$) compared to Vehicle and is calculated by One-Way ANOVA with a Dunnett's post hoc using GraphPad Prism Software (GraphPad Software, Inc., La Jolla, CA).

TABLE 14

In vivo chronic dose administration in male db/db mice.

| | 16 day, 5 injections | | | | | | |
|---|---|---|---|---|---|---|---|
| | Example 4 | | | | | | |
| Dose | 0 nmol/kg (n = 5) | 2.4 nmol/kg (n = 5) | 7.2 nmol/kg (n = 5) | 24 nmol/kg (n = 5) | 72 nmol/kg (n = 5) | 144 nmol/kg (n = 5) | ED50 nmol/kg |
| Body weight change (% change ± SEM) | 9.3 ± 1.1 | 9.7 ± 2.3 | 8.1 ± 1.2 | 6.0 ± 1.7 | 6.9 ± 1.0 | −3.4 ± 4.6* | Ambiguous |
| Blood glucose AUC (mg/dL × day$^{-1}$ ± SEM) | 7592 ± 303 | 7270 ± 191 | 6455 ± 484 | 5945 ± 621* | 5746 ± 424* | 5143 ± 199* | 14.52 |

*represents significance ($p < 0.05$) compared to Vehicle and is calculated by One-Way ANOVA with a Dunnett's post hoc using GraphPad Prism Software (GraphPad Software, Inc., La Jolla, CA).

These data demonstrates that the compounds outlined herein are capable of treating type II diabetes.

Chronic Kidney Disease—Hypertensive Nephropathy

A mouse remnant kidney model ("remnant") involving surgical reduction of ¾ of the entire renal mass is used as a preclinical model of hypertensive renal disease (*Kidney Int.* 64(1):350-5, (2003)). This model results in hypertension and modest albuminuria over time and also shows elevations in serum creatinine consistent with decreases in glomerular filtration rate (GFR) and thus represents the later stages of human chronic kidney disease (approximating stage 3).

Surgical reduction of renal mass (N=40 mice) or sham surgery is performed by Taconic, Inc. in male 129S6 mice at 8-9 weeks of age (obtained by Taconic, Inc.). Randomization into 5 equivalent groups of 8 remnant kidney mice is done at 15 weeks post-surgery by urine albumin to creatinine ratio (ACR) and body weight. Either 0.9% physiological saline with 20 mM citrate ("saline control") or different dose levels of the compound of Example 2 (7.2, 24, 72 and 144 nmol/kg) are dosed subcutaneously three times weekly beginning at 16 weeks of age for 2 weeks.

Study duration is 9 weeks. After 2 weeks of dosing, a necropsy is done on all groups except the 144 nmol/kg group of Example 2 which continues to be monitored for ACR for another 7 weeks to determine the durability of the effects of the compound of Example 2 on urine ACR.

For all groups except the 144 nmol/kg group of Example 2, the endpoints of the study are body weight, kidney weight, heart weight, serum creatinine and urine ACR. For the 144 nmol/kg group of Example 2, the endpoints are body weight and urine ACR. There are no deaths during the study.

Body weight is determined at baseline and at termination with a Metler Toledo Balance. The heart and kidney are removed at necropsy and weighed on a Metler Toledo Balance. Blood (500 ul) is collected from the retro-orbital sinus at termination under isoflurane anesthesia. The clotted blood is centrifuged to obtain serum. Serum is analyzed for BUN and creatinine on a Roche Hitachi Modular Analytics P analyzer with reagents from Roche.

Table 15 below shows data corresponding to the above measurements. Data shown represent the arithmetic mean±the SEM for the parameters listed. All data represent an N value of 8 animals per group.

TABLE 15

In vivo measurement of body weight, heart weight, kidney weight, serum BUN and creatinine in a chronic kidney disease model of hypertensive nephropathy.

| Parameter | Sham | Saline | 7.2 nmol/kg Example 2 | 24 nmol/kg Example 2 | 72 nmol/kg Example 2 | 144 nmol/kg Example 2 |
|---|---|---|---|---|---|---|
| Initial Body Weight (g) | nd | 26.7 ± 0.8 | 26.0 ± 0.6 | 26.5 ± 0.9 | 25.7 ± 0.8 | 26.3 ± 0.8 |
| Final Body Weight (g) | 27.2 ± 0.7 | 27.9 ± 0.7 | 25.5 ± 1.2 | 24.0 ± 0.5 a | 24.8 ± 0.4 $^a$ | 24.5 ± 0.7 $^a$ |

TABLE 15-continued

In vivo measurement of body weight, heart weight, kidney weight, serum BUN
and creatinine in a chronic kidney disease model of hypertensive nephropathy.

| Parameter | Sham | Saline | 7.2 nmol/kg Example 2 | 24 nmol/kg Example 2 | 72 nmol/kg Example 2 | 144 nmol/kg Example 2 |
|---|---|---|---|---|---|---|
| Heart Weight (mg) | 142 ± 7 [a] | 195 ± 22 | 172 ± 11 | 142 ± 4 [a] | 151 ± 4 [a] | nd |
| Kidney Weight (mg) | 158 ± 4 [a] | 206 ± 6 | 204 ± 12 | 188 ± 8 | 195 ± 6 | nd |
| Serum BUN (mg/dL) | 33 ± 3 [a] | 57 ± 4 | 49 ± 3 | 44 ± 1 [a] | 46 ± 3 [a] | nd |
| Serum Creatinine (mg/dL) | 0.128 ± 0.004 [a] | 0.261 ± 0.018 | 0.240 ± 0.010 | 0.213 ± 0.008 [a] | 0.228 ± 0.014 | nd |

[a] denotes significant differences relative to the saline control group.
nd—denotes not determined.

The data in Table 15 demonstrate that the disease control shows significant increases in heart weight, kidney weight, serum BUN and serum creatinine relative to the sham control due to chronic kidney disease associated with surgically reduced renal mass. The data in Table 15 demonstrate that the compound of Example 2 significantly reduces body weight at all dose levels except the 7.2 nmol/kg relative to the saline control. The compound of Example 2 also significantly reduces heart weight at the 24 and 72 nmol/kg dose levels with no effect on kidney weight compared to the saline control group. The compound of Example 2 also significantly reduces serum BUN at the 24 and 72 nmol/kg dose levels and serum creatinine at the 24 nmol/kg dose level compared to the saline control group.

A spot urine collection to measure urine ACR is performed at baseline (−1), 1 and 2 weeks for the saline and all the dose levels of the compound of Example 2. Spot urine collections are also collected for the 144 nmol/kg dose level of Example 2 at 4, 6 and 9 weeks. Spot urine collections are done by placing mice on top of a 96 well polypropylene microplate to collect their urine over a 2 hr time period. The collected urine is placed on ice, centrifuged and subjected to albumin and creatinine analysis.

Urine albumin and creatinine are determined on a Roche Hitachi Modular Analytics P analyzer. Urine creatinine is determined with the Creatinine Plus reagent by Roche. For urine albumin, the Roche Microalbumin assay is modified to adapt the calibration curve for measuring urine albumin in mice. The assay limit of detection for albumin in urine is 4.9 mcg per ml. Sham mice do not have detectable albumin in the urine.

Table 16 shows data corresponding to measurements of urine ACR. The data shown are the arithmetic mean±the SEM at each time point. There are 8 mice per group.

TABLE 16

In vivo measurement of Albumin to Creatinine Ratio (ACR) in a chronic kidney
disease model of hypertensive nephropathy.

| | ACR (mcg/mg) | | | | | |
|---|---|---|---|---|---|---|
| | −1 week | 1 week | 2 week | 4 weeks | 6 weeks | 9 weeks |
| Saline | 2205 ± 411 | 1824 ± 480 | 1866 ± 720 | nd | nd | nd |
| Example 2 −7.2 nmol/kg | 2273 ± 576 | 1215 ± 321 | 630 ± 200 [a] | nd | nd | nd |
| Example 2 −24 nmol/kg | 2228 ± 410 | 636 ± 173 [a] | 246 ± 50 [a] | nd | nd | nd |
| Example 2 −72 nmol/kg | 2141 ± 416 | 1053 ± 230 | 304 ± 68 [a] | nd | nd | nd |
| Example 2 −144 nmol/kg | 2271 ± 500 | 889 ± 218 | 336 ± 85 [a] | 266 ± 52 | 328 ± 136 | 834 ± 412 |

[a] denotes significant differences relative to the saline control group.
nd—denotes not determined.

The data in Table 16 demonstrate that the compound of Example 2 significantly reduces urine ACR at the 24 nmol/kg dose level as early as 1 week of dosing and at all dose levels relative to the saline control after 2 weeks of dosing in the remnant kidney model. The data in Table 16 further demonstrate there is durability in the urine ACR lowering effect with the compound of Example 2 at 144 nmol/kg and that the reduction in ACR may not simply be hemodynamic in origin as the effect persists out to 7 weeks after the dosing of the compound of Example 2 is stopped.

Overall, these data demonstrate that the compound of Example 2 improves renal function under hypertensive conditions associated with chronic kidney disease with reductions in serum BUN, serum creatinine and urine ACR relative to the untreated controls.

All data are analyzed with JMP v.8.0 software (SAS Institute). Statistical analysis of albuminuria (ACR) was done by the following: 1) data were analyzed on log scale to stabilize variance over different treatment groups 2) data analysis was carried out in JMP v.8.0 using a ANOVA and a Dunnett's t test at each time point. All other data were evaluated by ANOVA with log transformed data if the data were skewed and a Students unpaired t test. Statistical outliers were removed prior to analysis. A P value of <0.05 was considered statistically significant.

This data demonstrate that the compounds outlined herein are capable of treating chronic kidney disease caused by hypertensive nephropathy.

Chronic Kidney Disease—Hypertensive Nephropathy

A mouse remnant kidney model ("remnant") involving surgical reduction of ¾ of the entire renal mass is used as a preclinical model of hypertensive renal disease (*Kidney Int.* 64(1):350-5, (2003)). This model results in hypertension and modest albuminuria over time and also shows elevations in serum creatinine consistent with decreases in glomerular filtration rate (GFR) and thus represents the later stages of human chronic kidney disease (approximating stage 3).

Surgical reduction of renal mass (N=32 mice) (obtained by Taconic, Inc.) is performed by Taconic, Inc. in male 129S6 mice at 9-10 weeks of age. Randomization into 4 equivalent groups of 8 remnant kidney mice is done at 17 weeks post-surgery by urine albumin to creatinine ratio (ACR) and body weight. Either 0.9% physiological saline for injection ("saline control") or different dose levels of Example 4 (2.6, 7.2 and 24 nmol/kg, Lot #BCA-BE03935-019) are dosed subcutaneously three times weekly beginning at 18 weeks post-surgery.

Study duration is 8 weeks. An intermittent dosing strategy is used as Example 4 is administered only during the first two weeks and then again during the fourth week of the study, thus there are periods of time during the study in which there is no exposure of the animals to Example 4. This is done to determine if effects of the compound of Example 4 on albuminuria are simply hemodynamic driven or if there are longer lasting effects on kidney function.

For all groups, the endpoints for the study are body weight, kidney weight, heart weight, albuminuria, serum creatinine and renal pathology scores for pelvic dilation, tubular changes, tubular protein, tubular regeneration, glomerular changes, interstitial inflammation, interstitial fibrosis, Masson's score and a PAS score. There is one death in the 2.6 nmol/kg dose group of Example 4 during the study.

Body weight is determined at baseline and at termination with a Metler Toledo Balance.

The heart and kidney are removed at necropsy and weighed on a Metler Toledo Balance. Blood (500 ul) is collected from the retro-orbital sinus at termination under isoflurane anesthesia. The clotted blood is centrifuged to obtain serum. Serum is analyzed for creatinine on a Roche Hitachi Modular Analytics P analyzer with reagents from Roche.

Table 17 below shows data corresponding to the above measurements. Data shown represent the arithmetic mean±the SEM for the parameters listed. All data represent an N value of 7-8 animals per group.

TABLE 17

In vivo measurement of body weight, heart weight, kidney weight and serum creatinine in a chronic kidney disease model of hypertensive nephropathy.

| Parameter | Saline | 2.6 nmol/kg Example 4 | 7.2 nmol/kg Example 4 | 24 nmol/kg Example 4 |
|---|---|---|---|---|
| Initial Body Weight (g) | 29.7 ± 0.8 | 32.3 ± 0.9 | 30.1 ± 1.0 | 30.6 ± 0.6 |
| Final Body Weight (g) | 30.9 ± 0.8 | 31.8 ± 1.1 | 29.8 ± 1.0 | 31.6 ± 0.6 |
| Heart Weight (mg) | 239 ± 17 | 203 ± 8 | 203 ± 10 | 205 ± 8 |
| Kidney Weight (mg) | 289 ± 9 | 280 ± 13 | 277 ± 14 | 310 ± 8 |
| Serum Creatinine (mg/dL) | 0.224 ± 0.010 | 0.220 ± 0.013 | 0.201 ± 0.008 | 0.188 ± 0.013 [a] |

[a] denotes significant differences relative to the saline control group

The data in Table 17 demonstrate that that the compound of Example 4 shows no significant effects on body weight, heart weight or kidney weight, although there is a trend for lower heart weight with the compound of Example 4. The compound of Example 4 at the 24 nmol/kg dose level significantly reduces serum creatinine relative to the saline group.

Measurement of Albuminuria

A spot urine collection to measure urine albumin to creatinine ratio (ACR) is performed at baseline, 1, 2, 4, 6 and 8 weeks of dosing for the saline and all of the Example 4 dose groups. Spot urine collections are done by placing mice on top of a 96 well polypropylene microplate to collect their urine over a 2 hr time period. The collected urine is placed on ice, centrifuged and subjected to albumin and creatinine analysis.

Urine albumin and creatinine are determined on a Roche Hitachi Modular Analytics P analyzer. Urine creatinine is determined with the Creatinine Plus reagent by Roche. For urine albumin, the Roche Microalbumin assay is modified to adapt the calibration curve for measuring urine albumin in mice.

Table 18 shows data corresponding to measurements of albuminuria. The data shown are the arithmetic mean±the SEM at each time point. There are 9-10 mice per group.

TABLE 18

In vivo measurement of Albumin to Creatinine Ratio (ACR) in a chronic kidney disease model of hypertensive nephropathy for 8 weeks.

| | ACR (mcg/mg) | | | | | |
|---|---|---|---|---|---|---|
| | −1 week | 1 week | 2 week | 4 weeks | 6 weeks | 8 weeks |
| Saline | 1586 ± 242 | 909 ± 232 | 1296 ± 437 | 1992 ± 585 | 2415 ± 732 | 2902 ± 1236 |
| Example 4 @ 2.6 nmol/kg | 1617 ± 429 | 618 ± 147 | 254 ± 98 [a] | 245 ± 121 [a] | 358 ± 143 [a] | 687 ± 108 |
| Example 4 @ | | | | | | |

TABLE 18-continued

In vivo measurement of Albumin to Creatinine Ratio (ACR) in a chronic kidney disease model of hypertensive nephropathy for 8 weeks.

| | ACR (mcg/mg) | | | | | |
|---|---|---|---|---|---|---|
| | −1 week | 1 week | 2 week | 4 weeks | 6 weeks | 8 weeks |
| 7.2 nmol/kg | 1599 ± 298 | 540 ± 188 | 206 ± 41 [a] | 176 ± 110 [a] | 169 ± 17 [a] | 479 ± 87 [a] |
| Example 4 @ 24 nmol/kg | 1792 ± 728 | 415 ± 77 | 123 ± 35 [a] | 73 ± 22 [a] | 175 ± 73 [a] | 278 ± 161 [a] |

[a] denotes significant differences relative to the saline control group.

The data in Table 18 demonstrate that the compound of Example 4 significantly reduces albuminuria at all dose levels relative to the saline control in the remnant kidney model. The data in Table 18 further demonstrate there is a dose dependent effect on albuminuria relative to the saline control group as early as 1 week of dosing with the compound of Example 4 that results in a return of albuminuria to near normal values after only 2 weeks of dosing at the highest dose level of the compound of Example 4. The data further demonstrate that the effect of the compound of Example 4 on albuminuria may not simply be hemodynamic in origin as the effect persists at the 6 and 8 week time points when the compound of Example 4 is no longer present based on the pharmacokinetic properties of the compound of Example 4.

Overall, these data demonstrate that the compound of Example 4 improves renal function under hypertensive conditions with reductions in serum creatinine and albuminuria that are associated with chronic kidney disease.

Renal Pathology

Remnant kidneys are removed at study termination, fixed in formalin and processed for paraffin sectioning according to standard methodology. Sections of kidney are evaluated for renal lesions by a board certified pathologist. Tubular protein, tubular regeneration, glomerular sclerosis, peri-glomerular fibrosis/inflammation, interstitial inflammation and interstitial fibrosis are semi-quantitatively scored using the following scale: none (0), minimal (1), slight (2), moderate (3), marked (4) and severe (5). Pathology scores are obtained with H&E, Masson's Trichrome and PAS stained sections.

Table 19 shows data corresponding to measurements of renal pathology. The data shown are the arithmetic mean±the SEM for each parameter. There are 7-8 mice per group.

TABLE 19

In vivo measurement of renal pathology in a hypertensive chronic kidney disease model.

| Parameter | Saline | Example 4 2.6 nmol/kg | Example 4 7.2 nmol/kg | Example 4 24 nmol/kg |
|---|---|---|---|---|
| Tubular protein | 1.3 ± 0.3 | 0.4 ± 0.2 [a] | 0.1 ± 0.1 [a] | 0.0 ± 0.0 [a] |
| Tubular regeneration | 1.4 ± 0.3 | 0.9 ± 0.2 | 0.6 ± 0.2 [a] | 0.3 ± 0.2 [a] |
| Glomerular sclerosis | 1.3 ± 0.4 | 0.4 ± 0.2 | 0.5 ± 0.3 | 0.3 ± 0.2 [a] |
| Peri-glomerular fibrosis/inflammation | 1.1 ± 0.4 | 0.3 ± 0.2 | 0.4 ± 0.2 | 0.3 ± 0.2 |
| Interstitial Fibrosis | 1.6 ± 0.3 | 1.0 ± 0.0 [a] | 0.9 ± 0.1 [a] | 0.8 ± 0.2 [a] |
| Interstitial Inflammation | 1.3 ± 0.4 | 0.7 ± 0.2 | 0.6 ± 0.2 | 0.4 ± 0.2 [a] |

[a] denotes significant differences relative to the saline control group.

The data in Table 19 demonstrate that the compound of Example 4 significantly reduces renal pathology at all dose levels relative to the saline control for tubular protein and interstitial fibrosis in the remnant kidney model. The data in Table 19 further demonstrate that the compound of Example 4 shows significant reductions in tubular regeneration, glomerular sclerosis, and interstitial inflammation at the highest dose level relative to the saline control group. These data demonstrate that the improvement in renal function with the compound of Example 4 in this model is accompanied by significant improvements in renal structure with reductions in renal pathology due to hypertensive renal disease.

Statistical Methods

Pathology data are statistically evaluated with R software by fitting an ordered logit model to the categorical scores, and then comparing the differences between different treatment groups. Statistical analysis of albuminuria (ACR) is done with R software by the following: 1) data are analyzed on log scale to stabilize variance over different treatment groups, 2) data analysis is carried out using a mixed model with treatment group, time and their interactions as model terms, plus baseline ACR is included as covariate, 3) observations from each animal at different times are treated as repeated measurements using a CS covariance structure and 4) the test p values are not adjusted for multiple testing. All other data are evaluated by ANOVA with log transformed data and a Students unpaired t test with JMP v.8.0 software (SAS Institute). Statistical outliers were removed prior to analysis. A P value of <0.05 was considered statistically significant.

This data demonstrate that the compounds outlined herein are capable of treating chronic kidney disease caused by hypertensive nephropathy.

The Effects of Long Acting Urocortin 2 on Blood Pressure Regulation in SHR Model Male spontaneously hypertensive rats (SHR/NCrl, Charles River Laboratories, Inc.) were implanted with Data Science International transmitters (TA11PA-C40) for blood pressure and heart rate data collection. All SHR were allowed to recover from the surgical implantation procedure for at least 2 weeks prior to the initiation of the experiments. During the monitoring phase (Day−1 to Day21), cardiovascular parameters (mean arterial, systolic and diastolic pressure and heart rate) were continuously monitored via the radiotransmitter in conscious, freely moving and undisturbed SHR in their individual home cages. The telemetry data from the DSI telemetry implants were then converted to a calibrated analog signal which inputs to a commercially produced data acquisition and analysis system (PONEMAH). All rats were individually housed in a temperature and humidity controlled room and are maintained on a 12 hour light/dark cycle.

SHR were randomized to groups according to mean arterial blood pressure (MAP) collected 7 days prior to dosing started. Rats were administered with vehicle (20 mM Tris-HCl buffer, pH8.0) or one of the 4 dose levels (2.4, 7.2, 24, 72 nmol/kg) of the compound of Example 4 twice weekly for 2 weeks with subcutaneous injection (injections on day 1, 4, 8 and 11). Blood pressure data were collected for one additional week to evaluate the blood pressure responses after withdrawal of Example 4 treatment.

The compound of Example 4 dose-dependently reduced blood pressure (Table 21, 22). Maximal MAP reduction was achieved at 24 hours post dosing. Blood pressure lowering effects of the compound of Example 4 were diminished with repeated dosing as demonstrated in the table comparing MAP after $1^{st}$ on day 1 and $4^{th}$ injection on day 11. After withdrawal of the compound of Example 4, blood pressure levels in all treatment groups were recovered and were not different from vehicle group.

Table 20 below shows the AUC results with P values for time periods (1-68 hrs) and (241-332 hrs).

Table 20: 1-way ANCOVA for AUC over 68 hours following the first dose (Day 1), and over 92 hours following the last does (Day 11).

TABLE 20

1-way ANCOVA for AUC over 68 hours following the first dose (Day 1), and over 92 hours following the last dose (Day 11).

| Day | Treatment | LS Mean Estimate | s.e. | Difference Estimate | s.e. | adjusted p-value |
|---|---|---|---|---|---|---|
| 1 (1-68 hrs) | 7.2 nmol/kg TA1 | 9313.8 | 103.17 | −732.1 | 146.26 | <.0001 |
| | 72 nmol/kg TA1 | 8829.7 | 109.22 | −1216.2 | 150.10 | <.0001 |
| | Control | 10045.9 | 102.28 | | | |
| 11 (241-332 hrs) | 7.2 nmol/kg TA1 | 13271.5 | 127.15 | −484.7 | 180.26 | 0.0385 |
| | 72 nmol/kg TA1 | 12971.8 | 134.60 | −784.4 | 184.98 | 0.0007 |
| | Control | 13756.2 | 126.06 | | | |

TABLE 21

MAP after $1^{st}$ or $4^{th}$ injections of vehicle or the compound of Example 4. N = 7-8/group. Hours indicate time post respective injection on day 1 or day 11.

| Treatment | 1-24 hrs MEAN | s.e. | 26-48 hrs MEAN | s.e. | 50-68 hrs MEAN | s.e. |
|---|---|---|---|---|---|---|
| MAP post injection on day 1 | | | | | | |
| Control | 149.9 | 3.4 | 149.3 | 2.4 | 147.3 | 3.3 |
| 72 nmol/kg | 128.6 | 2.3 | 130.4 | 3.5 | 143.1 | 4.0 |
| 24 nmol/kg | 137.6 | 3.3 | 131.8 | 2.5 | 137.2 | 2.3 |
| 7.2 nmol/kg | 140.1 | 4.2 | 140.6 | 3.4 | 144.3 | 4.0 |
| 2.4 nmol/kg | 149.0 | 2.5 | 147.6 | 3.1 | 148.6 | 2.8 |
| MAP (mean ± sem) post injection on day 11 | | | | | | |
| Control | 150.0 | 3.7 | 151.4 | 2.8 | 149.6 | 2.5 |
| 72 nmol/kg | 139.3 | 2.6 | 142.3 | 1.9 | 145.0 | 2.7 |
| 24 nmol/kg | 142.9 | 2.3 | 145.1 | 2.0 | 145.1 | 1.4 |
| 7.2 nmol/kg | 146.2 | 3.8 | 148.1 | 3.8 | 148.8 | 4.6 |
| 2.4 nmol/kg | 151.4 | 2.6 | 153.0 | 2.6 | 151.7 | 3.1 |

TABLE 22

1-way ANCOVA for AUC over 68 hours following the 1st injection (Day 1) or the 4th injection (Day 11), with baseline AUC (over 22 hours) as the covariate and comparison of each treatment to vehicle by Dunnett's test.

| Day | Treatment | LS Mean Estimate | s.e. | Difference from Control Estimate | s.e. | adjusted p-value |
|---|---|---|---|---|---|---|
| 1 (1-68 hrs) | Control | 10045.9 | 102.28 | | | |
| | 72 nmol/kg | 8829.7 | 109.22 | −1216.2 | 150.1 | <.0001 |
| | 24 nmol/kg | 9180.3 | 109.89 | −865.6 | 149.27 | <.0001 |
| | 7.2 nmol/kg | 9313.8 | 103.17 | −732.1 | 146.26 | <.0001 |
| | 2.4 nmol/kg | 9935.2 | 101.91 | −110.6 | 144.29 | 0.8613 |
| 11 (1-68 hrs) | Control | 10141.8 | 95.82 | | | |
| | 72 nmol/kg | 9432.6 | 102.32 | −709.3 | 140.62 | <.0001 |
| | 24 nmol/kg | 9778.3 | 102.95 | −363.5 | 139.84 | 0.0472 |
| | 7.2 nmol/kg | 9732.8 | 96.66 | −409 | 137.03 | 0.019 |
| | 2.4 nmol/kg | 10180.7 | 95.47 | 38.9 | 135.18 | 0.9954 |

The data in Tables 20-22 and statistical results in Table 20 demonstrate that the compound of Example 4 dose-dependently reduces blood pressure after the first injection. Maximal MAP reduction is achieved at 24 hours post dose. After withdrawal of the compound of Example 4, MAP in all treatment groups recovers and is not different from the vehicle group at 336 hrs.

MAP data are statistically evaluated with SAS software by 1-way ANCOVA for AUC over 68 hours following the first dose (Day 1), and over 92 hours following the last dose (Day 11).

Chronic Kidney Disease—Diabetic Nephropathy

The uninephrectomized db/db adeno-associated viral (AAV) renin model represents a progressive model of diabetic kidney disease with hypertension driven by an AAV renin transgene (*Am J Physiol Regul Integr Comp Physiol.* 309(5):R467-74, (2015)). This model exhibits overt albuminuria that progressively increases over time and also shows decreases in glomerular filtration rate (GFR) and thus represents the later stages of human diabetic nephropathy (approximating stage 3-4).

The uninephrectomy (UniNx) surgery on female db/db mice on a C57BLKS/J background (obtained from Harlan Laboratories) is performed by Harlan Laboratories at 4 weeks of age with removal of the right kidney to accelerate the diabetic kidney disease. Animals are received at 5 weeks of age and housed in micro-isolator cages at 3 mice per cage and are on a 12 hour light/dark cycle. All db/db mice are fed ad libitum with Purina special diet 5008 and allowed free access to autoclaved water.

Mice are acclimated for 7 weeks prior to administration of AAV Renin ($5 \times 10^9$ GC) intravenously by the retro-orbital sinus to induce persistent hypertension. Randomization by urine albumin to creatinine ratio (ACR), blood glucose and body weight is done at 15 weeks of age (a point at which renal disease and pathology are established in this model based on observations) into 2 groups of 12 saline control mice and 33 mice to receive Lisinopril treatment.

Dosing with Lisinopril (30 mg/L) begins at 16 weeks of age. After 2 weeks of Lisinopril treatment, the 33 mice are randomized by urine ACR, blood glucose and body weight into 4 groups (one group of 9 mice and 3 groups of 8 mice).

In the 4 groups of UniNx db/db AAV renin mice receiving Lisinopril treatment, either 0.9% physiological saline for injection ("saline control" N=9) or different dose levels of Example 4 (7.2, 24 or 72 nmol/kg, N=8 per dose level) are dosed at 0.2 mL s.c. per injection beginning at 18 weeks of age and continued 3 times weekly for 12 weeks. Albumin and creatinine are measured in urine with a Roche Hitachi Modular Analytics P analyzer with Roche reagents for detection of albumin and creatinine.

There were 6 deaths in the saline disease control group, 2 deaths in the Lisinopril plus saline group, 1 death in the Lisinopril plus 7.2 nmol/kg Example 4 group, 3 deaths in the Lisinopril plus 24 nmol/kg Example 4 group and 3 deaths in the Lisinopril plus 72 nmol/kg Example 4 group over the course of the study.

For all the groups, the parameters measured are body weight, kidney weight, heart weight, urine albumin to creatinine ratio, serum creatinine and renal pathology scores for mesangial matrix expansion, glomerular fibrosis, tubular regeneration, interstitial inflammation and interstitial fibrosis.

At 15 and 27 weeks of age, blood (30 to 50 uL) from all the UniNx db/db AAV Renin mice is obtained from the tail vein and dropped onto a Precision PCx blood glucose sensor electrode strip (Abbott Laboratories) for blood glucose determination with a MediSense Precision PCx glucometer (Abbott Laboratories). Blood glucose data is used to block the UniNx db/db mice into equivalent groups. Body weight is determined at baseline and at termination with a Metler Toledo Balance. The heart and kidney are removed at necropsy and weighed on a Metler Toledo Balance. Blood (500 ul) is collected from the retro-orbital sinus at termination under isoflurane anesthesia. The clotted blood is centrifuged to obtain serum. Serum is analyzed for creatinine on a Roche Hitachi Modular Analytics P analyzer with reagents from Roche.

Table 23 below shows data corresponding to measurements of body weight, blood glucose, kidney weight, heart weight and serum creatinine. Data shown represent the arithmetic mean±the SEM for the parameters listed. All data represent an N value of 5-8 animals per group except for the saline control group (N=6-12).

TABLE 23

In vivo measurement of body weight, blood glucose, kidney weight, heart weight and serum creatinine in a chronic kidney disease diabetic nephropathy model after 12 weeks.

| Parameter | Saline | Lisinopril plus Saline | Lisinopril plus 7.2 nmol/kg Example 4 | Lisinopril plus 24 nmol/kg Example 4 | Lisinopril plus 72 nmol/kg Example 4 |
|---|---|---|---|---|---|
| Initial Body Weight (g) | 62.3 ± 0.9 | 61.6 ± 2.3 | 66.7 ± 1.2 | 62.5 ± 1.2 | 62.0 ± 1.8 |
| Final Body Weight (g) | 56.0 ± 4.6 | 61.8 ± 4.9 | 68.8 ± 2.5 [a] | 59.1 ± 2.3 | 59.4 ± 4.3 |
| Initial Blood Glucose (mg/dL) | 339 ± 29 | 444 ± 48 | 333 ± 38 | 461 ± 19 | 455 ± 26 |
| Final Blood Glucose (mg/dL) | 202 ± 22 [b] | 466 ± 71 | 222 ± 15 [b] | 362 ± 55 | 260 ± 81 [b] |
| Kidney Weight (mgs) | 394 ± 22 | 392 ± 17 | 371 ± 18 | 345 ± 4 | 319 ± 13 [ab] |
| Heart Weight (mgs) | 326 ± 32 | 227 ± 26 [a] | 278 ± 12 | 231 ± 17 [a] | 255 ± 13 [a] |
| Serum Creatinine (mg/dL) | 0.188 ± 0.020 | 0.130 ± 0.070 [a] | 0.141 ± 0.009 | 0.118 ± 0.010 [a] | 0.348 ± 0.144 [b] |

[a] denotes significant differences relative to the saline control group.
[b] denotes significant differences relative to the Lisinopril alone group.

The data in Table 23 demonstrate that that the saline control group loses weight during the course of the study due to the effects of the renin transgene, while addition of Lisinopril prevents this effect on body weight. The compound of Example 4 at the 7.2 nmol/kg dose level added to Lisinopril significantly increases body weight relative to the saline control group. The loss of body weight in the saline control group also leads to a reduction in blood glucose at the end of the study while Lisinopril significantly prevents this effect on blood glucose. The addition of Example 4 at the 7.2 and 72 nmol/kg dose levels to Lisinopril results in a significant reduction in blood glucose relative to the Lisinopril alone group. Lisinopril alone has no effect on kidney weight relative to the saline control group, while addition of the compound of Example 4 at the dose level of 72 nmol/kg to Lisinopril results in a significant reduction of kidney weight relative to the saline control group and the Lisinopril alone group. The Lisinopril treatment alone as well as addition of the compound of Example 4 (24 and 72 nmol/kg) to Lisinopril results in a significant reduction of heart weight relative to the saline control group. The addition of the compound of Example 4 at the 24 nmol/kg dose level to Lisinopril as well as Lisinopril alone results in a significant reduction of serum creatinine relative to the saline control group. The addition of the compound of Example 4 at the 72 nmol/kg dose level to Lisinopril results in a significant increase in serum creatinine relative to the Lisinopril alone group.

Urine is collected by a spot collection method to collect urine over a 2-4 hr time period. An individual mouse is placed on top of a 96 well polypropylene microplate and then covered by a Plexiglas chamber with holes for breathing but no access to food or water. At the end of the time period, the urine is removed from the plate with a micropipette and placed on ice, centrifuged and subjected to albumin and creatinine analysis. Urine albumin, creatinine and glucose are determined on a Roche Hitachi Modular Analytics P analyzer. Urine creatinine is determined with the Creatinine Plus reagent by Roche. For urine albumin, the Roche Microalbumin assay is modified to adapt the calibration curve for measuring urine albumin in mice. Albuminuria was defined as albumin to creatinine ratio (ACR).

Table 24 below shows data corresponding to measurements of albuminuria. The data shown are the arithmetic mean±the SEM at each time point given as weeks of treatment with the compound of Example 4. There were 6-8 mice per group over the time points except for the saline group (N=5-12).

TABLE 24

In vivo measurement of Albumin to Creatinine Ratio (ACR) in a chronic kidney disease diabetic nephropathy model for 12 weeks.

| Weeks of treatment with Example 4) | Saline | Lisinopril plus Saline | Lisinopril plus 7.2 nmol/kg Example 4 | Lisinopril plus 24 nmol/kg Example 4 | Lisinopril plus 72 nmol/kg Example 4 |
|---|---|---|---|---|---|
| 0  | 25385 ± 3804    | 15203 ± 2835        | 15724 ± 2826         | 14329 ± 2306          | 15086 ± 2722          |
| 1  | 43984 ± 6671    | 16491 ± 3362        | 16336 ± 2761 $^a$    | 13219 ± 2137 $^a$     | 14706 ± 2352 $^a$     |
| 2  | 51871 ± 9107    | 16160 ± 4162 $^a$   | 7095 ± 1170 $^{ab}$  | 3612 ± 218 $^{ab}$    | 5918 ± 741 $^{ab}$    |
| 3  | 47313 ± 8939    | 13069 ± 3295 $^a$   | 9745 ± 1416 $^a$     | 9735 ± 2066 $^a$      | 9098 ± 1359 $^a$      |
| 6  | 41647 ± 5750    | 11584 ± 3132 $^a$   | 4164 ± 1271 $^{ab}$  | 3880 ± 713 $^{ab}$    | 4783 ± 769 $^{ab}$    |
| 8  | 49725 ± 5663    | 12484 ± 4626 $^a$   | 19633 ± 8562 $^a$    | 11852 ± 7132 $^a$     | 6156 ± 1165 $^a$      |
| 10 | 63009 ± 8448    | 20429 ± 4998 $^a$   | 13192 ± 5454 $^a$    | 5029 ± 1473 $^{ab}$   | 7935 ± 1029 $^{ab}$   |
| 12 | 38176 ± 6750 $^c$ | 19075 ± 6268 $^a$ | 26527 ± 8454 $^a$    | 7372 ± 3934 $^{abc}$  | 6257 ± 1649 $^{abc}$  |

$^a$ denotes significant differences relative to the saline control group.
$^b$ denotes significant differences relative to the Lisinopril plus saline group.
$^c$ denotes significant differences from Week 0 to Week 12 within the group.

The data in Table 24 demonstrate there is significant albuminuria in all the UniNx db/db AAV Renin groups at the time that the compound of Example 4 is initiated (week 0). The data in Table 24 show that Lisinopril treatment for 2 weeks prior to the dosing of the compound of Example 4 shows a trend for lower albuminuria relative to the saline control group at week 0. An overall statistical comparison of all ACR values shows that all of the Lisinopril groups are significantly improved for ACR relative to the saline group. The compound of Example 4 added to Lisinopril overall shows a further significant ACR lowering effect relative to Lisinopril alone at the 24 and 72 nmol/kg dose levels. The compound of Example 4 at the 24 and 72 nmol/kg dose levels also shows a significant reduction in ACR at week 12 relative to the respective baseline values at week 0, while the saline group shows a significant increase over this time and Lisinopril alone has no significant effect.

Measurement of Renal Pathology

Kidneys are removed at study termination, fixed in formalin and processed for paraffin sectioning according to standard methodology. Sections of kidney are evaluated for renal lesions by a board certified pathologist. The major renal pathologies in this diabetic model are increases in glomerular and interstitial fibrosis as well as increases in interstitial inflammation. Renal pathologies are semi-quantitatively scored using the following scale: none (0), minimal (1), slight (2), moderate (3), marked (4) and severe (5). Pathology scores are obtained using H&E, Masson's Trichrome and PAS stained sections.

Table 25 below shows data corresponding to measurements of renal pathology. Data shown represent the arithmetic mean±the SEM for the parameters listed. All data represent an N value of 4-7 animals per group.

TABLE 25

In vivo measurement of renal pathology in a chronic kidney disease diabetic nephropathy model after 12 weeks.

| Parameter | Saline | Lisinopril plus Saline | Lisinopril plus 7.2 nmol/kg Example 4 | Lisinopril plus 24 nmol/kg Example 4 | Lisinopril plus 72 nmol/kg Example 4 |
|---|---|---|---|---|---|
| Mesangial Matrix Expansion | 3.8 ± 0.3 | 2.1 ± 0.1 [a] | 1.2 ± 0.2 [ab] | 1.4 ± 0.2 [ab] | 1.6 ± 0.2 [a] |
| Glomerular Fibrosis | 2.8 ± 0.3 | 1.4 ± 0.2 [a] | 1.3 ± 0.2 [a] | 1.0 ± 0.0 [a] | 1.0 ± 0.3 [a] |
| Tubular Regeneration | 3.3 ± 0.5 | 2.0 ± 0.2 [a] | 1.0 ± 0.0 [ab] | 1.0 ± 0.3 [ab] | 1.0 ± 0.3 [ab] |
| Interstitial Inflammation | 2.3 ± 0.3 | 1.1 ± 0.3 [a] | 0.3 ± 0.2 [ab] | 0.2 ± 0.2 [ab] | 0.2 ± 0.2 [ab] |
| Interstitial Fibrosis | 2.5 ± 0.3 | 2.0 ± 0.3 | 1.0 ± 0.0 [ab] | 1.2 ± 0.2 [a] | 1.2 ± 0.2 [a] |

[a] denotes significant differences relative to the saline control group.
[b] denotes significant differences relative to the Lisinopril plus saline group.

The data in Table 25 demonstrate that Lisinopril plus saline treatment significantly reduces all of the renal pathology parameters relative to the saline control group with the exception of interstitial fibrosis. The data in Table 25 also demonstrate that Lisinopril plus the compound of Example 4 significantly reduces renal pathology for all the parameters relative to the saline control group. The data in Table 25 further demonstrate that the Lisinopril plus the compound of Example 4 significantly reduces renal pathology for mesangial matrix expansion, tubular regeneration, interstitial inflammation and interstitial fibrosis at a minimum of at least one dose level of Example 4 relative to the Lisinopril plus saline group.

Overall, these data demonstrate that the improvement in renal function obtained with Lisinopril plus the compound of Example 4 treatment in this diabetic nephropathy model is accompanied by significant improvements in renal structure with reductions in major renal pathologies due to diabetic hypertensive kidney disease. These data demonstrate that the compound of Example 4 is capable of treating chronic kidney disease caused by diabetes and hypertension.

Pathology data are statistically evaluated with R software by fitting an ordered logit model to the categorical scores, and then comparing the differences between different treatment groups. Statistical analysis of albuminuria (ACR) is done with R software by the following: 1) data are analyzed on log scale to stabilize variance over different treatment groups, 2) data analysis is carried out using a mixed model with treatment group, time and their interactions as model terms, plus baseline ACR is included as covariate, 3) observations from each animal at different times are treated as repeated measurements using a CS covariance structure and 4) the test p values are not adjusted for multiple testing. All other data are evaluated by ANOVA with log transformed data and a Students unpaired t test with JMP v.8.0 software (SAS Institute). Statistical outliers were removed prior to analysis. A P value of <0.05 was considered statistically significant.

This data demonstrate that the compounds outlined herein are capable of treating chronic kidney disease caused by hypertensive nephropathy.

As noted above, Table 1 provides in vitro activity for hCRHR2b for the compounds of Examples 1-7 (as well as this data for hUCN1 and hUCN2). Table 26 below provides the hCRHR2b in a cAMP assay for the compounds of Example 9. This data further shows that such compounds have CRHR2 agonist activity in a cAMP assay.

TABLE 26

| Compound No. | hCRHR2b Average EC50 (nM) |
|---|---|
| 21 | 5.25 (n = 2) |
| 22 | 1.20 (n = 2) |
| 23 | 17.9 (n = 2) |
| 24 | 25.3 (n = 2) |
| 25 | 63.5 (n = 2) |
| 26 | 15.62 (n = 2) |
| 27 | 31.54 (n = 2) |
| 28 | 83.2 (n = 2) |
| 29 | 64.7 (n = 2) |
| 30 | 12.4 (n = 2) |
| 31 | 3.20 (n = 2) |
| 32 | 9.18 (n = 2) |
| 33 | 8.68 (n = 2) |
| 34 | 4.54 (n = 2) |
| 35 | 404 (n = 2) |
| 36 | 330.9 (n = 2) |
| 37 | 24.09 (n = 2) |
| 38 | 2.33 (n = 2) |
| 39 | 26.99 (n = 2) |
| 40 | 55.86 (n = 4) |
| 41 | 207.0 (n = 4) |
| 42 | 500.2 (n = 2) |
| 43 | 12.56 (n = 4) |
| 44 | 13.37 (n = 2) |
| 45 | 27.69 (n = 4) |
| 46 | 11.67 (n = 4) |
| 47 | 4.56 (n = 5) |
| 48 | 3.61 (n = 5) |
| 49 | 2.86 (n = 2) |
| 50 | 3.56 (n = 2) |
| 51 | 2.42 (n = 2) |
| 52 | 1.16 (n = 2) |
| 53 | 4.01 (n = 2) |
| 54 | 4.26 (n = 2) |
| 55 | 1.51 (n = 2) |
| 56 | 1.17 (n = 3) |
| 57 | 3.65 (n = 2) |
| 58 | 3.79 (n = 2) |
| 59 | 2.62 (n = 2) |
| 60 | 2.55 (n = 4) |
| 61 | 2.50 (n = 2) |
| 62 | 4.50 (n = 2) |
| 63 | 1.30 (n = 2) |
| 64 | 1.63 (n = 2) |
| 65 | 1.24 (n = 2) |
| 66 | 1.45 (n = 2) |

NUMBERED EMBODIMENTS

1. A compound of the Formula:

wherein $X_1$ denotes that the I residue is modified by either acetylation or methylation at the N-terminus, wherein $X_2$ is L or T, wherein $X_3$ is L or I, wherein $X_4$ is Q or E, and wherein K* at position 29 is modified through conjugation to the epsilon-amino group of the K-side chain with a group of the formula —$X_5$—$X_6$, wherein $X_5$ is selected from the group consisting of:
one to four amino acids, one to four ([2-(2-Amino-ethoxy)-ethoxy]-acetyl) moieties, and combinations of one to four amino acids and one to four ([2-(2-Amino-ethoxy)-ethoxy]-acetyl) moieties, $X_6$ is a $C_{14}$-$C_{24}$ fatty acid (SEQ ID NO:16), or a pharmaceutically acceptable salt thereof.

2. The compound or salt of numbered embodiment 1, wherein $X_5$ is selected from the group consisting of: one to four E or γE amino acids, one to four ([2-(2-Amino-ethoxy)-ethoxy]-acetyl) moieties, and combinations of one to four E or γE amino acids and one to four ([2-(2-Amino-ethoxy)-ethoxy]-acetyl) moieties.

3. The compound or salt of numbered embodiment 2, wherein $X_5$ is a combination of one to four E or γE amino acids and one to four ([2-(2-Amino-ethoxy)-ethoxy]-acetyl) moieties.

4. The compound or salt of numbered embodiment 3, wherein $X_5$ is a combination of two to four γE amino acids and one to four ([2-(2-Amino-ethoxy)-ethoxy]-acetyl) moieties.

5. The compound or salt of numbered embodiments 1 to 4, wherein $X_5$ is a combination of two γE amino acids and two ([2-(2-Amino-ethoxy)-ethoxy]-acetyl) moieties.

6. The compound or salt of any one of numbered embodiments 1 to 5, wherein $X_6$ is a straight chain fatty acid of the formula CO—$(CH_2)_x$—$CO_2H$, wherein x is 16, 18, or 20.

7. The compound or salt of any one of numbered embodiments 1 to 6, wherein group of the formula —$X_5$—$X_6$ is ([2-(2-Amino-ethoxy)-ethoxy]-acetyl)$_2$-(γE)$_2$-CO—$(CH_2)_x$—$CO_2H$ where x is 16 or 18.

8. The compound or salt according to any one of numbered embodiments 1 to 7 wherein the terminal amino acid is amidated as a C-terminal primary amide.

9. The compound or salt according to any one of numbered embodiments 1 to 8 wherein $X_1$ denotes that the I residue is modified by acetylation at the N-terminus, $X_2$ is L, $X_3$ is L, $X_4$ is Q, and the group of the formula —$X_5$—$X_6$ is ([2-(2-Amino-ethoxy)-ethoxy]-acetyl)$_2$-(γE)$_2$-CO—$(CH_2)_x$—$CO_2H$ where x is 16 or 18 (SEQ ID NO:17).

10. The compound or salt according to any one of numbered embodiment 9 wherein x is 18 (SEQ ID NO:2).

11. The compound or salt according to any one of numbered embodiment 9 wherein x is 16 (SEQ ID NO:1).

12. The compound or salt according to any one of numbered embodiments 1 to 8 wherein $X_1$ denotes that the I residue is modified by methylation at the N-terminus, $X_2$ is L, $X_3$ is L, $X_4$ is Q, and the group of the formula —$X_5$—$X_6$ is ([2-(2-Amino-ethoxy)-ethoxy]-acetyl)$_2$-(γE)$_2$-CO—$(CH_2)_{18}$—$CO_2H$ (SEQ ID NO:4).

13. The compound or salt according to any one of numbered embodiments 1 to 8 wherein $X_1$ denotes that the I residue is modified by methylation at the N-terminus, $X_2$ is L, $X_3$ is L, $X_4$ is Q, and the group of the formula —$X_5$—$X_6$ is ([2-(2-Amino-ethoxy)-ethoxy]-acetyl)$_2$-(γE)$_2$-CO—$(CH_2)_{16}$—$CO_2H$ (SEQ ID NO:3).

14. The compound or salt according to any one of numbered embodiments 1 to 8 wherein $X_1$ denotes that the I residue is modified by methylation at the N-terminus, $X_2$ is T, $X_3$ is L, $X_4$ is E, and the group of the formula —$X_5$—$X_6$ is ([2-(2-Amino-ethoxy)-ethoxy]-acetyl)$_2$-(γE)$_2$-CO—$(CH_2)_{18}$—$CO_2H$ (SEQ ID NO:5).

15. The compound or salt according to any one of numbered embodiments 1 to 8 wherein $X_1$ denotes that the I residue is modified by methylation at the N-terminus, $X_2$ is L, $X_3$ is L, $X_4$ is E, and the group of the formula —$X_5$—$X_6$ is ([2-(2-Amino-ethoxy)-ethoxy]-acetyl)$_2$-(γE)$_2$-CO—$(CH_2)_{18}$—$CO_2H$ (SEQ ID NO:6).

16. The compound or salt according to any one of numbered embodiments 1 to 8 wherein $X_1$ denotes that the I residue is modified by methylation at the N-terminus, $X_2$ is T, $X_3$ is I, $X_4$ is E, and the group of the formula —$X_5$—$X_6$ is ([2-(2-Amino-ethoxy)-ethoxy]-acetyl)$_2$-(γE)$_2$-CO—$(CH_2)_{18}$—$CO_2H$ (SEQ ID NO:7).

17. A pharmaceutical composition comprising a compound according to any one of numbered embodiments 1 to 16 and one or more pharmaceutically acceptable carriers, diluents, and excipients.

18. A method for treating type II diabetes in a patient comprising administering to a patient in need of such treatment an effective amount of a compound or salt according to any one of numbered embodiments 1 to 16.

19. The method of numbered embodiment 18, wherein the administering to a patient in need of such treatment an effective amount of a compound or salt is combined with diet and exercise.

20. A method for treating chronic kidney disease in a patient comprising administering to a patient in need of such treatment an effective amount of a compound or salt according to any one of numbered embodiments 1 to 16.

21. The method according to numbered embodiment 20 wherein the chronic kidney disease is caused by diabetic nephropathy.

22. The method according to numbered embodiment 20 wherein the chronic kidney disease is caused by hypertensive nephropathy.

23. The methods according to any one of numbered embodiments 19 to 22, wherein the administration of the compound or salt to the patient in need of such treatment is subcutaneous.

24. A compound or salt according to any one of numbered embodiments 1 to 16 for use in therapy.

25. A compound or salt according to any one of numbered embodiments 1 to 16 for use in the treatment of type II diabetes.

26. A compound or salt according to any one of numbered embodiments 1 to 16 for use in the treatment of chronic kidney disease.

27. A compound or salt for use according to any one of numbered embodiments 24 to 26 wherein the administration of the compound or salt is subcutaneous.

28. A compound of the Formula:

wherein $X_1$ denotes that the I residue is modified by either acetylation or methylation at the N-terminus, wherein $X_2$ is L or T, wherein $X_3$ is L or I, wherein $X_4$ is Q or E (SEQ ID NO:18).

29. A compound of the formula:

```
                                                (SEQ ID NO: 68)
Ile Val Xaa Ser Leu Asp Val Pro Ile Xaa Leu Leu
1             5                   10

Gln Xaa Xaa Xaa Xaa Xaa Xaa Lys Xaa Xaa Lys Xaa
        15                  20

Lys Xaa Xaa Xaa Xaa Xaa Asn Ala Xaa Ile Leu Ala
25              30                  35

Xaa Val
```

Wherein:
Ile at position 1 may optionally be derivatized at the N-terminal amine with a methyl or an acetyl group;
Xaa at position 3 is Leu or Thr;
Xaa at position 10 is Gly or Lys;
Xaa at position 14 is Ile or Lys;
Xaa at position 15 is Leu or Lys;
Xaa at position 16 is Leu, Ile, or Lys;
Xaa at position 17 is Glu or Lys;
Xaa at position 18 is Gln or Lys;
Xaa at position 19 is Glu or Lys;
Xaa at position 21 is Gln or Lys;
Xaa at position 22 is Glu or Lys;
Xaa at position 24 is Glu or Lys;
Xaa at position 26 is Gln or Lys;
Xaa at position 27 is Gln or Lys;
Xaa at position 28 is Ala or Lys;
Xaa at position 29 is Thr or Lys;
Xaa at position 30 is Thr, Glu or Lys;
Xaa at position 33 is Gln, Arg, or Glu;
Xaa at position 37 is Gln, His, or Arg; and
Val at position 38 is optionally amidated at the C-terminal carboxyl;
provided that the epsilon-amine of Lys at exactly one of positions 10 and 14-30 is modified with —X5-X6, where X5 is 1 to 4 amino acids and/or 1 to 4 ([2-(2-Amino-ethoxy)-ethoxy]-acetyl) moieties and X6 is C14-C24 fatty acid; and
provided that if any of positions 10, 14-19, 21, 22, 24, and 26-30 is Lys then that position is the only one of positions 10, 14-19, 21, 22, 24, and 26-30 that is Lys; and
provided that when one of positions 10, 14-19, 21, 22, 24, and 26-30 is Lys, that Lys is modified with X5-X6.

Compounds

| Compound No. | Example No. | N-terminal modification | Peptide sequence | SEQ ID NO: | Modified Lysine position | C-terminal modification | Side chain on modified Lysine |
|---|---|---|---|---|---|---|---|
| 1 | 1 | Ac | IVLSLDVPIGLLQIL LEQEKQEKEKQQAKT NAQILAQV | 1 | 29 | amide | -([2-(2-Amino-ethoxy)-ethoxy]-acetyl)2-(γE)2-CO—(CH2)16—COOH |
| 2 | 2 | Ac | IVLSLDVPIGLLQIL LEQEKQEKEKQQAKT NAQILAQV | 2 | 29 | amide | -([2-(2-Amino-ethoxy)-ethoxy]-acetyl)2-(γE)2-CO—(CH2)18—CO2H |
| 3 | 3 | Me | IVLSLDVPIGLLQIL LEQEKQEKEKQQAKT NAQILAQV | 3 | 29 | amide | -([2-(2-Amino-ethoxy)-ethoxy]-acetyl)2-(γE)2-CO—(CH2)16—CO2H |
| 4 | 4 | Me | IVLSLDVPIGLLQIL LEQEKQEKEKQQAKT NAQILAQV | 4 | 29 | amide | -([2-(2-Amino-ethoxy)-ethoxy]-acetyl)2-(γE)2-CO—(CH2)18—CO2H |
| 5 | 5 | Me | IVTSLDVPIGLLQIL LEQEKQEKEKQQAKT NAEILAQV | 5 | 29 | amide | -([2-(2-Amino-ethoxy)-ethoxy]-acetyl)2-(γE)2-CO—(CH2)18—CO2H |
| 6 | 6 | Me | IVLSLDVPIGLLQIL LEQEKQEKEKQQAKT NAEILAQV | 6 | 29 | amide | -([2-(2-Amino-ethoxy)-ethoxy]-acetyl)2-(γE)2-CO—(CH2)18—CO2H |
| 7 | 7 | Me | IVTSLDVPIGLLQIL IEQEKQEKEKQQAKT NAEILAQV | 7 | 29 | amide | -([2-(2-Amino-ethoxy)-ethoxy]-acetyl)2---(γE)2-CO—(CH2)18—CO2H |
| — | — | Me or Ac | IVXSLDVPIGLLQIL XEQEKQEKEKQQAKT NAXILAQV X at 3 is L or T X at 16 is L or I X at 33 is Q or E | 8 | 29 | amide | -([2-(2-Amino-ethoxy)-ethoxy]-acetyl)2-(γE)2-CO—(CH2)x—CO2H where x is 16 or 18 |
| 9 | 8 | Me | IVLSLDVPIGLLQIL LEQEKQEKEKQQAKT NAQILAQV | 9 | 29 | amide | -γGlu-([2-(2-Amino-ethoxy)-ethoxy]-acetyl)2-(γE)2-CO—(CH2)18—COOH |

-continued

| Compound No. | Example No. | N-terminal modification | Peptide sequence | SEQ ID NO: | Modified Lysine position | C-terminal modification | Side chain on modified Lysine |
|---|---|---|---|---|---|---|---|
| 10 | 8 | Me | IVLSLDVPIGLLQIL LEQEKQEKEKQQAKT NAQILAQV | 10 | 29 | amide | -γE-([2-(2-Amino-ethoxy)-ethoxy]-acetyl)2-(γE)2-CO—(CH2)16—COOH |
| 11 | 8 | Me | IVLSLDVPIGLLQIL LEQEKQEKEKQQAKT NAQILAQV | 11 | 29 | amide | -γE-γE-γE-γE-CO—(CH2)18—COOH |
| 12 | 8 | Me | IVLSLDVPIGLLQIL LEQEKQEKEKQQAKT NAQILAQV | 12 | 29 | amide | -γE-γE-([2-(2-Amino-ethoxy)-ethoxy]-acetyl)-γE-γE-CO—(CH2)18—COOH |
| 13 | 8 | Me | IVLSLDVPIGLLQIL LEQEKQEKEKQQAKT NAQILAQV | 13 | 29 | amide | -γE-γE-([2-(2-Amino-ethoxy)-ethoxy]-acetyl)2-γ-γE-CO—(CH2)18—COOH |
| 14 | 8 | Me | IVLSLDVPIGLLQIL LEQEKQEKEKQQAKT NAQILAQV | 14 | 29 | amide | -γE-([2-(2-Amino-ethoxy)-ethoxy]-acetyl)-γE-γE-CO—(CH2)18—COOH |
| — | — | — | IVLSLDVPIGLLQIL LEQARARAAREQATT NARILARV | 15 | — | — | None |
| — | — | Me or Ac | IVXSLDVPIGLLQIL XEQEKQEKEKQQAKT NAXILAQV<br>X at 3 is L or T<br>X at 16 is L or I<br>X at 33 is Q or E | 16 | 29 | amide | As described herein. |
| 17 | — | Ac | IVLSLDVPIGLLQIL LEQEKQEKEKQQAKT NAQILAQV | 17 | 29 | amide | -([2-(2-Amino-ethoxy)-ethoxy]-acetyl)2-(γE)2-CO—(CH2)x—CO2H, where x is 16 or 18 |
| — | — | Me or Ac | IVXSLDVPIGLLQIL XEQEKQEKEKQQAKT NAXILAQV<br>X at 3 is L or T<br>X at 16 is L or I<br>X at 33 is Q or E | 18 | — | amide | None |
| — | — | — | EKQEKEKQ | 19 | — | — | None |
| — | — | — | IVLSLDVPIGLLQIL LEQEKQEKEKQQATT NARILARV | 20 | — | — | None |
| 21 | 9 | — | IVLSLDVPIGLLQKL LEQEKQEKEKQQATT NARILARV | 21 | 14 | amide | -γE-CO—(CH2)14—CH3 |
| 22 | 9 | — | IVLSLDVPIGLLQIK LEQEKQEKEKQQATT NARILARV | 22 | 15 | amide | -γE-CO—(CH2)14—CH3 |
| 23 | 9 | — | IVLSLDVPIGLLQIL LKQEKQEKEKQQATT NARILARV | 23 | 17 | amide | -γE-CO—(CH2)14—CH3 |
| 24 | 9 | — | IVLSLDVPIGLLQIL LEQKKQEKEKQQATT NARILARV | 24 | 19 | amide | -γE-CO—(CH2)14—CH3 |
| 25 | 9 | — | IVLSLDVPIGLLQIL LEQEKQEKEKQQATT NARILARV | 25 | 20 | amide | -γE-CO—(CH2)14—CH3 |

| Compound No. | Example No. | N-terminal modification | Peptide sequence | SEQ ID NO: | Modified Lysine position | C-terminal modification | Side chain on modified Lysine |
|---|---|---|---|---|---|---|---|
| 26 | 9 | — | IVLSLDVPIGLLQIL LEQEKKEKEKQQATT NARILARV | 26 | 21 | amide | -γE-CO—(CH2)14—CH3 |
| 27 | 9 | — | IVLSLDVPIGLLQIL LEQEKQKKEKQQATT NARILARV | 27 | 22 | amide | -γE-CO—(CH2)14—CH3 |
| 28 | 9 | — | IVLSLDVPIGLLQIL LEQEKQEKEKQQATT NARILARV | 28 | 23 | amide | -γE-CO—(CH2)14—CH3 |
| 29 | 9 | — | IVLSLDVPIGLLQIL LEQEKQEKKKQQATT NARILARV | 29 | 24 | amide | -γE-CO—(CH2)14—CH3 |
| 30 | 9 | — | IVLSLDVPIGLLQIL LEQEKQEKEKQQATT NARILARV | 30 | 25 | amide | -γE-CO—(CH2)14—CH3 |
| 31 | 9 | — | IVLSLDVPIGLLQIL LEQEKQEKEKQQATT NARILARV | 31 | 25 | amide | -γE-γE- CO—(CH2)14—CH3 |
| 32 | 9 | — | IVLSLDVPIGLLQIL LEQEKQEKEKQQATT NARILARV | 32 | 25 | amide | -([2-(2-Amino-ethoxy)-ethoxy]-acetyl)-γE-CO—(CH2)14—CH3 |
| 33 | 9 | — | IVLSLDVPIGLLQIL LEQEKQEKEKKQATT NARILARV | 33 | 26 | amide | -γE-CO—(CH2)14—CH3 |
| 34 | 9 | — | IVLSLDVPIGLLQIL LEQEKQEKEKKQATT NARILARV | 34 | 26 | amide | -γE-γE- CO—(CH2)14—CH3 |
| 35 | 9 | — | IVLSLDVPIGLLQIL LEQEKQEKEKQKATT NARILARV | 35 | 27 | amide | -γE-CO—(CH2)14—CH3 |
| 36 | 9 | — | IVLSLDVPIGLLQIL LEQEKQEKEKQQKTT NARILARV | 36 | 28 | amide | -γE-CO—(CH2)14—CH3 |
| 37 | 9 | — | IVLSLDVPIGLLQIL LEQEKQEKEKQQAKT NARILARV | 37 | 29 | amide | -γE-CO—(CH2)14—CH3 |
| 38 | 9 | — | IVLSLDVPIGLLQIL LEQEKQEKEKQQAKT NARILARV | 38 | 29 | amide | -γE-γE-CO—(CH2)14—CH3 |
| 39 | 9 | — | IVLSLDVPIGLLQIL LEQEKQEKEKQQATK NARILARV | 39 | 30 | amide | -γE-CO—(CH2)14—CH3 |
| 40 | 9 | — | IVLSLDVPIGLLQKL LEQEKQEKEKQQATT NAQILAHV | 40 | 14 | amide | -([2-(2-Amino-ethoxy)-ethoxy]-acetyl)2-γE-γE-CO—(CH2)16—COOH |
| 41 | 9 | — | IVLSLDVPIGLLQIK LEQEKQEKEKQQATT NAQILAHV | 41 | 15 | amide | -([2-(2-Amino-ethoxy)-ethoxy]-acetyl)2-γE-γE-CO—(CH2)16—COOH |
| 42 | 9 | — | IVLSLDVPIGLLQIL KEQEKQEKEKQQATT NAQILAHV | 42 | 16 | amide | -([2-(2-Amino-ethoxy)-ethoxy]-acetyl)2-γE-γE-CO—(CH2)16—COOH |
| 43 | 9 | — | IVLSLDVPIGLLQIL LKQEKQEKEKQQATT NAQILAHV | 43 | 17 | amide | -([2-(2-Amino-ethoxy)-ethoxy]-acetyl)2-γE-γE-CO—(CH2)16—COOH |

-continued

| Compound No. | Example No. | N-terminal modification | Peptide sequence | SEQ ID NO: | Modified Lysine position | C-terminal modification | Side chain on modified Lysine |
|---|---|---|---|---|---|---|---|
| 44 | 9 | — | IVLSLDVPIGLLQIL LEKEKQEKEKQQATT NAQILAHV | 44 | 18 | amide | -([2-(2-Amino-ethoxy)-ethoxy]-acetyl)2-γE-γE-CO—(CH2)16—COOH |
| 45 | 9 | — | IVLSLDVPIGLLQIL LEQEKKEKEKQQATT NAQILAHV | 45 | 21 | amide | -([2-(2-Amino-ethoxy)-ethoxy]-acetyl)2-γE-γE-CO—(CH2)16—COOH |
| 46 | 9 | — | IVLSLDVPIGLLQIL LEQEKQEKEKQQATT NAQILAHV | 46 | 25 | amide | -([2-(2-Amino-ethoxy)-ethoxy]-acetyl)2-γE-γE-CO—(CH2)16—COOH |
| 47 | 9 | — | IVLSLDVPIGLLQIL LEQEKQEKEKKQATT NAQILAHV | 47 | 26 | amide | -([2-(2-Amino-ethoxy)-ethoxy]-acetyl)2-γE-γE-CO—(CH2)16—COOH |
| 48 | 9 | — | IVLSLDVPIGLLQIL LEQEKQEKEKQQAKT NAQILAHV | 48 | 29 | amide | -([2-(2-Amino-ethoxy)-ethoxy]-acetyl)2-γE-γE-CO—(CH2)16—COOH |
| 49 | 9 | — | IVLSLDVPIKLLQIL LEQEKQEKEKQQATT NAQILAQV | 49 | 10 | amide | -([2-(2-Amino-ethoxy)-ethoxy]-acetyl)2-γE-γE-CO—(CH2)16—COOH |
| 50 | 9 | — | IVLSLDVPIGLLQIL LKQEKQEKEKQQATT NAQILAQV | 50 | 17 | amide | -([2-(2-Amino-ethoxy)-ethoxy]-acetyl)2-γE-γE-CO—(CH2)16—COOH |
| 51 | 9 | — | IVLSLDVPIGLLQIL LEQEKQEKEKKQATT NAQILAQV | 51 | 26 | amide | -([2-(2-Amino-ethoxy)-ethoxy]-acetyl)2-γE-γE-CO—(CH2)16—COOH |
| 52 | 9 | — | IVLSLDVPIGLLQIL LEQEKQEKEKQQAKT NAQILAQV | 52 | 29 | amide | -([2-(2-Amino-ethoxy)-ethoxy]-acetyl)2-γE-γE-CO—(CH2)16—COOH |
| 53 | 9 | — | IVLSLDVPIGLLQIL LKQEKQEKEKQQATE NAQILAQV | 53 | 17 | amide | ([2-(2-Amino-ethoxy)-ethoxy]-acetyl)2-γE-γE-CO—(CH2)16—COOH |
| 54 | 9 | — | IVLSLDVPIGLLQIL LEQEKQEKEKKQATE NAQILAQV | 54 | 26 | amide | -([2-(2-Amino-ethoxy)-ethoxy]-acetyl)2-γE-γE-CO—(CH2)16—COOH |
| 55 | 9 | — | IVLSLDVPIGLLQIL LEQEKQEKEKQQAKE NAQILAQV | 55 | 29 | amide | -([2-(2-Amino-ethoxy)-ethoxy]-acetyl)2-γE-γE-CO—(CH2)16—COOH |
| 56 | 9 | — | IVLSLDVPIGLLQIL LEQEKQEKEKQQAKE NAQILAQV | 56 | 29 | amide | -([2-(2-Amino-ethoxy)-ethoxy]-acetyl)2-γE-γE-CO—(CH2)16—COOH |
| 57 | 9 | Me | IVLSLDVPIGLLQIL LEQEKQEKEKQQAKE NAEILAQV | 57 | 29 | amide | -([2-(2-Amino-ethoxy)-ethoxy]-acetyl)-γE-γE-CO—(CH2)18—COOH |
| 58 | 9 | Me | IVLSLDVPIGLLQIL LEQEKQEKEKQQAKE NAEILAQV | 58 | 29 | amide | -γE -γE-CO—(CH2)18—COOH |
| 59 | 9 | Me | IVLSLDVPIGLLQIL LEQEKQEKEKQQAKE NAEILAQV | 59 | 29 | amide | -γE-([2-(2-Amino-ethoxy)-ethoxy]-acetyl)-γE-γE-CO—(CH2)18—COOH |
| 60 | 9 | Me | IVLSLDVPIGLLQIL LEQEKQEKEKQQAKT NAQILAQV | 60 | 29 | amide | -γE-([2-(2-Amino-ethoxy)-ethoxy]-acetyl)2-γE-γE-CO—(CH2)18—COOH |
| 61 | 9 | Me | IVLSLDVPIGLLQIL LEQEKQEKEKQQAKT NAQILAQV | 61 | 29 | amide | -γE-([2-(2-Amino-ethoxy)-ethoxy]-acetyl)-γE-γE-CO—(CH2)18—COOH |

| Compound No. | Example No. | N-terminal modification | Peptide sequence | SEQ ID NO: | Modified Lysine position | C-terminal modification | Side chain on modified Lysine |
|---|---|---|---|---|---|---|---|
| 62 | 9 | Me | IVLSLDVPIGLLQIL LEQEKQEKEKQQAKT NAQILAQV | 62 | 29 | amide | -γE-γE-([2-(2-Amino-ethoxy)-ethoxy]-acetyl)2-γE-γE-CO—(CH2)18—COOH |
| 63 | 9 | Me | IVLSLDVPIGLLQIL LEQEKQEKEKQQAKT NAQILAQV | 63 | 29 | amide | -γE-γE-([2-(2-Amino-ethoxy)-ethoxy]-acetyl)-γE-γE-CO—(CH2)18—COOH |
| 64 | 9 | Me | IVLSLDVPIGLLQIL LEQEKQEKEKQQAKT NAQILAQV | 64 | 29 | amide | -γE-γE-γE-γE-CO—(CH2)18—COOH |
| 65 | — | Me | IVTSLDVPIGLLQIL LEQEKQEKEKQQAKT NAQILAQV | 65 | 29 | | -γE-([2-(2-Amino-ethoxy)-ethoxy]-acetyl)2-γE-γE-CO—(CH2)18—COOH |
| 66 | 9 | Me | IVTSLDVPIGLLQIL LEQEKQEKEKQQAKT NAEILAQV | 66 | 29 | amide | -γE-([2-(2-Amino-ethoxy)-ethoxy]-acetyl)2-γE-γE-CO—(CH2)18—COOH |
| — | — | —, Me, Ac | IVXSLDVPIGLLQIL XEQEKQEKEKQQATX NAXILAXV X at position 3 is L or T X at position 16 is L or I X at position 30 is T or E X at position 33 is Q, R, or E X at position 37 is Q, H, or R | 67 | As described herein | As described herein | As described herein. |

As noted above, certain embodiments may be designed in which the patient is an animal, such as a cat. Below is a list of the sequences of various Urocortin 2 sequences found in humans and some animal species.

```
HUMAN      IVLSLDVPIGLLQILLEQARARAAREQATTNARILARVGHC :41

MOUSE      VILSLDVPIGLLRILLEQARYKAARNQAATNAQILAHV--- :38

RAT        VILSLDVPIGLLRILLEQARNKAARNQAATNAQILARV--- :38

ORANGUTAN  IVLSLDVPIGLLQILLEQARARAAREQATTNARILAHVG-- :39

DOG        IILSLDVPIGLLQILLEQARARASREQATTNARILAQVG-- :39

BOVINE     ITLSLDVPLGLLQILLEQARARAVREQAAANARILAHVGH- :40

HORSE      ITLSLDVPVGLLQILLEQVRARAAREQAAANARILAHVG-- :39

PIG        ITLSLDVPLGLLQILLEQARARAVREQAAANARILAHVG-- :39

ELEPHANT   ITLSLDVPLGLLQILLEQARIRAAREQAAANARILAHVG-- :39

FISH       ISLDVPTSILSVLIDIAKNQDMRTKAAANAELMARIG---- :37
```

Additionally, information about urocortin 2 for cats is found in the GENBANK database and is reproduced below:

```
GENBANK ACCESSION NUMBER XR_002150782 (VERSION XR_002150782.1)
    1 gctctgggtg ggatgggcag ggccttgggg gctgagtaga tccgggtatg ggttattgga 61 ggtctccgga tgtggagtct ctggctgctt ctctaccttg aggaccccat tctgcccctt 121 ctttgtccac gatctgctgc aagctccctc agacctgagg ctccccttt gtccctctgt 181 gttctctcca tgccttggta tccttatttt catcatgctg tctgtctctg gggtggctcc 241 agcctctttg tcttccagtc tccctctttt gctctgcctc catgtcctcc ctctcgtctt 301 tttccctctt ctccctcccc tccccaactg tacccatctc tacatctaga tccagaccta 361 gctgtgctct ctgtctcttt cactctcctt cttgctctct ccgtctccct ggccctgct 421 ctgtctggct gtcttgtgct ttcatctctg tctctcttat ctccgtccca tgcctggcct
```

-continued

```
 481 ctctaatctc tacctctctg tctccttccc ttggtctccc tctctctgtc tgtctacttt
 541 ccccgtctgc atctgtccat gcgccacggc tgcccagaac ccctgccctg agcctctttt
 601 ctcctcgcag cctgaccacg cgatgaccag gtgggctctg ctggtgctga tgatcctgac
 661 gtcgggcagg gccctgcttg tccccatgac ccctattcca gccttccagc tcctccctca
 721 gaaccctccc caagccactc cccgccctgt ggcctcagag agccctcag ccagcaccgt
 781 gggcccctcc actgcttggg ccacccctag ccctggcccc cgcccaggcc ccgcatcac
 841 tctctcactg gatgtcccca ttggcctcct gcggatctta ctggagcaag cccgagccag
 901 agctgtgagg gagcaggccg ctgccaacgc tcgcatcctg gcccatgttg gccgccgctg
 961 agcctcaggg cgggggtcac cctgaattag agacctggaa aggcagcagc agagcaggac
1021 gcactacatc tgggcacagt gcgcctggcc acagccccgt gcagtcactg ccatgtggtg
1081 tcatatcaca gctgagtgcc tcacagagcc acagtttgtt tggacagccc gggcattgcc
1141 atatcgggtg actgccaaat ggagtcttgc catacctgga gccacacaga cttacaatat
1201 gtctggacag cttggacact actgtggaat gtgactaccg tgtggagtct tgccatgtct
1261 gggtgcccca cagtcaaaga gcaagaatct ggacactgcc aatgtggcca ctcttgtgcc
1321 agttttagga acctcaacat aggagcccag tattgcatct cagacccatc cacctaagac
1381 cagacctgca ggtcttccct gcccccaaca ggtcaccaca caggggagtg caggctgagg
1441 gtcacatgca tgttttgtgc ttcatgaggc agcacccacc ccagaagaat ggggccgtca
1501 caggcatctc caggcatggg tgaccgtacg tggaaagtct gtggttgtga cagccttgcc
1561 ttgtgccctg cacacctggc ctcggccctt ggacacacga tgactcagga gagaggaggc
1621 tcgggctgct ggggctccgg tccagcccca tacctccttt gttgaattgt cccaagcaaa
1681 ctaaaatgtg ctcacctttc caagccttag tttcttcctc tgtaaagcag aatgatgcca
1741 ccaagcttct tgcaaacatt gagtgacggt gcacttgaag gttctagcac gcaggaagag
1801 ctcaataaat gtagtgactg ga
GENBANK ACCESSION NUMBER XM_006928725 (VERSION XM_006928725.2)
   1 gtccctctgt ccagccctgg tcactgttct gtgactctca gtgtccaact tgtccccaaa
  61 aaggagtaga cagagtggag gctgaggaca cgtcctcact gccccccag gaggggatga
 121 gtcagaggtg gggggctgct tcatgccgga gccgtgccca gctcctacct caggggctga
 181 gagagataaa tgggcccgga aggggcaga ggcccgacca cagcacagca ccgcctggtc
 241 ccagccgcgg gcagccctgg cggccccacc ttgctccaga agaggctgct gctgcctgac
 301 cacgcgatga ccaggtgggc tctgctggtg ctgatgatcc tgacgtcggg cagggccctg
 361 cttgtcccca tgacccctat tccagccttc agctcctcc ctcagaaccc tccccaagcc
 421 actccccgcc ctgtggcctc agagagcccc tcagccagca ccgtgggccc ctccactgct
 481 tgggccacc ctagccctgg ccccgccca ggccccgca tcactctctc actggatgtc
 541 cccattggcc tcctgcggat cttactggag caagcccgag ccagagctgt gagggagcag
 601 gccgctgcca acgctcgcat cctggcccat gttggccgcc gctgagcctc agggcgggg
 661 tcaccctgaa ttaggagacc tggaaggcag cagcagagca ggacgcacta catctgggca
 721 cagtgcgcct ggccacagcc ccgtgcagtc actgccatgt ggtgtcatat cacagctgag
 781 tgcctcacag agccacagtt tgtttggaca gcccgggcat tgccatatcg ggtgactgcc
 841 aaatggagtc ttgccatacc tggagccaca cagacttaca atatgtctgg acagcttgga
 901 cactactgtg gaatgtgact accgtgtgga gtcttgccat gtctgggtgc cccacagtca
 961 aagagcaaga atctggacac tgccaatgtg gccactcttg tgccagtttt aggaacctca
```

-continued

```
1021 acataggagc ccagtattgc atctcagacc catccaccta agaccagacc tgcaggtctt 1081 ccctgccccc aacaggtcac cacacagggg agtgcaggct gagggtcaca tgcatgtttt 1141 gtgcttcatg aggcagcacc caccccagaa gaatggggcc gtcacaggca tctccaggca 1201 tgggtgaccg tacgtggaaa gtctgtggtt gtgacagcct tgccttgtgg taggtgtacg 1261 tgtgatcggt gggtgcatct ctgctgtgg
```

Specific embodiments may be designed in which the molecules of SEQ. ID NOS. 1, 2, 3, 5, 6 and 7 are used to treat chronic kidney disease and/or diabetes in cats or other animals.

We claim:

1. A compound of the Formula:

$$X_1IVX_2SLDVPIGLLQILX_3EQEKQEKEKQQAK*TNAX_4ILAQV\text{-}NH_2 \quad \text{(Formula II)},$$

wherein $X_1$ denotes that the I residue is modified by either acetylation or methylation at the N-terminus, wherein $X_2$ is L or T, wherein $X_3$ is L or I, wherein $X_4$ is Q or E, wherein a modified K residue ("K*") at position 29 is modified through conjugation to the epsilon-amino group of the K-side chain with a group of the formula —$X_5$—$X_6$, wherein $X_5$ is selected from the group consisting of:
one to four more amino acids,
one to four ([2-(2-Amino-ethoxy)-ethoxy]-acetyl) moieties, and
combinations of one to four amino acids and one to four ([2-(2-Amino-ethoxy)-ethoxy]-acetyl) moieties, and wherein $X_6$ is a $C_{14}$-$C_{24}$ fatty acid (SEQ ID NO:16);
or a pharmaceutically acceptable salt thereof.

2. The compound or salt of claim 1, wherein X5 is selected from the group consisting of: one to four E or γE amino acids, one to four ([2-(2-Amino-ethoxy)-ethoxy]-acetyl) moieties, and combinations of one to four E or γE amino acids and one to four ([2-(2-Amino-ethoxy)-ethoxy]-acetyl) moieties.

3. The compound or salt of claim 2, wherein $X_5$ is a combination of one to four E or γE amino acids and one to four ([2-(2-Amino-ethoxy)-ethoxy]-acetyl) moieties.

4. The compound or salt of claim 3, wherein $X_5$ is a combination of two to four γE amino acids and one to four ([2-(2-Amino-ethoxy)-ethoxy]-acetyl) moieties.

5. The compound or salt of claim 3, wherein X5 is a combination of two γE amino acids and two ([2-(2-Amino-ethoxy)-ethoxy]-acetyl) moieties.

6. The compound or salt of claim 1, wherein $X_6$ is a straight chain fatty acid of the formula $CO-(CH_2)_x-CO_2H$, and wherein x is 16, 18, or 20.

7. The compound or salt of claim 1, wherein the group of the formula $-X_5-X_6$ is ([2-(2-Amino-ethoxy)-ethoxy]-acetyl)$_2$-(γE)$_2$-CO-(CH$_2$)$_x$-CO$_2$H, and wherein x is 16 or 18.

8. The compound or salt according to claim 1 wherein:
$X_1$ denotes that the I residue is modified by acetylation at the N-terminus;
$X_2$ is L;
$X_3$ is L;
$X_4$ is Q; and
the group of the formula $-X_5-X6$ is ([2-(2-Amino-ethoxy)-ethoxy]-acetyl)$_2$-(γE)$_2$-CO-(CH$_2$)$_x$-CO$_2$H where x is 16 or 18.

9. The compound or salt according to claim 8 wherein x is 18.

10. The compound or salt according to claim 8 wherein x is 16.

11. The compound or salt of claim 1, wherein: $X_1$ denotes that the I residue is modified by methylation at the N-terminus, $X_2$ is L, $X_3$ is L, $X_4$ is Q, and the group of the formula $-X_5-X_6$ is ([2-(2-Amino-ethoxy)-ethoxy]-acetyl)$_2$-(γE)$_2$-CO-(CH$_2$)$_{18}$-CO$_2$H.

12. The compound or salt according to claim 1 wherein:
$X_1$ denotes that the I residue is modified by methylation at the N-terminus;
$X_2$ is L;
$X_3$ is L;
$X_4$ is Q; and
the group of the formula $-X_5-X_6$ is ([2-(2-Amino-ethoxy)-ethoxy]-acetyl)$_2$-(γE)$_2$-CO-(CH$_2$)$_{16}$-CO$_2$H.

13. The compound or salt according to claim 1 wherein:
$X_1$ denotes that the I residue is modified by methylation at the N-terminus;
$X_2$ is T;
$X_3$ is L;
$X_4$ is E; and
the group of the formula $-X_5-X_6$ is ([2-(2-Amino-ethoxy)-ethoxy]-acetyl)$_2$-(γE)$_2$-CO-(CH$_2$)$_{18}$-CO$_2$H.

14. The compound or salt according to claim 1 wherein:
$X_1$ denotes that the I residue is modified by methylation at the N-terminus;
$X_2$ is L;
$X_3$ is L;
$X_4$ is E; and
the group of the formula $-X_5-X_6$ is ([2-(2-Amino-ethoxy)-ethoxy]-acetyl)$_2$-(γE)$_2$-CO-(CH$_2$)$_{18}$-CO$_2$H.

15. The compound or salt according to claim 1 wherein:
$X_1$ denotes that the I residue is modified by methylation at the N-terminus;
$X_2$ is T;
$X_3$ is
$X_4$ is E; and
the group of the formula $-X_5-X_6$ is ([2-(2-Amino-ethoxy)-ethoxy]-acetyl)$_2$-(γE)$_2$-CO-(CH$_2$)$_{18}$-CO$_2$H.

16. A compound or salt according to claim 1 for use in therapy.

17. A compound or salt according to claim 1 for use in the treatment of type II diabetes.

18. A compound or salt according to claim 1 for use in the treatment of chronic kidney disease.

19. A pharmaceutical composition comprising a compound or salt according to claim 1 and one or more pharmaceutically acceptable carriers, diluents, and excipients.

20. A method for treating type II diabetes in a patient comprising administering to a patient in need of such treatment an effective amount of a compound or salt according to claim 1.

21. A method for treating chronic kidney disease in a patient comprising administering to a patient in need of such treatment an effective amount of a compound or salt according to claim 1.

22. The method according to claim 21 wherein the chronic kidney disease is caused by diabetic nephropathy.

23. The method according to claim 21 wherein the chronic kidney disease is caused by hypertensive nephropathy.

24. The method according to claim 21, wherein the administration of the compound or salt to the patient in need of such treatment is subcutaneous.

* * * * *

UNITED STATES PATENT AND TRADEMARK OFFICE
CERTIFICATE OF CORRECTION

PATENT NO. : 10,894,817 B2  
APPLICATION NO. : 15/648542  
DATED : January 19, 2021  
INVENTOR(S) : Jorge Alsina-Fernandez, Lili Guo and John Lee Page 1 of 1

It is certified that error appears in the above-identified patent and that said Letters Patent is hereby corrected as shown below:

In the Claims

Column 139 Line 1: In Claim 2, delete "X5" and insert -- $X_5$ --, therefor.

Column 139 Line 14: In Claim 5, delete "X5" and insert -- $X_5$ --, therefor.

Column 139 Line 30: In Claim 8, delete "X6" and insert -- $X_6$ --, therefor.

Column 140 Line 20: In Claim 15, after "$X_3$ is" insert -- I; --.

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*

```
                          SEQUENCE LISTING

<160> NUMBER OF SEQ ID NOS: 68

<210> SEQ ID NO 1
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-Glu)2-CO-
      (CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 1

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 2
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (29)..(29)
<223> OTHER INFORMATION: Lys at position 29 is Lys which is chemically
      modified through conjugation to the epsilon-amino group of the Lys
      side-chain with ([2-(2-Amino-ethoxy)-ethoxy]-acetyl)2-(gamma-
      glu)2-CO-(CH2)18-CO2H
<220> FEATURE:
<221> NAME/KEY: MOD_RES
<222> LOCATION: (38)..(38)
<223> OTHER INFORMATION: Val at position 38 is amidated at the
      C-terminal carboxyl
```

<400> SEQUENCE: 2

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 3
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-
      (CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 3

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 4
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-
      (CH2)18-CO2H
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 4

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 5
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-
      (CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 5

Ile Val Thr Ser Leu Asp Val Pro Ile Gly Leu Leu Gln Ile Leu Leu
1               5                  10                  15

Glu Gln Glu Lys Gln Glu Lys Glu Lys Gln Gln Ala Lys Thr Asn Ala
            20                  25                  30

Glu Ile Leu Ala Gln Val
        35

<210> SEQ ID NO 6
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-
      (CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 6

Ile Val Leu Ser Leu Asp Val Pro Ile Gly Leu Leu Gln Ile Leu Leu
1               5                  10                  15

Glu Gln Glu Lys Gln Glu Lys Glu Lys Gln Gln Ala Lys Thr Asn Ala
            20                  25                  30

Glu Ile Leu Ala Gln Val
        35

<210> SEQ ID NO 7
<211> LENGTH: 38
<212> TYPE: PRT
<213> ORGANISM: Artificial Sequence
<220> FEATURE:

```
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-
      (CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 7

Ile Val Thr Ser Leu Asp Val Pro Ile Gly Leu Leu Gln Ile Leu Ile
1               5                   10                  15

Glu Gln Glu Lys Gln Glu Lys Glu Lys Gln Gln Ala Lys Thr Asn Ala
            20                  25                  30

Glu Ile Leu Ala Gln Val
        35

<210> SEQ ID NO 8
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: METHYLATION
<220> FEATURE:
<221> NAME/KEY: MISC_FEATURE
<222> LOCATION: (3)..(3)
<223> OTHER INFORMATION: Xaa at position 3 is Leu or Thr
<220> FEATURE:
<221> NAME/KEY: MISC_FEATURE
<222> LOCATION: (16)..(16)
<223> OTHER INFORMATION: Xaa at position 16 is Leu or Ile
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-(CH2)x-
      CO2H where x is 16 or 18
<220> FEATURE:
<221> NAME/KEY: MISC_FEATURE
<222> LOCATION: (33)..(33)
<223> OTHER INFORMATION: Xaa at position 33 is Gln or Glu
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 8

Ile Val Xaa Ser Leu Asp Val Pro Ile Gly Leu Leu Gln Ile Leu Xaa
1               5                   10                  15

Glu Gln Glu Lys Gln Glu Lys Glu Lys Gln Gln Ala Lys Thr Asn Ala
            20                  25                  30

Xaa Ile Leu Ala Gln Val
        35
```

```
<210> SEQ ID NO 9
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)2-(gamma-
      glu)2-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 9

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 10
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)2-(gamma-
      glu)2-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 10

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 11
<211> LENGTH: 38
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-(gamma-glu)-(gamma-glu)-CO-(CH2)18-
      COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 11

Ile Val Leu Ser Leu Asp Val Pro Ile Gly Leu Leu Gln Ile Leu Leu
1               5                  10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 12
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-([2-(2-Amino-ethoxy)-ethoxy]-acetyl)-
      (gamma-glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 12

Ile Val Leu Ser Leu Asp Val Pro Ile Gly Leu Leu Gln Ile Leu Leu
1               5                  10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 13
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-([2-(2-Amino-ethoxy)-ethoxy]-
```

```
      acetyl)2-(gamma-glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 13

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 14
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)-(gamma-glu)-
      (gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 14

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 15
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 15

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 16
```

```
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: METHYLATION
<220> FEATURE:
<221> NAME/KEY: MISC_FEATURE
<222> LOCATION: (3)..(3)
<223> OTHER INFORMATION: Xaa at position 3 is Leu or Thr
<220> FEATURE:
<221> NAME/KEY: MISC_FEATURE
<222> LOCATION: (16)..(16)
<223> OTHER INFORMATION: Xaa at position 16 is Leu or Ile
<220> FEATURE:
<221> NAME/KEY: MOD_RES
<222> LOCATION: (29)..(29)
<223> OTHER INFORMATION: Lys at 29 is modified at the epsilon-amine with
      -X5-X6, where X5 is 1 to 4 amino acids and/or 1 to 4 ([2-(2-Amino-
      ethoxy)-ethoxy]-acetyl) moieties; X6 is C14-C24 fatty acid.
<220> FEATURE:
<221> NAME/KEY: MISC_FEATURE
<222> LOCATION: (33)..(33)
<223> OTHER INFORMATION: Xaa at position 33 is Gln or Glu
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 16

Ile Val Xaa Ser Leu Asp Val Pro Ile Gly Leu Leu Gln Ile Leu Xaa
1               5                   10                  15

Glu Gln Glu Lys Gln Glu Lys Glu Lys Gln Gln Ala Lys Thr Asn Ala
            20                  25                  30

Xaa Ile Leu Ala Gln Val
        35

<210> SEQ ID NO 17
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)2-CO-(CH2)x-
      COOH, where x is 16 or 18
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 17

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30
```

```
Gln Ile Leu Ala Gln Val
        35

<210> SEQ ID NO 18
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa at position 3 is Leu or Thr
<220> FEATURE:
<221> NAME/KEY: MISC_FEATURE
<222> LOCATION: (16)..(16)
<223> OTHER INFORMATION: Xaa at position 16 is Leu or Ile
<220> FEATURE:
<221> NAME/KEY: MISC_FEATURE
<222> LOCATION: (33)..(33)
<223> OTHER INFORMATION: Xaa at position 33 is Gln or Glu
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 18

Ile Val Xaa Ser Leu Asp Val Pro Ile Gly Leu Leu Gln Ile Leu Xaa
1               5                   10                  15

Glu Gln Glu Lys Gln Glu Lys Glu Lys Gln Gln Ala Lys Thr Asn Ala
            20                  25                  30

Xaa Ile Leu Ala Gln Val
        35

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Glu Lys Gln Glu Lys Glu Lys Gln
1               5

<210> SEQ ID NO 20
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 20

Ile Val Leu Ser Leu Asp Val Pro Ile Gly Leu Leu Gln Ile Leu Leu
1               5                   10                  15
```

```
Glu Gln Glu Lys Gln Glu Lys Glu Lys Gln Gln Ala Thr Thr Asn Ala
            20                  25                  30

Arg Ile Leu Ala Arg Val
            35

<210> SEQ ID NO 21
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (14)..(14)
<223> OTHER INFORMATION: Lys at position 14 is chemically modified
      through conjugation to the epsilon-amino group of the K side-chain
      with (gamma-glu)CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 21

Ile Val Leu Ser Leu Asp Val Pro Ile Gly Leu Leu Gln Lys Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
            35

<210> SEQ ID NO 22
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (15)..(15)
<223> OTHER INFORMATION: Lys at position 15 is chemically modified
      through conjugation to the epsilon-amino group of the K side-chain
      with (gama-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 22

Ile Val Leu Ser Leu Asp Val Pro Ile Gly Leu Leu Gln Ile Lys Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
            35

<210> SEQ ID NO 23
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (17)..(17)
<223> OTHER INFORMATION: Lys at position 17 is chemically modified
      through conjugation to the epsilon-amino group of the K side-chain
      with (gamma-glu)-CO-(CH2)14-CH3
```

```
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 23

Ile Val Leu Ser Leu Asp Val Pro Ile Gly Leu Leu Gln Ile Leu Leu
1               5                   10                  15

Lys Gln Glu Lys Gln Glu Lys Glu Lys Gln Gln Ala Thr Thr Asn Ala
            20                  25                  30

Arg Ile Leu Ala Arg Val
            35

<210> SEQ ID NO 24
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
<223> OTHER INFORMATION: Lys at position 19 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 24

Ile Val Leu Ser Leu Asp Val Pro Ile Gly Leu Leu Gln Ile Leu Leu
1               5                   10                  15

Glu Gln Lys Lys Gln Glu Lys Glu Lys Gln Gln Ala Thr Thr Asn Ala
            20                  25                  30

Arg Ile Leu Ala Arg Val
            35

<210> SEQ ID NO 25
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 25

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
            35

<210> SEQ ID NO 26
```

```
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Lys at position 21 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 26

Ile Val Leu Ser Leu Asp Val Pro Ile Gly Leu Leu Gln Ile Leu Leu
1               5                   10                  15

Glu Gln Glu Lys Lys Glu Lys Glu Lys Gln Gln Ala Thr Thr Asn Ala
            20                  25                  30

Arg Ile Leu Ala Arg Val
        35

<210> SEQ ID NO 27
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Lys at position 22 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 27

Ile Val Leu Ser Leu Asp Val Pro Ile Gly Leu Leu Gln Ile Leu Leu
1               5                   10                  15

Glu Gln Glu Lys Gln Lys Lys Glu Lys Gln Gln Ala Thr Thr Asn Ala
            20                  25                  30

Arg Ile Leu Ala Arg Val
        35

<210> SEQ ID NO 28
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Lys at position 23 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 28
```

```
Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
        35
```

<210> SEQ ID NO 29
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Lys at position 24 is chemically modified
      through conjugation to the epsilon-amino group of the K side-chain
      with gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 29

```
Ile Val Leu Ser Leu Asp Val Pro Ile Gly Leu Leu Gln Ile Leu Leu
1               5                   10                  15

Glu Gln Glu Lys Gln Glu Lys Lys Lys Gln Gln Ala Thr Thr Asn Ala
            20                  25                  30

Arg Ile Leu Ala Arg Val
        35
```

<210> SEQ ID NO 30
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Lys at position 25 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 30

```
Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
        35
```

<210> SEQ ID NO 31
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)

```
<223> OTHER INFORMATION: Lys at position 25 is chemically modified
      through conjugation to the epsilon-amino group of the K side-chain
      with (gamma-glu)-(gamma-glu)- CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 31

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
        35

<210> SEQ ID NO 32
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Lys at position 25 is chemically modified
      through conjugation to the epsilon-amino group of the K side-chain
      with ([2-(2-Amino-ethoxy)-ethoxy]-acetyl)-(gamma-glu)- CO-(CH2)14-
      CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 32

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
        35

<210> SEQ ID NO 33
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Lys at position 26 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 33

Ile Val Leu Ser Leu Asp Val Pro Ile Gly Leu Leu Gln Ile Leu Leu
1               5                   10                  15

Glu Gln Glu Lys Gln Glu Lys Glu Lys Lys Gln Ala Thr Thr Asn Ala
            20                  25                  30

Arg Ile Leu Ala Arg Val
```

```
<210> SEQ ID NO 34
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Lys at position 26 is chemically modified
      through conjugation to the epsilon-amino group of the K side-chain
      with (gamma-glu)-(gamma-glu)- CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 34

Ile Val Leu Ser Leu Asp Val Pro Ile Gly Leu Leu Gln Ile Leu Leu
1               5                   10                  15

Glu Gln Glu Lys Gln Glu Lys Glu Lys Lys Gln Ala Thr Thr Asn Ala
            20                  25                  30

Arg Ile Leu Ala Arg Val
        35

<210> SEQ ID NO 35
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: Lys at position 27 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 35

Ile Val Leu Ser Leu Asp Val Pro Ile Gly Leu Leu Gln Ile Leu Leu
1               5                   10                  15

Glu Gln Glu Lys Gln Glu Lys Glu Lys Gln Lys Ala Thr Thr Asn Ala
            20                  25                  30

Arg Ile Leu Ala Arg Val
        35

<210> SEQ ID NO 36
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (28)..(28)
<223> OTHER INFORMATION: Lys at position 28 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
```

C-terminal carboxyl

<400> SEQUENCE: 36

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Lys Thr Thr Asn Ala
            20                  25                  30

Arg Ile Leu Ala Arg Val
        35

<210> SEQ ID NO 37
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 37

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Arg Ile Leu Ala Arg Val
        35

<210> SEQ ID NO 38
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 38

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Arg Ile Leu Ala Arg Val
        35

<210> SEQ ID NO 39
<211> LENGTH: 38
<212> TYPE: PRT
<213> ORGANISM: Artificial Sequence
<220> FEATURE:

```
<223> OTHER INFORMATION: Synthetic Construct
<220> FEATURE:
<221> NAME/KEY: MOD_RES
<222> LOCATION: (30)..(30)
<223> OTHER INFORMATION: Lys at position 30 is chemically modified
      through conjugation to the epsilon-amino group of the K side-chain
      with (gamma-glu)-CO-(CH2)14-CH3
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 39

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Lys Asn Ala
            20                  25                  30

Arg Ile Leu Ala Arg Val
        35

<210> SEQ ID NO 40
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (14)..(14)
<223> OTHER INFORMATION: Lys at position 14 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 40

Ile Val Leu Ser Leu Asp Val Pro Ile Gly Leu Leu Gln Lys Leu Leu
1               5                   10                  15

Glu Gln Glu Lys Gln Glu Lys Glu Lys Gln Gln Ala Thr Thr Asn Ala
            20                  25                  30

Gln Ile Leu Ala His Val
        35

<210> SEQ ID NO 41
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (15)..(15)
<223> OTHER INFORMATION: Lys at position 15 is chemically modified
      through conjugation to the epsilon-amino group of the K side-chain
 with
      ([2-(2-Amino-ethoxy)-ethoxy]-acetyl)2-(gamma-glu)-(gamma-glu)-CO-
      (CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 41

Ile Val Leu Ser Leu Asp Val Pro Ile Gly Leu Leu Gln Ile Lys Leu
```

```
                1               5                  10                  15
Glu Gln Glu Lys Gln Glu Lys Glu Lys Gln Gln Ala Thr Thr Asn Ala
                20                  25                  30

Gln Ile Leu Ala His Val
        35

<210> SEQ ID NO 42
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (16)..(16)
<223> OTHER INFORMATION: Lys at position 16 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 42

Ile Val Leu Ser Leu Asp Val Pro Ile Gly Leu Leu Gln Ile Leu Lys
1               5                  10                  15

Glu Gln Glu Lys Gln Glu Lys Glu Lys Gln Gln Ala Thr Thr Asn Ala
                20                  25                  30

Gln Ile Leu Ala His Val
        35

<210> SEQ ID NO 43
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (17)..(17)
<223> OTHER INFORMATION: Lys at position 17 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 43

Ile Val Leu Ser Leu Asp Val Pro Ile Gly Leu Leu Gln Ile Leu Leu
1               5                  10                  15

Lys Gln Glu Lys Gln Glu Lys Glu Lys Gln Gln Ala Thr Thr Asn Ala
                20                  25                  30

Gln Ile Leu Ala His Val
        35

<210> SEQ ID NO 44
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (18)..(18)
<223> OTHER INFORMATION: Lys at position 18 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 44

Ile Val Leu Ser Leu Asp Val Pro Ile Gly Leu Leu Gln Ile Leu Leu
1               5                  10                  15

Glu Lys Glu Lys Gln Glu Lys Glu Lys Gln Gln Ala Thr Thr Asn Ala
            20                  25                  30

Gln Ile Leu Ala His Val
        35

<210> SEQ ID NO 45
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Lys at position 21 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 45

Ile Val Leu Ser Leu Asp Val Pro Ile Gly Leu Leu Gln Ile Leu Leu
1               5                  10                  15

Glu Gln Glu Lys Lys Glu Lys Glu Lys Gln Gln Ala Thr Thr Asn Ala
            20                  25                  30

Gln Ile Leu Ala His Val
        35

<210> SEQ ID NO 46
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Lys at position 25 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 46

Ile Val Leu Ser Leu Asp Val Pro Ile Gly Leu Leu Gln Ile Leu Leu
1               5                  10                  15

Glu Gln Glu Lys Gln Glu Lys Glu Lys Gln Gln Ala Thr Thr Asn Ala
```

Gln Ile Leu Ala His Val
        35

<210> SEQ ID NO 47
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Lys at position 26 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 47

Ile Val Leu Ser Leu Asp Val Pro Ile Gly Leu Leu Gln Ile Leu Leu
1               5                   10                  15

Glu Gln Glu Lys Gln Glu Lys Glu Lys Lys Gln Ala Thr Thr Asn Ala
            20                  25                  30

Gln Ile Leu Ala His Val
        35

<210> SEQ ID NO 48
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 48

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala His Val
        35

<210> SEQ ID NO 49
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Lys at position 10 is chemically modified
      through conjugation to the epsilon-amino group of the K side-chain -continued

```
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 49

Ile Val Leu Ser Leu Asp Val Pro Ile Lys Leu Leu Gln Ile Leu Leu
1               5                   10                  15

Glu Gln Glu Lys Gln Glu Lys Glu Lys Gln Gln Ala Thr Thr Asn Ala
            20                  25                  30

Gln Ile Leu Ala Gln Val
        35

<210> SEQ ID NO 50
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (17)..(17)
<223> OTHER INFORMATION: Lys at position 17 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 50

Ile Val Leu Ser Leu Asp Val Pro Ile Gly Leu Leu Gln Ile Leu Leu
1               5                   10                  15

Lys Gln Glu Lys Gln Glu Lys Glu Lys Gln Gln Ala Thr Thr Asn Ala
            20                  25                  30

Gln Ile Leu Ala Gln Val
        35

<210> SEQ ID NO 51
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Lys at position 26 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 51

Ile Val Leu Ser Leu Asp Val Pro Ile Gly Leu Leu Gln Ile Leu Leu
1               5                   10                  15

Glu Gln Glu Lys Gln Glu Lys Glu Lys Lys Gln Ala Thr Thr Asn Ala
            20                  25                  30

Gln Ile Leu Ala Gln Val
```

```
                35

<210> SEQ ID NO 52
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 52

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 53
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (17)..(17)
<223> OTHER INFORMATION: Lys at position 17 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 53

Ile Val Leu Ser Leu Asp Val Pro Ile Gly Leu Leu Gln Ile Leu Leu
1               5                   10                  15

Lys Gln Glu Lys Gln Glu Lys Glu Lys Gln Gln Ala Thr Glu Asn Ala
            20                  25                  30

Gln Ile Leu Ala Gln Val
        35

<210> SEQ ID NO 54
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Lys at position 26 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
```

```
<221> NAME/KEY: MOD_RES
<222> LOCATION: (38)..(38)
<223> OTHER INFORMATION: Val at position 38 is amidated at the
      C-terminal carboxyl

<400> SEQUENCE: 54

Ile Val Leu Ser Leu Asp Val Pro Ile Gly Leu Leu Gln Ile Leu Leu
1               5                   10                  15

Glu Gln Glu Lys Gln Glu Lys Glu Lys Lys Gln Ala Thr Glu Asn Ala
            20                  25                  30

Gln Ile Leu Ala Gln Val
            35

<210> SEQ ID NO 55
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 55

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Glu Asn Ala
            20                  25                  30

Gln Ile Leu Ala Gln Val
            35

<210> SEQ ID NO 56
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)2-(gamma-glu)-(gamma-
      glu)-CO-(CH2)16-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 56

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Glu Asn Ala
            20                  25                  30

Gln Ile Leu Ala Gln Val
            35
```

```
<210> SEQ ID NO 57
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with ([2-(2-Amino-ethoxy)-ethoxy]-acetyl)-(gamma-glu)-(gamma-
      glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 57

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Glu Asn Ala
            20                  25                  30

Glu Ile Leu Ala Gln Val
        35

<210> SEQ ID NO 58
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 58

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Glu Asn Ala
            20                  25                  30

Glu Ile Leu Ala Gln Val
        35

<210> SEQ ID NO 59
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
```

-continued

```
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)-(gamma-glu)-
      (gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 59

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Glu Asn Ala
            20                  25                  30

Glu Ile Leu Ala Gln Val
            35

<210> SEQ ID NO 60
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)2-(gamma-
      glu)2-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 60

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
            35

<210> SEQ ID NO 61
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-gu)-([2-(2-Amino-ethoxy)-ethoxy]-acetyl)-(gamma-glu)-
      (gamma-glu)-CO-(CH2)18-COOH
<220> FEATURE:
<221> NAME/KEY: MOD_RES
```

```
<222> LOCATION: (38)..(38)
<223> OTHER INFORMATION: Val at position 38 is amidated at the
      C-terminal carboxyl

<400> SEQUENCE: 61

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
            35

<210> SEQ ID NO 62
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-([2-(2-Amino-ethoxy)-ethoxy]-
      acetyl)2-(gamma-glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 62

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
            35

<210> SEQ ID NO 63
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-([2-(2-Amino-ethoxy)-ethoxy]-acetyl)-
      (gamma-glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 63

Ile Val Leu Ser Leu Asp Val Pro Ile Gly Leu Leu Gln Ile Leu Leu
1               5                   10                  15
```

```
Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 64
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-(gamma-glu)-(gamma-glu)-(gamma-glu)-CO-(CH2)18-
      COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 64

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 65
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)2-(gamma-
      glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 65

Ile Val Thr Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Gln Ile Leu Ala Gln Val
        35

<210> SEQ ID NO 66
<211> LENGTH: 38
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Methylation
<220> FEATURE:
<221> NAME/KEY: MOD_RES
<222> LOCATION: (29)..(29)
<223> OTHER INFORMATION: Lys at position 29 is chemically modified
      through conjugation to the epsilon-amino group of the K side-chain
      with (gamma-glu)-([2-(2-Amino-ethoxy)-ethoxy]-acetyl)2-(gamma-
      glu)-(gamma-glu)-CO-(CH2)18-COOH
<220> FEATURE:
<221> NAME/KEY: MOD_RES
<222> LOCATION: (38)..(38)
<223> OTHER INFORMATION: Val at position 38 is amidated at the
      C-terminal carboxyl

<400> SEQUENCE: 66

Ile Val Thr Ser Leu Asp Val Pro Ile Gly Leu Leu Gln Ile Leu Leu
1               5                   10                  15

Glu Gln Glu Lys Gln Glu Lys Glu Lys Gln Gln Ala Lys Thr Asn Ala
            20                  25                  30

Glu Ile Leu Ala Gln Val
        35

<210> SEQ ID NO 67
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (1)..(1)
<223> OTHER INFORMATION: UNMODIFIED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa at postiion 3 is Leu or Thr
<220> FEATURE:
<221> NAME/KEY: MISC_FEATURE
<222> LOCATION: (16)..(16)
<223> OTHER INFORMATION: Xaa at postiion 16 is Leu or Ile
<220> FEATURE:
<221> NAME/KEY: MOD_RES
<222> LOCATION: (20)..(20)
<223> OTHER INFORMATION: Lys at position 20 may be modified as described
      herein.
<220> FEATURE:
<221> NAME/KEY: MOD_RES
<222> LOCATION: (23)..(23)
<223> OTHER INFORMATION: Lys at position 23 may be modified as described
      herein.
<220> FEATURE:
<221> NAME/KEY: MOD_RES
<222> LOCATION: (25)..(25)
<223> OTHER INFORMATION: Lys at position 25 may be modified as described
      herein.
<220> FEATURE:
<221> NAME/KEY: MISC_FEATURE
<222> LOCATION: (30)..(30)
<223> OTHER INFORMATION: Xaa at postiion 30 is Thr or Glu
<220> FEATURE:
```

```
<221> NAME/KEY: MISC_FEATURE
<222> LOCATION: (33)..(33)
<223> OTHER INFORMATION: Xaa at postiion 33 is Gln, Arg, or Glu
<220> FEATURE:
<221> NAME/KEY: MISC_FEATURE
<222> LOCATION: (37)..(37)
<223> OTHER INFORMATION: Xaa at postiion 37 is Gln, His, or Arg
<220> FEATURE:
<221> NAME/KEY: MOD_RES
<222> LOCATION: (38)..(38)
<223> OTHER INFORMATION: Val at postiion 38 is amidated at the
      C-terminal carboxyl

<400> SEQUENCE: 67

Ile Val Xaa Ser Leu Asp Val Pro Ile Gly Leu Leu Gln Ile Leu Xaa
1               5                   10                  15

Glu Gln Glu Lys Gln Glu Lys Glu Lys Gln Gln Ala Thr Xaa Asn Ala
            20                  25                  30

Xaa Ile Leu Ala Xaa Val
        35

<210> SEQ ID NO 68
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: UNMODIFIED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa at position 3 is Leu or Thr
<220> FEATURE:
<221> NAME/KEY: MISC_FEATURE
<222> LOCATION: (10)..(10)
<223> OTHER INFORMATION: Xaa at position 10 is Gly or Lys
<220> FEATURE:
<221> NAME/KEY: MOD_RES
<222> LOCATION: (10)..(10)
<223> OTHER INFORMATION: Lys at position 10 may be modified as described
      herein.
<220> FEATURE:
<221> NAME/KEY: MOD_RES
<222> LOCATION: (14)..(14)
<223> OTHER INFORMATION: Lys at position 14 may be modified as described
      herein.
<220> FEATURE:
<221> NAME/KEY: MISC_FEATURE
<222> LOCATION: (14)..(14)
<223> OTHER INFORMATION: Xaa at position 14 is Ile or Lys
<220> FEATURE:
<221> NAME/KEY: MOD_RES
<222> LOCATION: (15)..(15)
<223> OTHER INFORMATION: Lys at position 15 may be modified as described
      herein.
<220> FEATURE:
<221> NAME/KEY: MISC_FEATURE
<222> LOCATION: (15)..(15)
<223> OTHER INFORMATION: Xaa at position 15 is Leu or Lys
<220> FEATURE:
<221> NAME/KEY: MOD_RES
<222> LOCATION: (16)..(16)
<223> OTHER INFORMATION: Lys at position 16 may be modified as described
      herein.
```

-continued

```
<220> FEATURE:
<221> NAME/KEY: MISC_FEATURE
<222> LOCATION: (16)..(16)
<223> OTHER INFORMATION: Xaa at position 16 is Leu, Ile, or Lys
<220> FEATURE:
<221> NAME/KEY: MOD_RES
<222> LOCATION: (17)..(17)
<223> OTHER INFORMATION: Lys at position 17 may be modified as described
      herein.
<220> FEATURE:
<221> NAME/KEY: MISC_FEATURE
<222> LOCATION: (17)..(17)
<223> OTHER INFORMATION: Xaa at position 17 is Glu or Lys
<220> FEATURE:
<221> NAME/KEY: MOD_RES
<222> LOCATION: (18)..(18)
<223> OTHER INFORMATION: Lys at position 18 may be modified as described
      herein.
<220> FEATURE:
<221> NAME/KEY: MISC_FEATURE
<222> LOCATION: (18)..(18)
<223> OTHER INFORMATION: Xaa at position 18 is Gln or Lys
<220> FEATURE:
<221> NAME/KEY: MOD_RES
<222> LOCATION: (19)..(19)
<223> OTHER INFORMATION: Lys at position 19 may be modified as described
      herein.
<220> FEATURE:
<221> NAME/KEY: MISC_FEATURE
<222> LOCATION: (19)..(19)
<223> OTHER INFORMATION: Xaa at position 19 is Glu or Lys
<220> FEATURE:
<221> NAME/KEY: MOD_RES
<222> LOCATION: (20)..(20)
<223> OTHER INFORMATION: Lys at position 20 may be modified as described
      herein.
<220> FEATURE:
<221> NAME/KEY: MOD_RES
<222> LOCATION: (21)..(21)
<223> OTHER INFORMATION: Lys at position 21 may be modified as described
      herein.
<220> FEATURE:
<221> NAME/KEY: MISC_FEATURE
<222> LOCATION: (21)..(21)
<223> OTHER INFORMATION: Xaa at position 21 is Gln or Lys
<220> FEATURE:
<221> NAME/KEY: MOD_RES
<222> LOCATION: (22)..(22)
<223> OTHER INFORMATION: Lys at position 22 may be modified as described
      herein.
<220> FEATURE:
<221> NAME/KEY: MISC_FEATURE
<222> LOCATION: (22)..(22)
<223> OTHER INFORMATION: Xaa at position 22 is Glu or Lys
<220> FEATURE:
<221> NAME/KEY: MOD_RES
<222> LOCATION: (23)..(23)
<223> OTHER INFORMATION: Lys at position 23 may be modified as described
      herein.
<220> FEATURE:
<221> NAME/KEY: MOD_RES
<222> LOCATION: (24)..(24)
<223> OTHER INFORMATION: Lys at position 24 may be modified as described
      herein.
<220> FEATURE:
<221> NAME/KEY: MISC_FEATURE
<222> LOCATION: (24)..(24)
<223> OTHER INFORMATION: Xaa at position 24 is Glu or Lys
<220> FEATURE:
<221> NAME/KEY: MOD_RES
<222> LOCATION: (25)..(25)
<223> OTHER INFORMATION: Lys at position 25 may be modified as described
      herein.
<220> FEATURE:
<221> NAME/KEY: MOD_RES
<222> LOCATION: (26)..(26)
<223> OTHER INFORMATION: Lys at position 26 may be modified as described
      herein.
<220> FEATURE:
```

```
<221> NAME/KEY: MISC_FEATURE
<222> LOCATION: (26)..(26)
<223> OTHER INFORMATION: Xaa at position 26 is Gln or Lys
<220> FEATURE:
<221> NAME/KEY: MOD_RES
<222> LOCATION: (27)..(27)
<223> OTHER INFORMATION: Lys at position 27 may be modified as described
      herein.
<220> FEATURE:
<221> NAME/KEY: MISC_FEATURE
<222> LOCATION: (27)..(27)
<223> OTHER INFORMATION: Xaa at position 27 is Gln or Lys
<220> FEATURE:
<221> NAME/KEY: MOD_RES
<222> LOCATION: (28)..(28)
<223> OTHER INFORMATION: Lys at position 28 may be modified as described
      herein.
<220> FEATURE:
<221> NAME/KEY: MISC_FEATURE
<222> LOCATION: (28)..(28)
<223> OTHER INFORMATION: Xaa at position 28 is Ala or Lys
<220> FEATURE:
<221> NAME/KEY: MOD_RES
<222> LOCATION: (29)..(29)
<223> OTHER INFORMATION: Lys at position 29 may be modified as described
      herein.
<220> FEATURE:
<221> NAME/KEY: MISC_FEATURE
<222> LOCATION: (29)..(29)
<223> OTHER INFORMATION: Xaa at position 29 is Thr or Lys
<220> FEATURE:
<221> NAME/KEY: MOD_RES
<222> LOCATION: (30)..(30)
<223> OTHER INFORMATION: Lys at position 30 may be modified as described
      herein.
<220> FEATURE:
<221> NAME/KEY: MISC_FEATURE
<222> LOCATION: (30)..(30)
<223> OTHER INFORMATION: Xaa at position 30 is Thr, Glu, or Lys
<220> FEATURE:
<221> NAME/KEY: MISC_FEATURE
<222> LOCATION: (33)..(33)
<223> OTHER INFORMATION: Xaa at position 33 is Gln, Arg, or Glu
<220> FEATURE:
<221> NAME/KEY: MISC_FEATURE
<222> LOCATION: (37)..(37)
<223> OTHER INFORMATION: Xaa at position 37 is Gln, His, or Arg
<220> FEATURE:
<221> NAME/KEY: MOD_RES
<222> LOCATION: (38)..(38)
<223> OTHER INFORMATION: Val at postiion 38 is amidated at the
      C-terminal carboxyl

<400> SEQUENCE: 68

Ile Val Xaa Ser Leu Asp Val Pro Ile Xaa Leu Leu Gln Xaa Xaa Xaa
1               5                   10                  15

Xaa Xaa Xaa Lys Xaa Xaa Lys Xaa Lys Xaa Xaa Xaa Xaa Xaa Asn Ala
            20                  25                  30

Xaa Ile Leu Ala Xaa Val
            35
```